United States Patent
Conolly et al.

(10) Patent No.: US 11,709,212 B2
(45) Date of Patent: *Jul. 25, 2023

(54) PULSED MAGNETIC PARTICLE IMAGING SYSTEMS AND METHODS

(71) Applicant: The Regents of the University of California, Oakland, CA (US)

(72) Inventors: Steven M. Conolly, Palo Alto, CA (US); Patrick W. Goodwill, San Francisco, CA (US); Daniel Hensley, Berkeley, CA (US); Zhi Wei Tay, Berkeley, CA (US); Bo Zheng, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/581,684

(22) Filed: Jan. 21, 2022

(65) Prior Publication Data

US 2022/0221537 A1    Jul. 14, 2022

Related U.S. Application Data

(63) Continuation of application No. 15/998,525, filed on Aug. 16, 2018, now Pat. No. 11,231,469.

(Continued)

(51) Int. Cl.
 *G01R 33/12* (2006.01)
 *G01R 33/10* (2006.01)

(52) U.S. Cl.
 CPC ......... *G01R 33/1276* (2013.01); *G01R 33/10* (2013.01)

(58) Field of Classification Search
 None
 See application file for complete search history.

(56) References Cited

U.S. PATENT DOCUMENTS

| 5,965,214 A | 10/1999 | Crossfield et al. |
| 6,054,924 A | 4/2000 | Dames et al. |

(Continued)

FOREIGN PATENT DOCUMENTS

| EP | 3143929 A1 | 3/2017 |
| JP | 2006525506 A | 11/2006 |

(Continued)

OTHER PUBLICATIONS

International Search Report dated Dec. 14, 2018 from corresponding International Application No. PCT/US2018/000231.

(Continued)

*Primary Examiner* — Douglas X Rodriguez
(74) *Attorney, Agent, or Firm* — Venable LLP; Henry J. Daley; Aziz H. Poonawalla

(57) ABSTRACT

A pulsed magnetic particle imaging system includes a magnetic field generating system that includes at least one magnet, the magnetic field generating system providing a spatially structured magnetic field within an observation region of the magnetic particle imaging system such that the spatially structured magnetic field will have a field-free region (FFR) for an object under observation having a magnetic nanoparticle tracer distribution therein. The pulsed magnetic particle imaging system also includes a pulsed excitation system arranged proximate the observation region, the pulsed excitation system includes an electromagnet and a pulse sequence generator electrically connected to the electromagnet to provide an excitation waveform to the electromagnet, wherein the electromagnet when provided with the excitation waveform generates an excitation magnetic field within the observation region to induce an excitation signal therefrom by at least one of shifting a location or condition of the FFR. The pulsed magnetic particle imaging system further includes a detection system arranged (Continued)

proximate the observation region, the detection system being configured to detect the excitation signal to provide a detection signal. The excitation waveform includes a transient portion and a substantially constant portion.

20 Claims, 59 Drawing Sheets

Related U.S. Application Data

(60) Provisional application No. 62/546,395, filed on Aug. 16, 2017.

(56) References Cited

U.S. PATENT DOCUMENTS

| | | | |
|---|---|---|---|
| 6,076,007 | A | 6/2000 | England et al. |
| 6,144,300 | A | 11/2000 | Dames |
| 6,204,766 | B1 | 3/2001 | Crossfield et al. |
| 6,230,972 | B1 | 5/2001 | Dames et al. |
| 6,323,769 | B1 | 11/2001 | Dames |
| 6,369,965 | B1 | 4/2002 | Dames et al. |
| 6,486,655 | B1 | 11/2002 | Crossfield |
| 6,577,237 | B1 | 6/2003 | Dames |
| 6,595,419 | B1 | 7/2003 | Doyle et al. |
| 2006/0238194 | A1 | 10/2006 | Gleich et al. |
| 2010/0066363 | A1 | 3/2010 | Brazdeikis et al. |
| 2012/0119739 | A1 | 5/2012 | Gleich |
| 2012/0126800 | A1 | 5/2012 | Vernickel et al. |
| 2013/0241548 | A1 | 9/2013 | Gleich et al. |
| 2015/0015247 | A1 | 1/2015 | Goodwill et al. |
| 2017/0020407 | A1 | 1/2017 | Weber |

FOREIGN PATENT DOCUMENTS

| | | |
|---|---|---|
| JP | 2012525193 A | 10/2012 |
| KR | 101 623 116 B1 | 5/2016 |
| WO | 96/31790 A1 | 10/1996 |
| WO | 97/48990 A1 | 12/1997 |
| WO | 98/13708 A1 | 4/1998 |
| WO | 98/15851 A1 | 4/1998 |
| WO | 99/09436 A1 | 2/1999 |
| WO | 99/48044 A1 | 9/1999 |
| WO | 00/10123 A1 | 2/2000 |
| WO | 2011/116229 A2 | 9/2011 |

OTHER PUBLICATIONS

Written Opinion dated Dec. 14, 2018 from corresponding International Application No. PCT/US2018/000231.
Karsten et al., "The Use of Flying Null Technology in the Tracking of Labware in Laboratory Automation", 4 pages.
Crossfield, "Have null, will fly", IEE Review, (Jan. 2001), pp. 31-34.
Sparavigna, Manuscript entitled "Labels discover physics: the development of new labelling methods as of promising research field for applied physics", 16 pages.
Extended European Search Report issued in corresponding European Application No. 18846668.4 dated Apr. 9, 2021.
English translation of as-filed Korean Application No. 20150090507, which was published as KR 101 623 116.
Notice of Reasons For Rejection issued in corresponding Japanese Application No. 2020-508019 dated Mar. 28, 2023.

PULSED MAGNETIC PARTICLE IMAGING SYSTEMS AND METHODS

CROSS-REFERENCE TO RELATED APPLICATION

The application is a continuation of U.S. application Ser. No. 15/998,525, filed Aug. 16, 2018, which claims priority to U.S. Provisional Application No. 62/546,395 filed Aug. 16, 2017, the entire contents of which are hereby incorporated by reference.

This invention was made with government support under Grant Numbers EB019458 and MH106053 and awarded by the National Institutes of Health. The government has certain rights in the invention.

BACKGROUND

Technical Field

The field of the currently claimed embodiments of this invention relates to magnetic particle imaging (MPI) devices and methods. MPI is an imaging modality that constructs images of magnetic nanoparticle tracers in a region of interest.

SUMMARY

A pulsed magnetic particle imaging system according to an embodiment of the current invention includes a magnetic field generating system that includes at least one magnet, the magnetic field generating system providing a spatially structured magnetic field within an observation region of the magnetic particle imaging system such that the spatially structured magnetic field will have a field-free region (FFR) for an object under observation having a magnetic nanoparticle tracer distribution therein. The pulsed magnetic particle imaging system also includes a pulsed excitation system arranged proximate the observation region, the pulsed excitation system includes an electromagnet and a pulse sequence generator electrically connected to the electromagnet to provide an excitation waveform to the electromagnet, wherein the electromagnet when provided with the excitation waveform generates an excitation magnetic field within the observation region to induce an excitation signal therefrom by at least one of shifting a location or condition of the FFR. The pulsed magnetic particle imaging system further includes a detection system arranged proximate the observation region, the detection system being configured to detect the excitation signal to provide a detection signal. The excitation waveform includes a transient portion and a substantially constant portion.

A method of imaging an object using a magnetic nanoparticle tracer according to an embodiment of the current invention includes providing the object with the magnetic nanoparticle tracer; applying a spatially structured magnetic field that has an FFR such that the FFR and surrounding regions of the spatially structured magnetic field intercept the object under observation at a region containing at least a portion of the magnetic nanoparticle tracer; exciting a portion of the magnetic nanoparticle tracer by at least one of changing a property of the FFR or a position of the FFR; detecting changes in magnetization of the magnetic nanoparticle tracer resulting from the exciting while the property of the FFR and the position of the FFR are substantially constant to obtain a detection signal; repeating the exciting and detecting for a plurality of different locations of the FFR within the object to obtain a plurality of detection signals; and processing the plurality of detections signals to render an image of a region of the object.

A device for use with or as a part of a pulsed magnetic particle imaging system according to an embodiment of the current invention includes a pulsed excitation system arranged proximate a sample observation region, the pulsed excitation system includes an electromagnet and a pulse sequence generator electrically connected to the electromagnet to provide an excitation waveform to the electromagnet, wherein the electromagnet provides a magnetic field within the sample observation region to generate an excitation signal from a sample when held by the sample holder in the sample observation region. The device further includes a detection system arranged proximate the sample observation region, the detection system being configured to detect the excitation signal from the sample to provide a detection signal The excitation waveform includes a transient portion and a substantially constant portion.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention are directed to new and/or improved MPI systems and methods. For example, some embodiments use an alternative paradigm for spatially homogeneous excitation or drive fields in which pulsed waveforms containing substantially flat or constant components are used during the MPI scanning process.

Figure 1A:
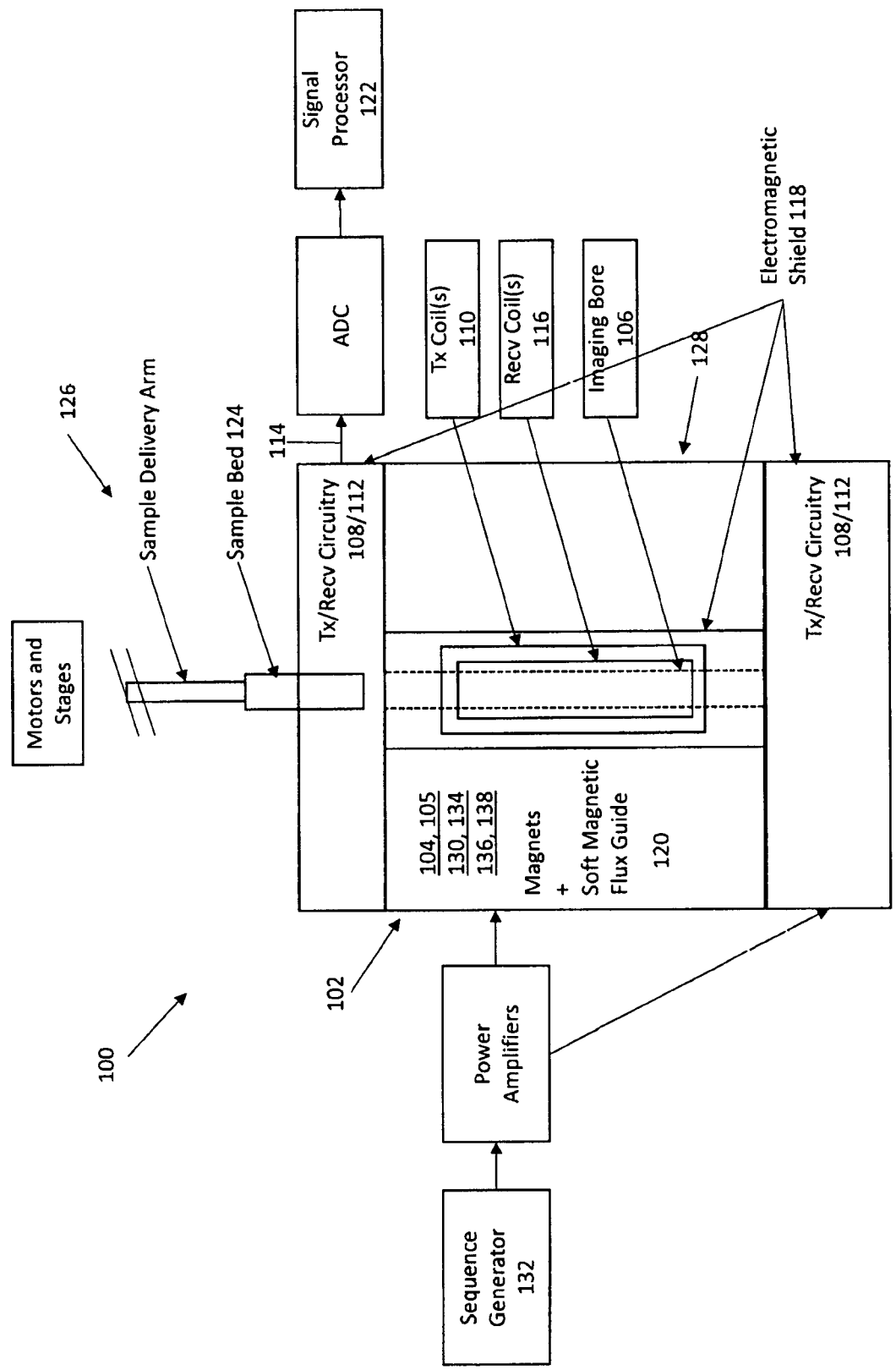
FIG. 1A is a schematic illustration of a pulsed magnetic particle imaging system according to an embodiment of the current invention.

FIG. 1A is a schematic illustration of a pulsed magnetic particle imaging (pMPI) system 100 according to an embodiment of the current invention. The pMPI system 100 includes a magnetic field generating system 102 that includes at least one pair of magnets 104. In some embodiments, the magnetic field generating system 102 can have a second pair of magnets 105, or even magnet arrays or more than two pairs of magnets in some embodiments. The magnets 104, 105, etc. can be permanent magnets, electromagnets, or a combination of both. Some examples of arrangements of magnets 104, 105, etc. will be described in more detail below. The magnetic field generating system 102 provides a spatially structured magnetic field within an observation region 106 of the magnetic particle imaging system 100 such that the spatially structured magnetic field will define a field-free region (FFR) for an object under observation. The object under observation will have a magnetic nanoparticle tracer distribution therein.

The term field-free region (FFR) is intended to refer to a portion of the structured magnetic field that is below the saturation field strength associated with a magnetic nanoparticle tracer when a distribution of the tracer is contained within an object of interest. Note that the FFR does not mean that the magnetic field is zero throughout the region. The FFR can be a localized region around a point, localized around a line or localized around a plane, for example.

The pMPI system 100 also includes a pulsed excitation system 108 arranged proximate the observation region 106. The pulsed excitation system 108 includes an electromagnet 110 and a pulse sequence generator 132 electrically connected to the electromagnet 110 to provide an excitation waveform to the electromagnet 110. However, one should note that the pulsed excitation system 108 is not limited to only one electromagnet 110. There could be one, two, three, four or more electromagnets without limitation as to the particular number of electromagnets. The electromagnet 110 generates an excitation magnetic field within the observation region 106 to induce an excitation signal from the object under observation by at least one of shifting a location or condition of the FFR. The phrase "condition of FFR" can be a size, specific shape, addition of a biasing field, and/or the magnetic field distribution within the FFR, for example. The pulsed excitation system 108 as well as various embodiments of waveforms generated therefrom will be described in more detail below with respect to some particular examples. However, the general concepts of the current invention are not limited to only those particular embodiments.

The pMPI system 100 further includes a detection system 112 arranged proximate the observation region 106. The detection system 112 is configured to detect the excitation signal from the object under observation to provide a detection signal 114. In some embodiments, the detection system 112 can include one or more receiver coils such as receiver coil 116. In some embodiments, there can be one receiver coil, or two receiver coils, or three receiver coils, etc. without limitation as to the particular number of receiver coils. The abbreviations Tx and Rx mean transmitter and receiver, respectively. Some embodiments of the detection system 112 will be described in more detail below. However, the general concepts of the current invention are not limited to only the particular examples described. The excitation waveform produced by the pulsed excitation system 108 includes a transient portion and a substantially constant portion. The waveform may include one pulse or a plurality of pulses. The waveform may also include one or more portions that are not pulses. The term "pulse" refers to a portion of the signal that includes at least one transient portion that is distinguishable from adjacent portions of the signal that are substantially constant. Substantially constant means a slow time variation relative to a time variation of the transient portion. For example, in some embodiments the transient portion can be changing with time twice as fast as changes in the substantially constant portion, three times as fast, ten times as fast, many orders of magnitude faster, or anything in between without limitation for the general concepts of the invention. For example, a pulse can be a simple form, such as, but not limited to, a spike. However, a pulse can have a more complex structure to include a plurality of transient portions and a plurality of substantially constant portions. A pulse can be short in duration, i.e., time, compared to the adjacent substantially constant portions of the signal. The adjacent substantially constant portions are not required to be equal. Short can be at least twice as short, ten times as short, many orders of magnitude shorter, etc. without limitation to the general concepts of the current invention.

In some embodiments, the pMPI system 100 further includes an electromagnetic shield 118 arranged to fully enclose the observation region 106 therein to electromagnetically isolate the observation region 106 from at least the magnetic field generating system 102 and an environment around the pulsed magnetic particle imaging system 100. The electromagnetic shield 118 can be a metal shield, such as, but not limited to, a shield formed from copper plate and/or an alloy of copper. The thickness of this shield may be prescribed by the expected or desired Tx and Rx bandwidths. For example, the thickness may be chosen such that the skin depth blocks all Rx bandwidth interfering signals, but passes certain signals such as slow shift magnetic fields without significant attenuation. For example, the shield can be substantially pure copper about 2-5 mm thick. However, the electromagnetic shield 118 is not limited to these examples and can be constructed from other metals in a variety of forms, thicknesses, etc. We note that the use of a fully enclosed shielding system is important for bi-directional EMI shielding. The sensitive Rx signal may be shielded from external or environmental interfering and noise sources as well as from interfering and noise sources originating in other parts of the system 100, including the magnet systems 104, 105, 130, 136, etc. and passive magnetic field focusing system 120 that produce and/or shift the FFR. Additionally, and importantly, these magnet systems 104, 105, 130, 136, and the passive magnetic field focusing system 120 are themselves shielded from the strong fields produced by the Tx coils 110, preventing magnetic saturation and other untoward interactions.

In some embodiments, as will be described in more detail below, at least a transmission portion (e.g., Tx coils 110) of the pulsed excitation system 108 and a reception portion (e.g., Rx coils 116) of the detection system 112 are enclosed within the electromagnetic shield 118.

In some embodiments, the magnetic field generating system 102 can also include a passive magnetic field focusing element 120 such as a soft magnetic material configured into a shape and arranged relative to the at least one magnet 104 so as to focus, i.e., concentrate, or otherwise guide the magnetic field lines to a desired path therein. FIG. 1A represents these structures schematically. Further examples are illustrated in more detail below.

In some embodiments, the detection system 112 can be configured to detect the excitation signal substantially only during the substantially constant portion of the excitation waveform to avoid feedthrough interference during the transient portions of the excitation waveform to provide the detection signal. For example, electronic circuits can be provided to provide such functionality. The detection system 112 can be, or can include, hard-wired components and/or can include programmable structures. Either way, these are to be interpreted as structural components since a programmable structure can be replaced with hard-wired components such as, but not limited to, ASICs and/or FPGAs, for example. In some embodiments, the detection system 112 can be configured to detect the excitation signal during the transient portion of the excitation waveform, or during both the transient portion and the substantially constant portion of the excitation waveform.

Figure 57:
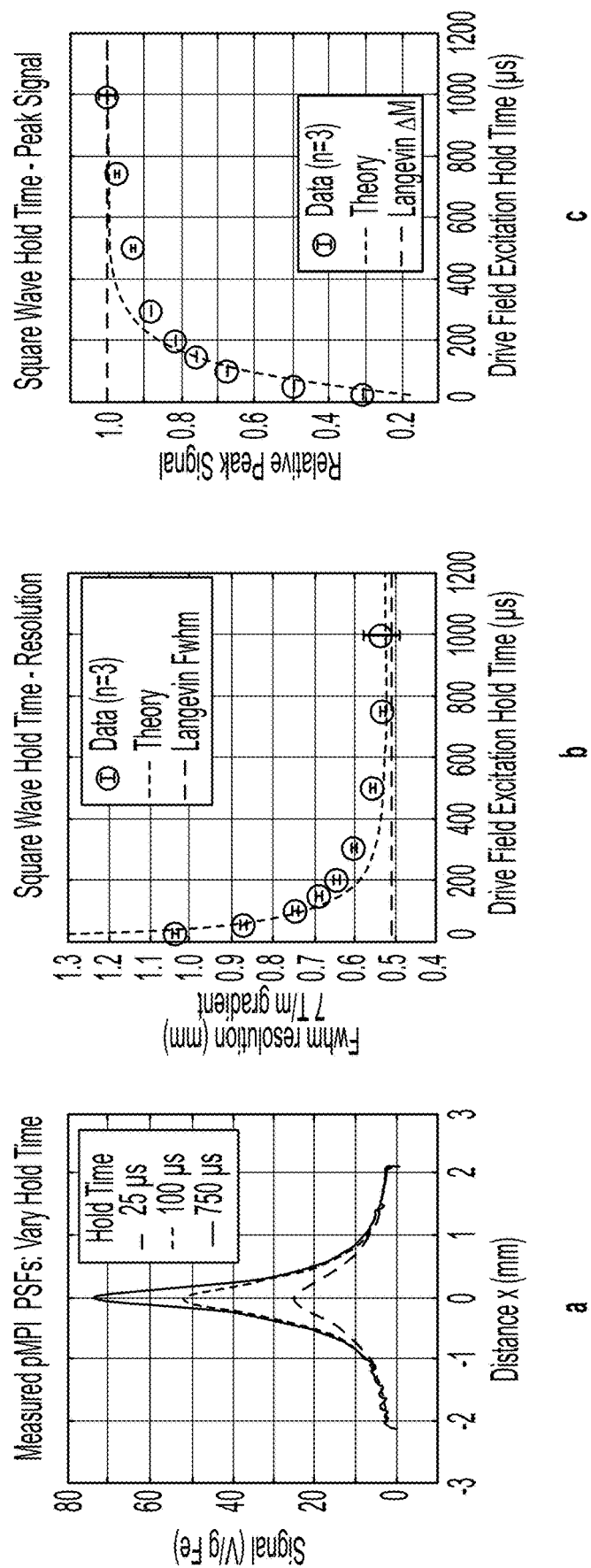
FIG. 57 shows experimental data showing the relationship between substantially constant hold time and pulsed MPI performance.

In some embodiments, the substantially constant portion of the excitation waveform is at least 500 nanoseconds and less than 500 milliseconds. In some embodiments, the substantially constant portion of the excitation waveform is constant to within about 10% of a target amplitude of the excitation waveform. In some embodiments, the transient portion of the excitation waveform has a duration of at least 100 nanoseconds and less than 100 microseconds. In some embodiments, the excitation waveform includes a magnetization preparation portion and a readout portion such that the magnetization preparation portion includes at least a fraction of the transient portion and the readout portion includes at least a fraction of the constant portion. In some embodiments, the magnetization preparation portion dynamically configures a state of tracer magnetization that is in a vicinity of the FFR based on magnetic relaxation properties of the tracer prior to the readout portion. In some embodiments, the magnetization preparation selectively nulls a signal from tracer associated with a specified relaxation state or physical location during the readout portion. In some embodiments, the magnetization preparation encodes the tracer magnetization in such a way as to improve spatial resolution in reconstructed images. In some embodiments, the substantially constant portion is longer than a relaxation time for the magnetic nanoparticle tracer in the FFR. In some embodiments, the readout portion is longer than a relaxation time for the magnetic nanoparticle tracer in the FFR. In some embodiments, the substantially constant portion is long enough to establish a steady-state magnetization in the magnetic nanoparticle tracer in said FFR. In some embodiments, the readout portion is long enough to establish a steady-state magnetization in the magnetic nanoparticle tracer in said FFR. FIG. 57 shows data demonstrating how the achievement of steady-state magnetization can be measured by observing, for example, the experimental relationship between resolution and readout portion or substantially constant portion length or the experimental relationship between peak signal intensity and readout portion or substantially constant portion length. Beginning at, for example, a readout portion or substantially constant portion that is too short to achieve steady-state, as the readout portion or substantially constant portion length is increased, experimental resolution or peak signal intensity values will eventually plateau when the readout portion length or substantially constant portion length is sufficient to establish steady-state magnetization of the tracer. In this manner, a desired readout portion length or substantially constant portion length can be obtained without any a priori knowledge of a tracer's magnetic behavior. In some embodiments, the readout portion is shorter than a relaxation time for the magnetic nanoparticle tracer in the FFR. In some embodiments, a steady-state magnetization distribution is achieved in the tracer distribution by the end of a substantially constant portion of the excitation waveform. In some embodiments this substantially constant portion of the excitation waveform is a terminal readout period. In some embodiments, a magnetization preparation period comprising a collection of one or more transient pulses followed by a terminal readout period is repeated many times in a larger excitation waveform applied during the course of a longer scan. In some embodiments each of these repeated components is associated with a different mean location of the FFR.

In some embodiments, the excitation waveform includes a plurality of pulses, each pulse of the plurality of pulses including at least one transient portion. In some embodiments, the excitation waveform further includes a plurality of constant portions such that the excitation waveform includes a plurality of magnetization preparation portions and a plurality of readout portions such that each magnetization preparation portion of the plurality of magnetization preparation portions includes at least one transient portion of at least one of the plurality of pulses, and such that each readout portion of the plurality of readout portions includes at least a fraction of at least one constant portion of the plurality of constant portions. In some embodiments, the excitation waveform is a square wave. In some embodiments, the excitation waveform is trapezoidal.

In some embodiments, the FFR is a field-free "line" defining a longitudinal, or "long", direction and the excitation waveform is at least partially applied in the longitudinal direction of the field-free line so as to change a condition of the field-free line by displacing a corresponding field-free line structure in a magnetic field space but maintaining shape and location of the field-free line structure. In some embodiments, the FFR is a field-free line defining a longitudinal direction and the excitation waveform is at least partially applied in the plane orthogonal to the longitudinal direction of the field-free line so as to change the position of the field-free line. Here, the phrase "field-free line" does not require a perfectly one-dimensional FFR with zero width in the mathematical sense. The "field-free line" has a width that is smaller than the length of the line. For example, the width can be smaller than the length of the line by at least a factor of 2, or a factor of 10, or a factor of 100, or a factor of 1000, without limitation to these particular examples.

In some embodiments, the pulse sequence generator is configured to provide the plurality of pulses such that each have at least one of preselected shapes, magnitudes, widths or inter-pulse periods to provide a particular pulse sequence encoding. In some embodiments, the pulse sequence generator is configured to provide an excitation waveform that includes a plurality of pulses separated by inter-pulse portions, and each pulse of the plurality of pulses includes a transient portion.

In some embodiments, the pulse sequence generator is configured to provide an excitation waveform that includes a plurality of pulses separated by constant inter-pulse portions, and each pulse of the plurality of pulses has a constant portion between transient portions. In some embodiments, the excitation waveform can approximate a finite-duration square wave with finite transitioning slew rates. In some embodiments, the excitation waveform is trapezoidal. In some embodiments, each constant portion between successive pulses of the plurality of pulses is greater than a preceding constant portion for at least a portion of the pulsed waveform. However, the general concepts of the current invention are not limited to these particular examples.

In some embodiments, the pulsed excitation system includes an LR circuit powered by a linear amplifier in a non-resonant filter chain. In some embodiments, the LR circuit has an inductance between 1 microHenry and 50 microHenries. In some embodiments, the LR circuit has an inductance between 1 microHenry and 30 microHenries.

In some embodiments, the pulsed excitation system includes a resonant switcher circuit. In some embodiments, the detection system includes gain control circuitry to amplify portions of the detection signal that have less feedthrough contamination relative to portions of the detection signal that have more feedthrough contamination.

In some embodiments, the pMPI system 100 further includes a signal processor 122 configured to communicate with the detection system 112 to receive detection signals 114 therefrom. The signal processor 122 is further configured to generate an imaging signal for rendering an image corresponding to regions of the object under observation traversed by the FFR. The signal processor 122 can be, for example, a computer in the general sense, which can be, but is not limited to a desktop computer, a laptop computer, a tablet device, a smart phone, a microcontroller or other system-on-a-chip device, or any networked combination of such devices or portions of such devices. The signal processor can be a programmable processor and/or a hard-wired processor, such as, but not limited to an ASIC and/or an FPGA. Regardless of whether the signal processor 122 is programmable or not, it is to be interpreted as a structural component of the pMPI system 100.

In some embodiments, the pMPI system 100 further includes an object holder 124 configured to be arranged within the observation region 106 of the pMPI system 100. In some embodiments, the pMPI system 100 further includes a mechanical assembly 126 operatively connected to at least one of the object holder 124 or the magnetic field generating system 102 to at least one of translate or rotate a relative position of the FFR.

In some embodiments, the pMPI system 100 further includes a slow-shift electromagnetic system 128 that includes a slow-shift electromagnet 130 and a slow-shift waveform generator 132 disposed proximate the observation region 106 of the pMPI system 100. The slow-shift waveform generator 132 provides waveforms to the slow-shift electromagnet 130 to shift a position of the FFR on a time scale that is slow compared to a timescale of the excitation pulses. In some embodiments, the slow-shift electromagnetic system 128 can include a plurality of slow-shift electromagnets, such as, but not limited to, slow-shift electromagnets 130, 134, 136, 138 for example. In an alternative embodiment, the pMPI system 100 further includes a slow-shift waveform generator 132 that is configured to communicate with the magnetic field generating system 102 to use the same coils as the magnetic field generating system 102, such as, but not limited to, coils 104 and/or 105. In some embodiments, a slow-shift linear motor is configured to move the object being imaged in at least one dimension on a timescale that is slow compared to a timescale of the excitation pulses. In some embodiments, the pMPI system 100 is further configured with a field-free line and a rotating gantry and motor to provide relative rotation between the field-free line and imaging bore 106 containing the sample under study 124. In some embodiments, one or more of the following are mounted to a rotating gantry: main magnets and soft magnetic flux guide (120), slow-shift magnets (130, 134, 136, 138), Tx and Rx coil(s) (110, 116), Tx/Rx circuitry (108, 112), and electromagnet shield (118).

In some embodiments, the magnetic field generating system 102 is dynamically configurable. In addition to dynamic behavior pre-programmed into the sequence generator 132, by the user beforehand, feedback loops may inform an online algorithm or controller logic to provide real-time modifications to excitation waveforms to more fully conform to a desired ideal trajectory. For example, field and/or current sniffer elements may report realized waveforms to the controller for appropriate negative feedback-controlled modification of inputs to the power amplifiers (see, e.g., FIGS. 1A, 42 and 43). In some embodiments, the magnetic field generating system 102 is dynamically configurable so as to dynamically alter the FFR to dynamically change a signal-to-noise ratio and resolution encoded in the detection signal. In some embodiments a user may be enabled to intervene based on scout scan or real-time imaging feedback to dynamically tradeoff SNR and resolution. For example, an interface to the sequence generator 132 may be configured to scale the signals for excitation amplitude or gradient strength dynamically based on user feedback. In some embodiments the gradient strength or pulsed excitation amplitudes may be dynamically weakened or reduced, respectively, in regions of sparse tracer signal to improve SNR at the expense of resolution. In some embodiments, the gradient strength or pulsed excitation amplitudes may be increased in tracer-dense regions to improve resolution at the expense of SNR and possibly imaging speed. In some embodiments, both the gradient strength and pulsed excitation amplitudes may be modified concurrently according to some optimization logic or algorithm. In some embodiments, these dynamic tradeoffs may be automatically performed by an algorithm or logic internal to the sequence generation system 132. In some embodiments, magnetization preparation sequences may be modified based on real-time feedback to achieve the intended magnetization preparation more accurately given closed-loop feedback information. In some embodiments, the sequence generator and feedback elements will be configured to dynamically modify magnetization preparation or other elements of the pulse sequence based on measured, fit, or quantified magnetic relaxation properties of the tracer in the object being imaged. In some embodiments these modifications will account for changing magnetic relaxation properties of the tracer encountered at different locations in the image.

In some embodiments, the pMPI system 100 further includes a signal processing and image rendering system 122 configured to be in communication with the detection system 112 to receive the detection signal 114. The signal processing and image rendering system 122 can be configured to process the detection signal 114 and render an image corresponding to portions of the object under observation containing the magnetic nanoparticle tracer and that was addressed by the FFR.

In some embodiments, the signal processing and image rendering system 122 is configured to process the detection signal 114 and render the image with a spatial resolution of at least 1.5 mm. In some embodiments, the signal processing and image rendering system 122 is configured to process the detection signal 114 and render the image with a spatial resolution of at least 1000 μm to 100 μm. In some embodiments, the signal processing and image rendering system 122 is configured to process the detection signal 114 and render the image to represent at least one of density, mass, concentration or a derivative thereof of the tracer at corresponding image locations. In some embodiments, the signal processing and image rendering system 122 is configured to process the detection signal 114 and render the image to represent a local relaxation time of the tracer at corresponding image locations. In some embodiments, the signal processing and image rendering system 122 is configured to process the detection signal and render the image to represent at least one of a local viscosity, a pH, a magnetic nanoparticle binding event, a local oxidation state, a concentration of a biochemical analyte of interest, or a functionalized magnetic nanoparticle interaction at corresponding image locations. In some embodiments, the signal processing and image rendering system 122 is configured to process the detection signal and render the image to represent kinetic information of local biochemical processes interacting directly or indirectly with a possibly functionalized magnetic nanoparticle tracer.

Another embodiment of the current invention is directed to a method of imaging an object using a magnetic nanoparticle tracer. The method includes providing the object with the magnetic nanoparticle tracer; applying a spatially structured magnetic field that has an FFR such that the FFR and surrounding regions of the spatially structured magnetic field intercept the object under observation at a region containing at least a portion of the magnetic nanoparticle tracer; exciting a portion of the magnetic nanoparticle tracer by at least one of changing a property of the FFR or a position of the FFR; detecting changes in magnetization of the magnetic nanoparticle tracer resulting from the exciting while the property of the FFR and the position of the FFR are substantially constant to obtain a detection signal; repeating the exciting and detecting for a plurality of different locations of the FFR within the object to obtain a plurality of detection signals; and processing the plurality of detections signals to render an image of a region of the object.

In some embodiments, the detecting occurs subsequent to the exciting of the portion of the magnetic nanoparticle tracer. In some embodiments, the detecting occurs during the exciting of the portion of the magnetic nanoparticle tracer. In some embodiments, the detecting occurs both during and subsequent to the exciting of the portion of the magnetic nanoparticle tracer.

In some embodiments, the method further includes administering the magnetic nanoparticle tracer to the object under observation, wherein the magnetic nanoparticle tracer administered comprises magnetic nanoparticles that have an ensemble average diameter of at least 10 nm and less than 100 nm. In some embodiments, the magnetic nanoparticles of the magnetic nanoparticle tracer are at least 25 nm and less than 50 nm. In some embodiments, the magnetic nanoparticles of the magnetic nanoparticle tracer are uniform to within a variance of 5 nm.

In some embodiments, the property of the FFR and the position of the FFR are substantially constant for at least 500 nanoseconds and less than 500 milliseconds during the detecting. In some embodiments, the property of the FFR and the position of the FFR are substantially constant to within about 10% of an amount of change of the FFR and the position of the FFR during the exiting. In some embodiments, the changing the property of the FFR or the position of the FFR has a duration of at least 100 nanoseconds and less than 10 microseconds.

In some embodiments, the processing the plurality of detections signals to render the image of the region of the object renders at least one of a magnetic particle density image, or a magnetic relaxation dynamic parameter image. In some embodiments, the processing the plurality of detections signals to render the image of the region of the object renders a local viscosity. In some embodiments, the processing the plurality of detections signals to render the image of the region of the object renders a local binding state of the tracer.

Another embodiment of the current invention is directed to a device for use with or as a part of a pulsed magnetic particle imaging system. This embodiment can be constructed from components that are similar to or the same as corresponding components in FIG. 1A. Consequently, the same reference numerals from FIG. 1A are used here. In this embodiment, the device includes a pulsed excitation system 108 arranged proximate a sample observation region 106. The pulsed excitation system 108 includes an electromagnet 110 and a pulse sequence generator electrically connected to the electromagnet 110 to provide an excitation waveform to the electromagnet 110. The electromagnet 110 provides a magnetic field within the sample observation region 106 to generate an excitation signal from a sample when held by a sample holder 124 in the sample observation region 106. The device also includes a detection system 112 arranged proximate the sample observation region 106. The detection system 112 is configured to detect the excitation signal from the sample to provide a detection signal 114. The excitation waveform includes a transient portion and a substantially constant portion. The pulsed excitation system 108 and the detection system 112 can be part of a modular structure adapted to convert a non-pulsed MPI system into a pulsed MPI system.

The device can further include a signal processor 122 configure to communicate with the detection system 112 to receive and process the detection signal 114. The signal processor 122 can be further configured to process the detection signal to determine a magnetization relaxation time for magnetic particles within the sample. The device according to this embodiment can further include a sample holder defining the sample observation region.

The following describes some particular embodiments of the current invention in more detail; however, the general concepts of the current invention are not to be limited to these particular examples.

Pulsed Encoding Techniques

Pulsed waveforms can be used to encode the MPI signal in ways generally not attainable when using sinusoidal continuous waveforms. For example, it is possible to temporally separate transmit feedthrough interference from tracer signal. Pulsed waveforms can also allow for measuring the steady-state magnetic physics of the nanoparticle tracer distribution, potentially bypassing blur effects seen in continuous sinusoidal MPI due to finite magnetic response times associated with the tracer. At the same time, pulsed waveforms can provide methods and encoding regimes that allow quantification of these magnetic response times, giving rise to enhanced image contrast and the possibility for measuring additional information. For example, relaxation images that quantify a measure of tracer relaxation physics and report in a spatially resolved manner may also be produced, in addition to tracer density images. In other embodiments, fully four-dimensional imaging datasets may be provided. This data may be obtained simultaneously from the same excitation pulse sequences or via the sequential application of different excitation pulse sequences.

Pulsed waveform sequences may also lead to a second form of spatial information encoding, distinct from the Langevin saturation typically used in MPI, via magnetic relaxation dynamics. More generally, it is possible to use this new encoding to shape tracer magnetization prior to or during encoding periods to affect resolution, SNR, and image contrast in useful ways. For example, in current MPI approaches magnetic relaxation generally acts to degrade resolution and image quality, while in pulsed MPI techniques we can leverage magnetic relaxation to improve resolution.

Requirements for Pulsed Encoding

Figure 1B:
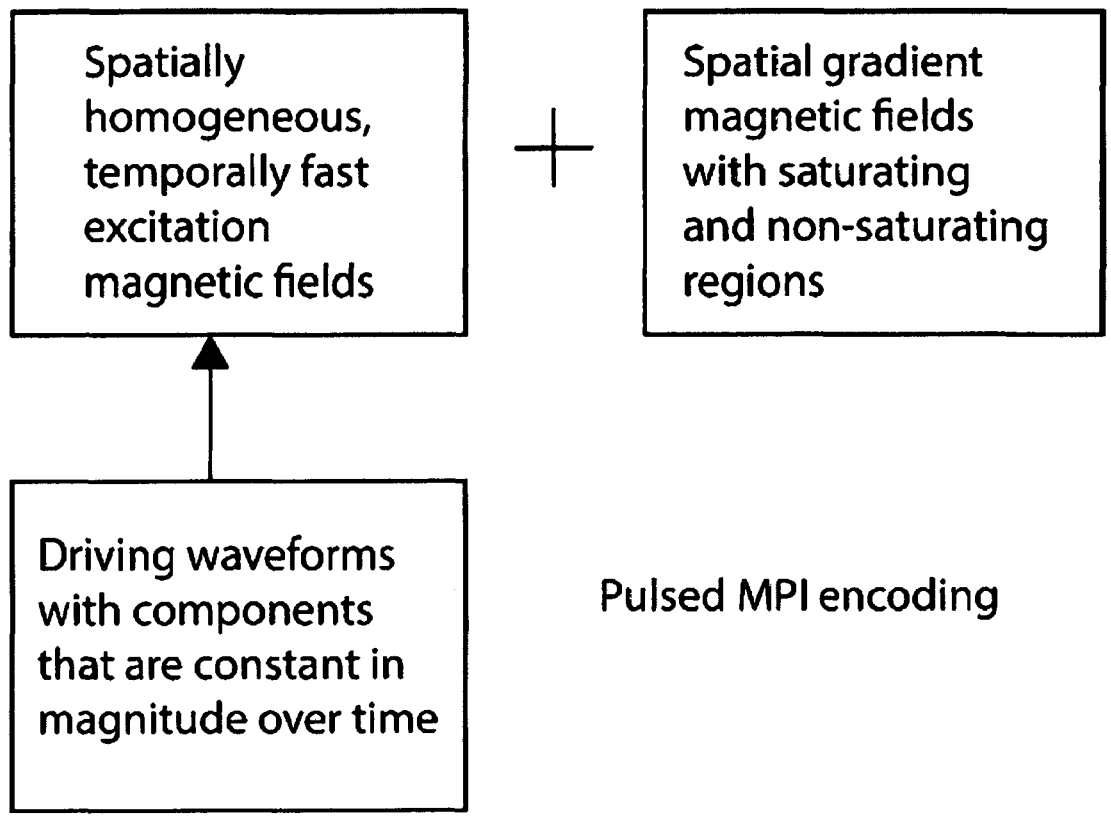
FIG. 1B is a schematic illustration of basic components for pulsed MPI encoding according to an embodiment of the current invention.

As shown in FIG. 1B, the fundamental requirements for pulsed encoding in MPI include a spatially varying magnetic field pattern or structure known as a field-free region (FFR), temporally controllable and spatially homogeneous excitation magnetic field sources, and one or more magnetic field pulses, each containing one or more substantially constant magnetic field waveforms produced by the excitation magnetic field sources. In some embodiments, an FFR may be omitted for calibration or in sensing applications in which there is no need to produce spatially localized images. In some embodiments, one or more spatially homogeneous biasing fields may be applied in addition to the pulsed excitation fields to acquire additional dimensions of data, such as relaxation data, with or without employing a FFR.

Magnetic Saturation

Figure 7:
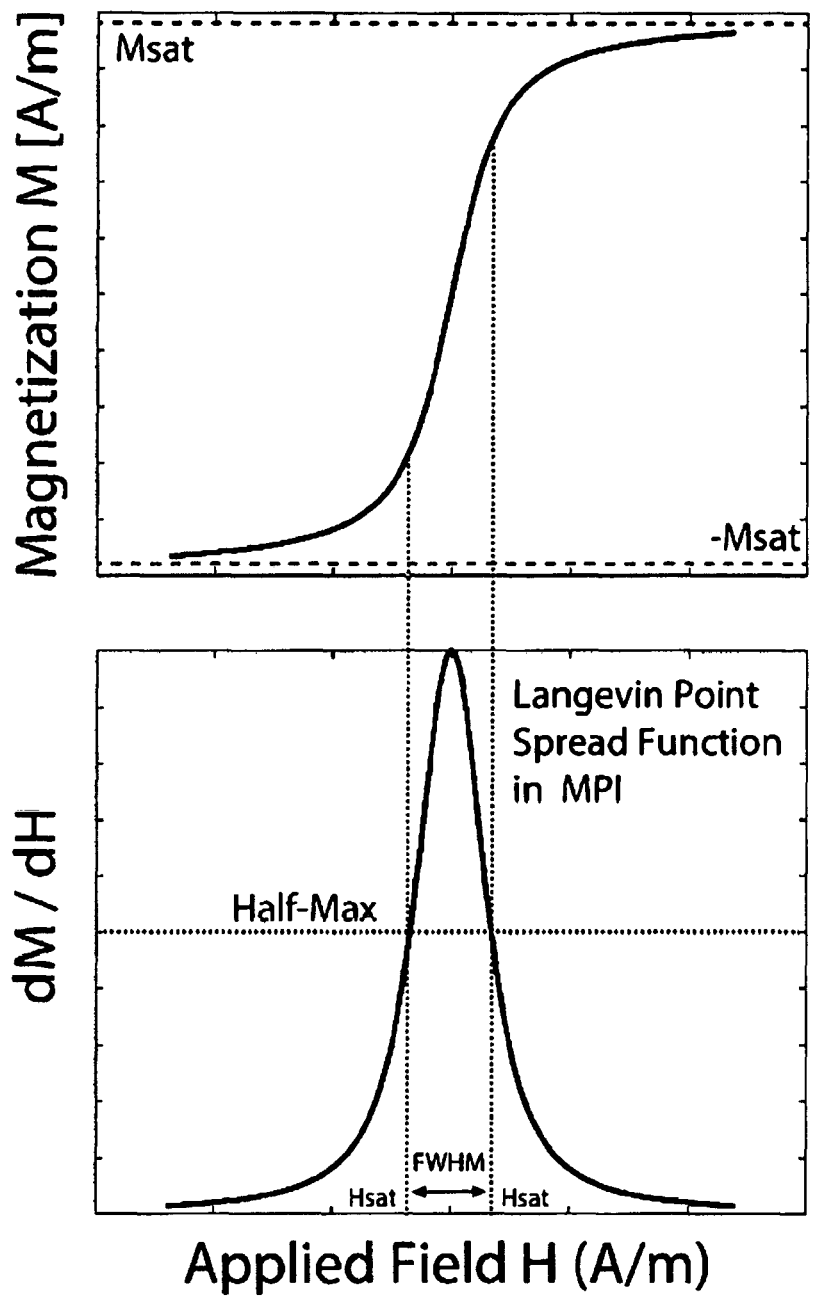
FIG. 7 shows an MPI magnetic tracer magnetization curve and the derivative, which is the ideal PSF in MPI according to some embodiments of the current invention.

MPI images magnetic tracers that can magnetically saturate. The relationship between the applied magnetic field and the nanoparticle magnetization can be described by a magnetization curve, known as a M-H curve, that gives a nanoparticle ensemble's magnetization response for an applied magnetic field (See FIG. 7). At small applied magnetic fields, magnetic nanoparticles rapidly change their magnetization. At large applied fields, the M-H curve asymptotically approaches a plateau or constant value in magnetization. Then, at large total applied field magnitudes, these tracers do not substantially change their magnetization in response to a further increase in applied magnetic field, and so the particles are said to be "saturated." In the case of superparamagnetic iron oxide (SPIO) tracers, the magnetization response of SPIOs in response to an applied magnetic field is understood to follow the Langevin curve.

Establishment of an FFR with Gradient Fields

Figure 2:
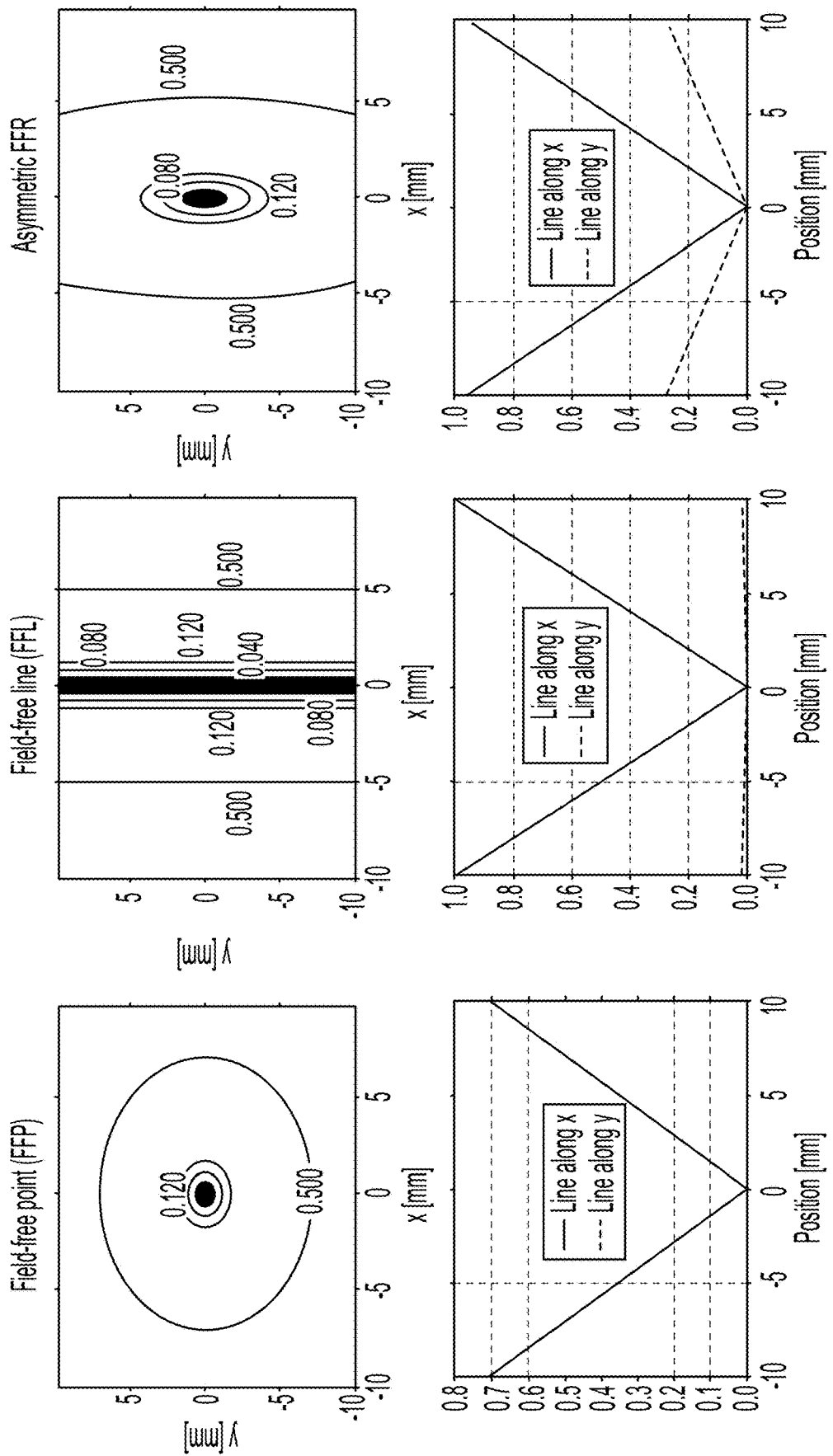
FIG. 2 shows establishment of different FFR structures with gradient fields according to an embodiment of the current invention.

A typical MPI scanning system contains one or more active or passive magnetic field sources that are used to generate a particular spatial field pattern, referred to herein as a FFR. A FFR is defined as the spatial region where the applied magnetic field is below a magnetic saturation value. This can lie in contrast to nearby spatial regions where the applied field is above a magnetic saturation value. FFRs often, but not necessarily, contain linear magnetic field gradients so the magnetic field transitions smoothly between the FFR and nearby saturating magnetic field regions. The FFR may be a field-free point, field-free line, or of a more general shape as depicted in FIG. 2 and subject to the limits imposed by Maxwell's equations.

Homogeneous Fast Excitation Fields

In a typical MPI system, the tracer signal is generated by applying a spatially homogeneous but time-varying magnetic field in superposition with the gradient fields that create the FFR. Homogeneous fields applied in this manner will generally act to shift or translate the FFR in space and in time while maintaining the shape of the FFR. In some embodiments, such as in the case of homogeneous excitation with an applied field coaxial with the line in a FFL, the addition of a homogeneous field does not shift the mean location of the FFR and instead adds a magnetic bias to transform the FFR into a low-field region (LFR), for example.

When using coils that produce homogeneous fields, homogeneity requirements may be on the order of <10% or better across the Field of View (FOV), defined as the amount of magnetic field deviation from nominal, although coils with poorer homogeneity may be used. In MPI, it can be instructive to distinguish between homogeneous excitation fields and homogeneous shift fields even though both types of fields spatially are mathematically equivalent. Excitation fields have high slew rates and provide for fast translation of the FFR that can stimulate the particles to induce voltage signals received by inductive receiver coils, while shift fields can be orders of magnitude stronger and orders of magnitude slower and are used to slowly translate the mean location of the FFR structure across a large FOV inaccessible to the excitation field alone. Pulsed MPI encoding is largely concerned with the faster excitation fields, although shift fields are also still used and enable encoding of larger FOVs, just as in the case of standard MPI.

Figure 3:
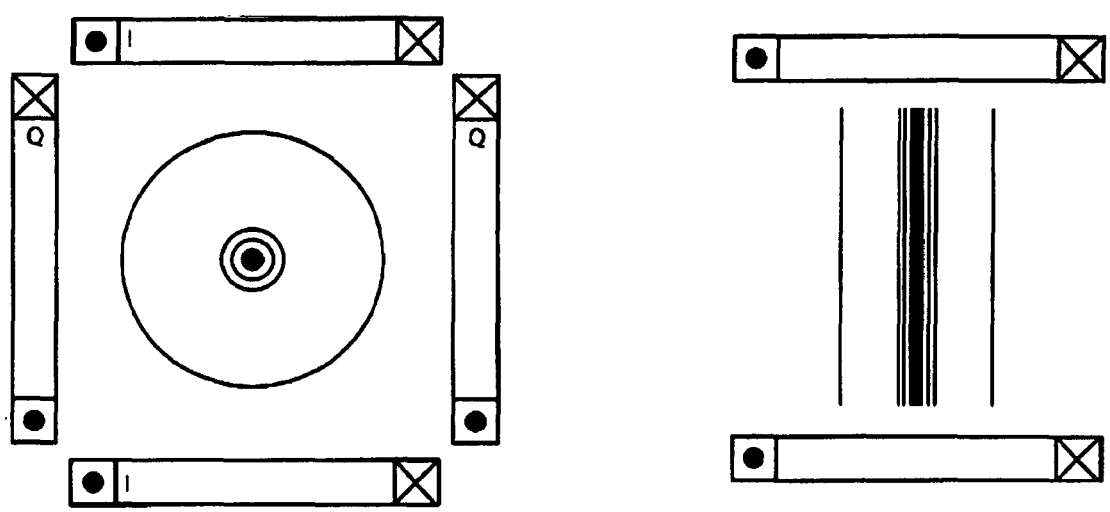
FIG. 3 shows examples of arrangements of drive or excitation coils that apply spatially homogenous fields to superpose spatially homogeneous fields with gradient fields according to some embodiments of the current invention.

FIG. 3 illustrates basic electromagnetic coil arrangements that may be used to translate or change the condition of an FFR. Multiple excitation sources, such as electromagnet coils, may be arranged to dynamically excite in any arbitrary direction. For example, coils may be arranged orthogonally in space and driven in quadrature as depicted in FIG. 3. These coils may also be arranged to excite along a direction of an FFR in which there is no substantial gradient, such as along the line of the FFL structure depicted in FIG. 3. In this case, the condition of the FFR structure is modified possibly without a distinct translation of the structure. The excitation coils as depicted in FIG. 3 are generally driven by sources configured to provide time-varying magnetic fields with spectral energy across a bandwidth. For example, the magnetic field can contain magnetic energy across a bandwidth of >10 Hz, >1 kHz, >10 kHz, or >than 100 kHz. In traditional MPI approaches, these excitation sources are comprised of one or a small number of sinusoidally varying components with low channel bandwidth (e.g. <1 kHz) centered at a carrier frequency (e.g. 20 kHz, 45 kHz, or 150 kHz). In pulsed MPI, these sources can produce waveforms with much broader bandwidth, and do not need to be centered at a carrier frequency.

Substantially Constant Pulsed Excitation Waveform Components

Figure 4:
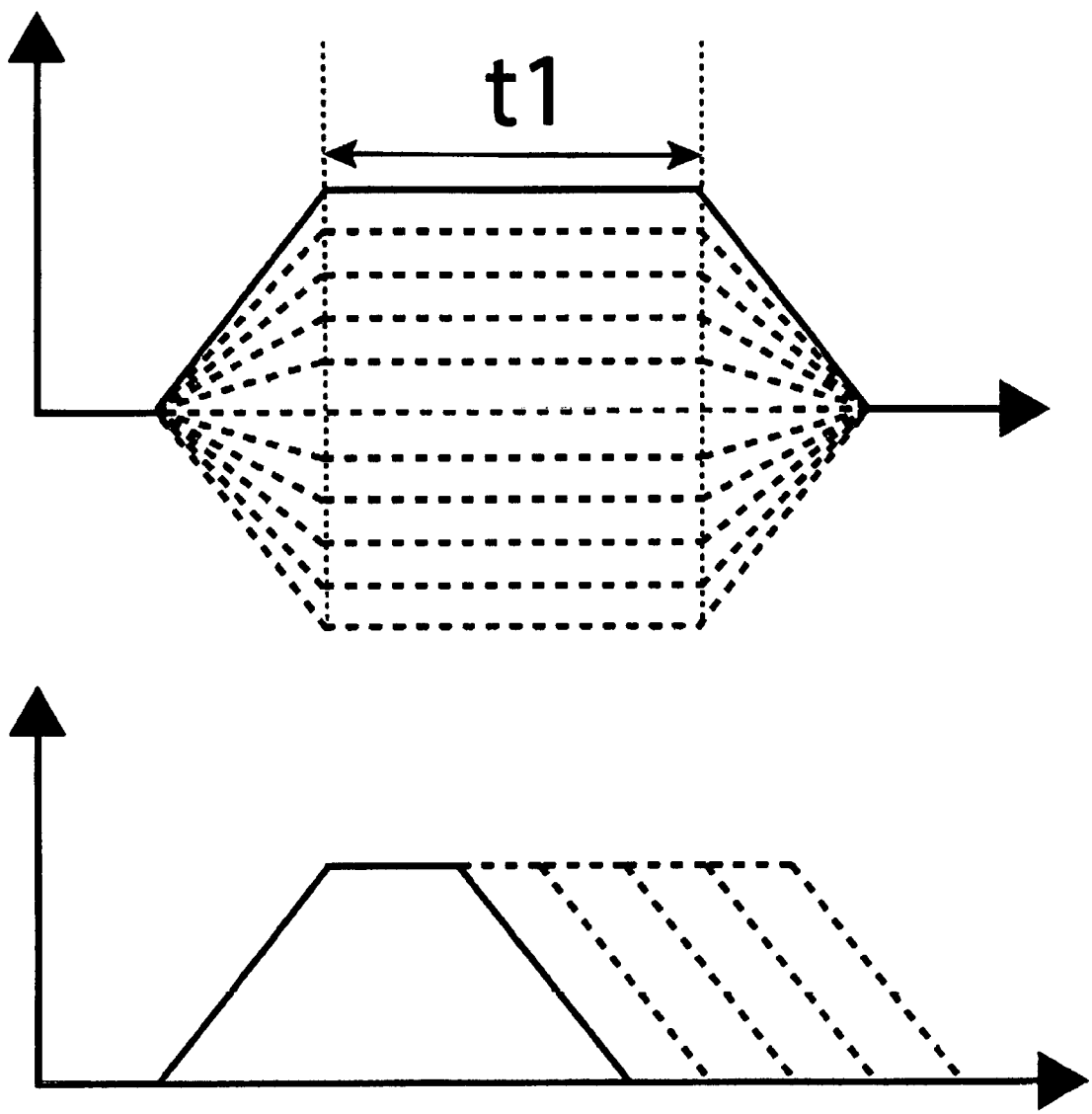
FIG. 4 shows examples of pulsed MPI waveforms that include substantially constant components with various durations (t1), amplitudes, and polarities according to some embodiments of the current invention.

Whereas a typical MPI trajectory includes a sinusoidally-varying and continuously transmitting excitation field (e.g., sinusoid at 45 kHz), some embodiments of the present invention provide for excitation waveforms with non-sinusoidal scanning trajectories. These waveforms are referred to herein as pulsed waveforms. A key feature of these pulsed excitation waveforms is the inclusion of some periodic or non-periodic components in which a magnitude of the field is held substantially constant for a period of time. By substantially constant, it is meant that the magnitude of the field, after some initial transient or ramping period and/or before a subsequent transient or ramping period, does not deviate from some desired or ideal field magnitude by more than a defined error. Example magnitudes of error include but are not limited to 10% of the desired value, 5% of the desired value, and 1% of the desired value. The period of time over which the field is maintained at this substantially constant value may range from 500 nanoseconds to 500 milliseconds; however, this range is not limiting. FIG. 4 illustrates substantially constant waveform components with varying amplitudes, polarities, and durations denoted by t1. In a total pulse sequence, many substantially constant waveform components may be used, with varying amplitudes, polarities, and t1 durations as indicated in FIG. 4.

Time Varying Pulsed Excitation Waveform Components

Figure 5:
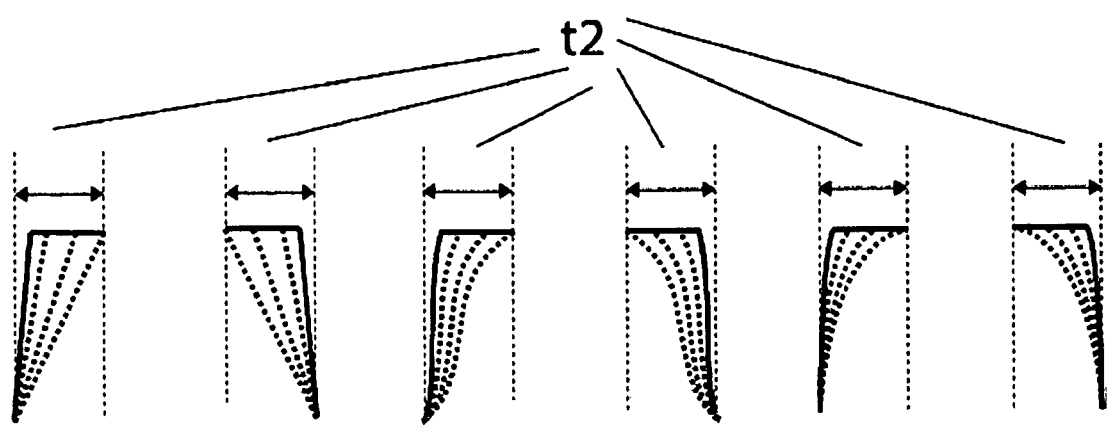
FIG. 5 shows examples of transient portions of pulses in pulsed MPI according to some embodiments of the current invention. These transient portions may occur fully within a rapidly transitioning window of time, t2. The dashed lines indicate variation in embodiments such that transient portions are characterized by any trajectory inside of a t2 threshold amount of time.
Figure 6:
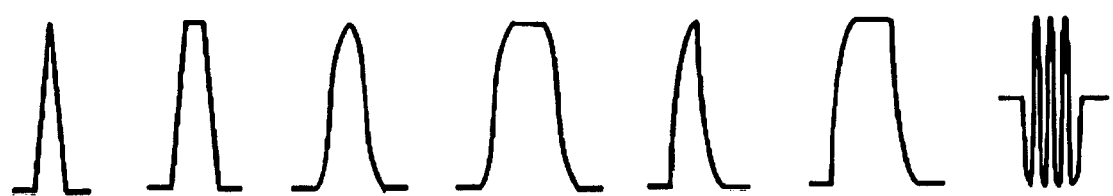
FIG. 6 shows examples of transient pulses used in pulsed MPI encoding according to some embodiments of the current invention. These transient portions may contain portions that occur within a rapidly transitioning window of time, portions that are substantially constant, or both.

Substantially constant values in the excitation waveform may be separated by pulsed waveform components of various shape primitives. In general, these primitives may be chained together with precise timing to create more complex pulsed waveforms. One important type of such a pulsed waveform primitive is one that rapidly transitions through rising and/or falling edges. During these rapid field transitions, the time varying field waveform may be of any shape. For example, the waveform may slew linearly, exponentially, sinusoidally, or superpositions thereof as illustrated in FIG. 5 and FIG. 6. FIG. 5 shows exemplary excitation waveforms illustrating rapid transitions through rising and/or falling edges, denoted by components with maximum duration t2. This duration t2 may be in the range of 100 nanoseconds to 10 microseconds. FIG. 5 also shows other exemplary transient pulses and pulse-like waveform components that may be used to build larger pulsed MPI waveforms or pulse sequences.

Magnetic Tracer

The magnetic tracers used in MPI are characterized by both their steady state response, frequently depicted as a M-H curve (FIG. 7), and their time-varying response to an applied magnetic field. We have found theoretically and experimentally the derivative of the magnetization curve, with respect to the applied field, is proportional to the ideal, native, or steady-state point-spread function (PSF) in MPI. This steady-state nanoparticle response gives the limit to the resolution possible in MPI, as traditionally understood, without the use of tools such as deconvolution. In practice, it can be difficult to achieve this resolution in canonical sinusoidal MPI because of dynamic magnetic relaxation behavior of tracers. Furthermore, as described herein, pulsed MPI methods can allow one to go beyond this previously considered limit and achieve better resolution than that predicted by steady-state Langevin theory, without deconvolution, by exploiting relaxation dynamics.

The time-varying response of magnetic nanoparticles to an applied magnetic field is governed by magnetic relaxation. Magnetic relaxation occurs because magnetic nanoparticles are not able to instantaneously respond to an applied magnetic field. In traditional sinusoidal approaches to MPI, when a characteristic time associated with a particle reorienting its magnetic moment is at a rate on the order of the period of the excitation sinusoid, the magnetic relaxation can cause a significant image blur. We can approximate this magnetic relaxation as a low pass filter applied to the time domain signal, which in turn manifests as an image domain blur. The result is an increase in the width of the point spread function from what would be predicted by the steady state Langevin M-H curve.

Larger particles can theoretically have improved steady-state resolution, depending on how the signal is acquired. It is well known that the Langevin equation describing tracer magnetization improves cubically with magnetic core diameter. This means that tracers with larger core sizes, such as larger than 25 nm, have steeper magnetization curves than tracers with smaller core sizes, e.g., smaller than 25 nm. However, with the typical amplitudes and frequencies used in traditional sinusoidal excitation MPI, magnetic relaxation in larger tracers, e.g., diameter greater than approximately 25 nm, can cause significant image blur that can preclude the use of the larger particles for high resolution imaging. Some embodiments of the current invention provide for methods and devices that use pulsed excitation waveforms that allow sampling of the steady-state magnetization for larger particles with relatively long magnetic response times without loss of resolution.

Components of a Pulse Sequence

Figure 8:
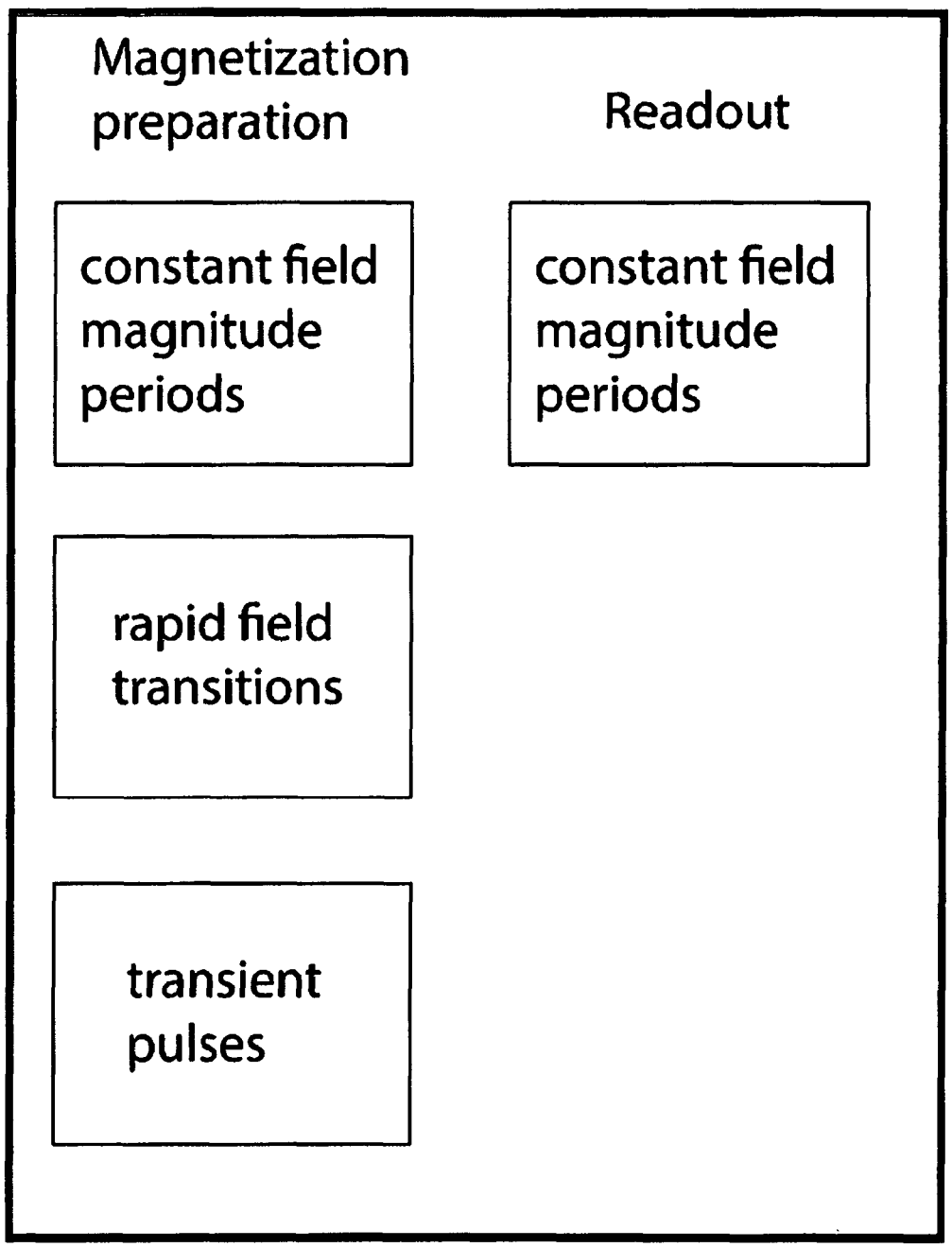
FIG. 8 is a block diagram of excitation pulse components according to some embodiments of the current invention.

Waveform primitives, such as transient pulses and periods that are substantially constant may be combined to create more complex pulsed waveforms and MPI excitation pulse sequences. Two basic components of a MPI pulse sequence may include one or more distinct magnetization preparation primitives and one or more distinct signal readout periods as illustrated conceptually in FIG. 8 and FIG. 9. In some embodiments, a series of magnetization preparatory pulses may be shorter in duration than a subsequent longer readout period. In some embodiments, the relative duration of preparation and readout periods may vary in successive sequences. In some embodiments, transitions between substantially constant periods serve as the excitation and/or preparation.

Substantially Constant Periods

Figure 11:
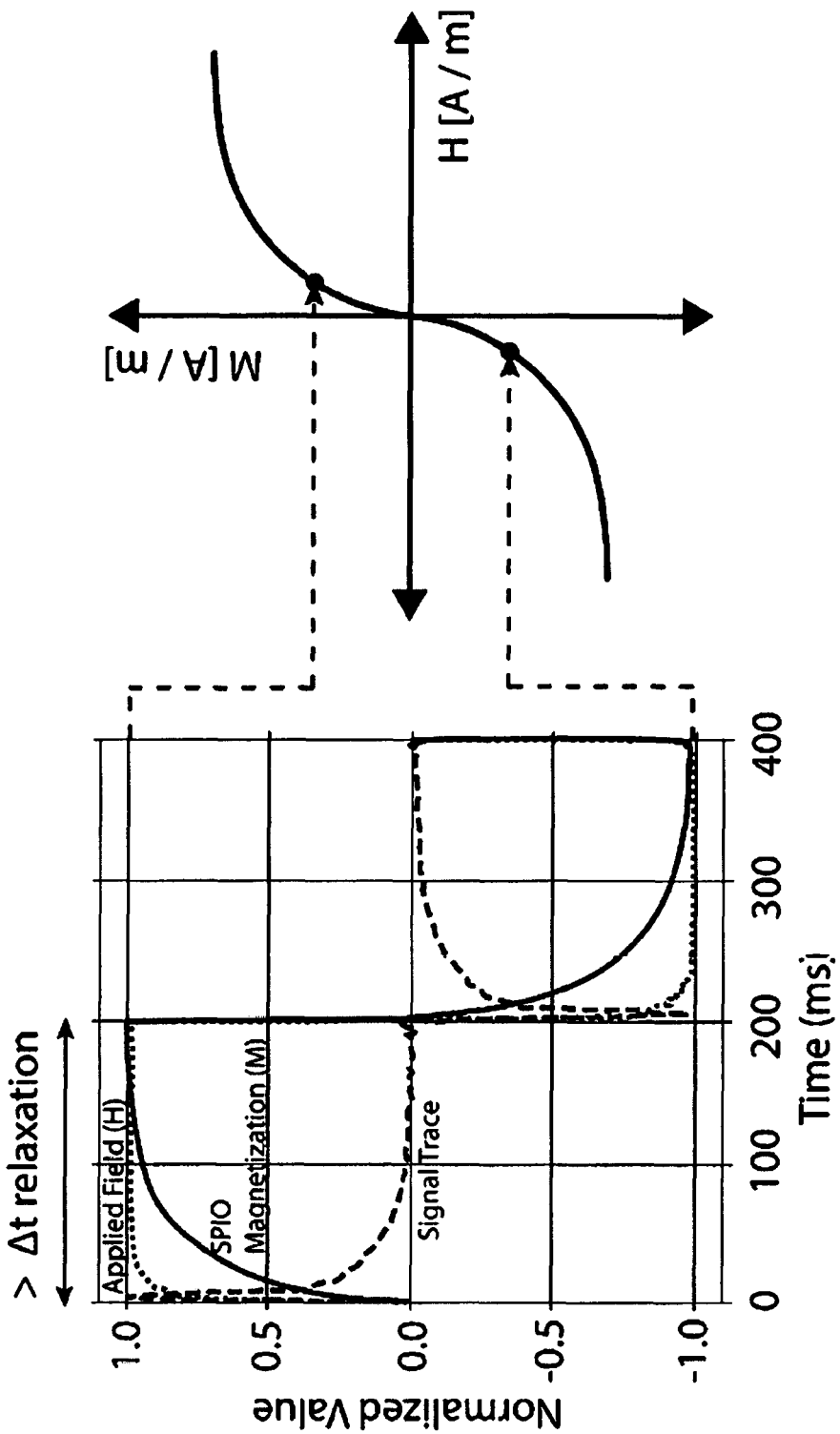
FIG. 11 shows experimental square wave time domain data and relation to steady-state M-H curve according to an embodiment of the current invention.

One or more periods where the magnetic field is kept substantially constant may be used both during magnetization preparation and during signal readout periods. During periods where the magnetic field is kept substantially constant, the magnetization of the tracer distribution evolves toward a new magnetization steady-state. This steady-state can be spatially varying because, for example, of the presence of an FFR and the interaction between the spatial field pattern it creates and filed-dependent tracer relaxation properties, and will evolve according to the magnetic relaxation physics governing the tracer. In general, the evolution of the magnetization is approximately step response-like, and so the inductively received signal records an impulse-like response. FIG. 11 shows exemplary data taken using a tabletop relaxometer system capable of producing pulsed excitation waveforms that are applied to a sample with no gradient present. Such a device is referred herein as an arbitrary waveform relaxometer (AWR). In FIG. 11, a square wave-like excitation pulse sequence generates a decaying impulse response signal in an inductive receiver coil. This corresponds to growths and decays in the magnetization as the sample distribution's net magnetization evolves toward the steady-state values associated with the total applied field state corresponding to each substantially constant value of the square wave. If the substantially constant period is of a sufficiently long duration, then steady-state is achieved and two distinct values of the tracer distribution's steady-state have been sampled, according to the steady-state M-H or Langevin curve associated with the tracer. FIG. 57 shows experimental data using square wave pulsed MPI with variable substantially constant hold times (or square wave half-period times). Hold times that are too short relative to tracer magnetic relaxation processes do not allow the tracer magnetization to achieve steady-state prior to the next transient pulse. This degrades both signal intensity and resolution as shown in FIG. 57. As the hold time increases from an insufficiently long hold time, an asymptotic approach to maximum signal and optimal resolution associated with steady-state can be observed.

Figure 56:
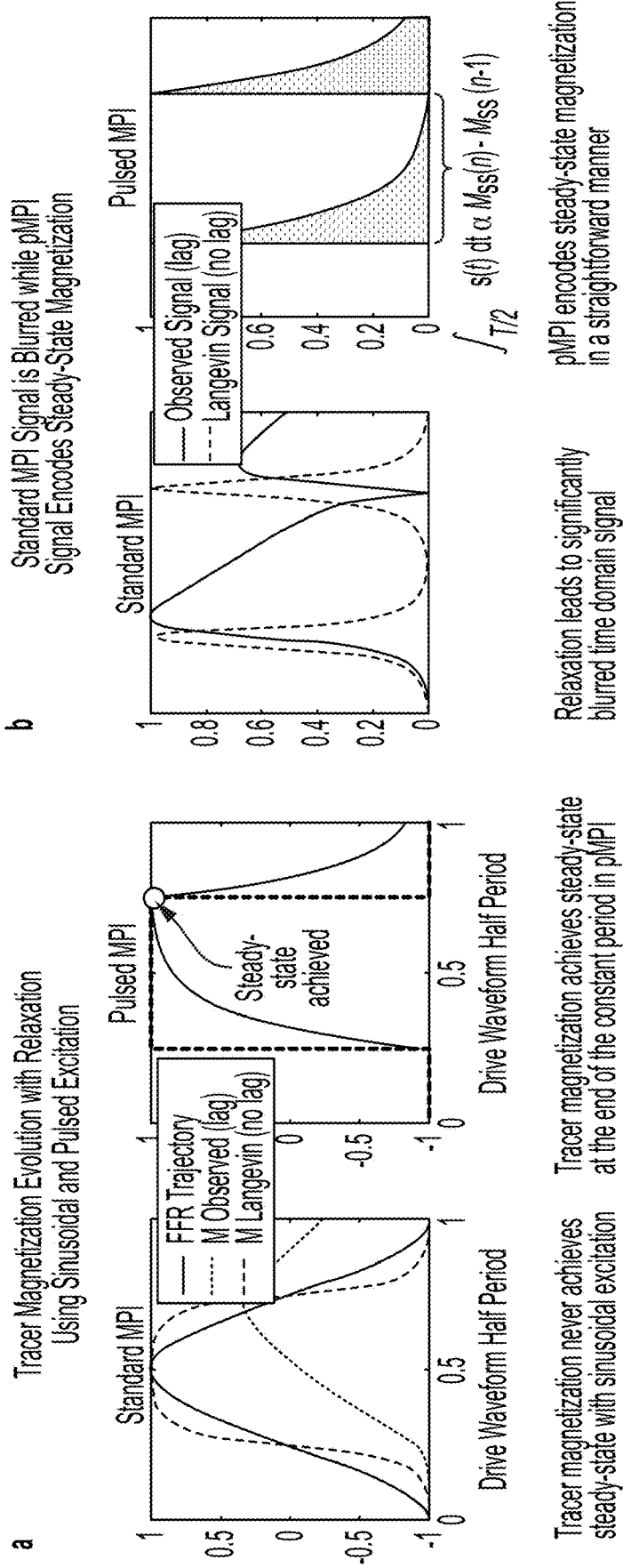
FIG. 56 is a depiction of how pulsed encoding captures relaxation dynamics in comparison with traditional sinusoidal methods, showing how pulsed MPI can capture steady-state magnetization information when sinusoidal excitation cannot.

FIG. 56 further illustrates the differences between sinusoidal and pulsed encoding, here considering a square wave excitation, in the presence of a tracer with non-trivial magnetic relaxation. With significant magnetic relaxation, the tracer magnetization significantly lags the excitation field in standard MPI, blurring the raw time domain signal significantly. In the pulsed MPI case, a sufficiently long substantially constant period allows steady-state magnetization to be achieved. With respect to an inductively received raw MPI signal, the integral of the raw time domain signal over the course of a single substantially constant component, or square wave half-period, is proportional to the difference between the steady-state magnetization values achieved at the end of the n-th and (n−1)-th substantially constant portions of the excitation square wave.

Temporal Relaxation Encoding by a Gradient Field

Figure 12:
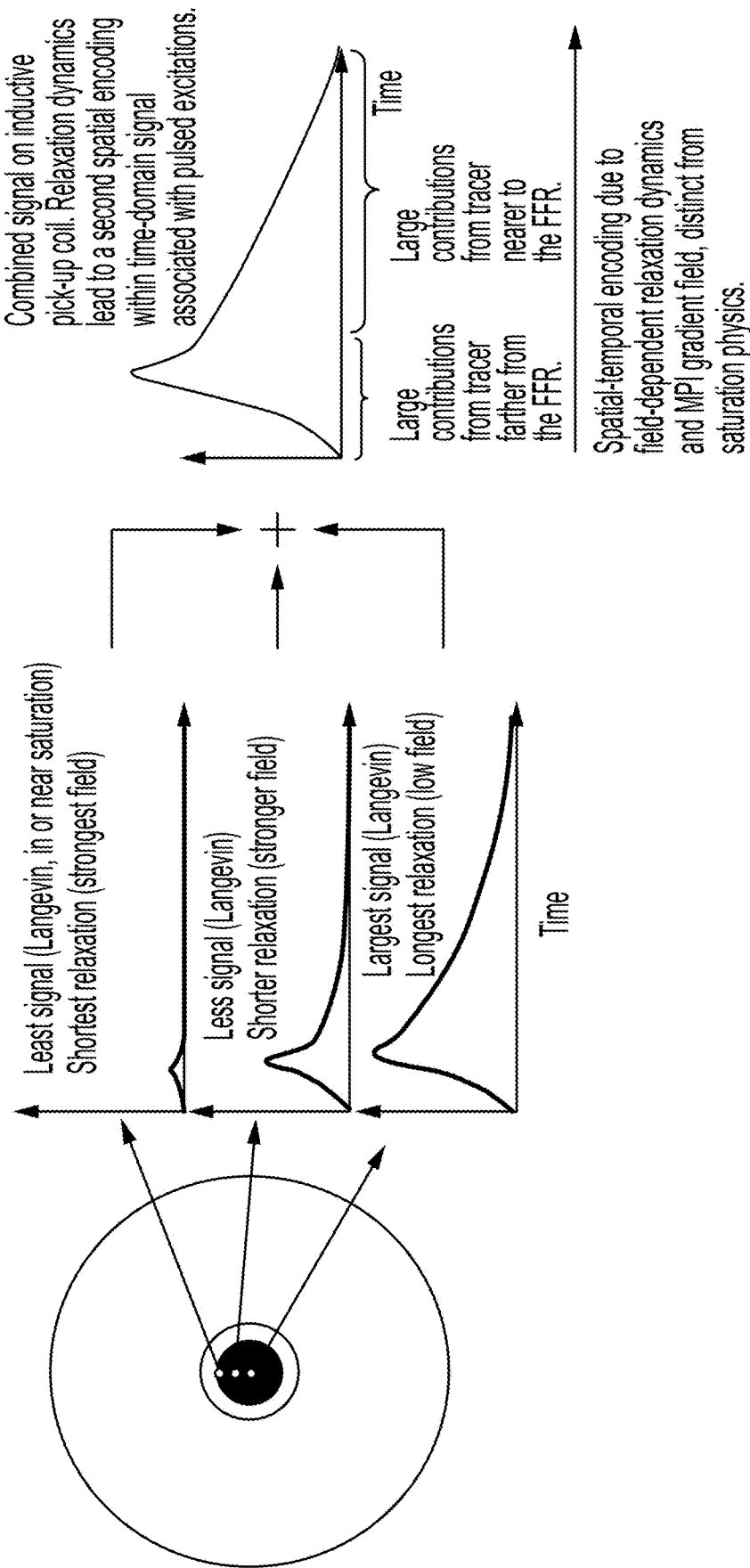
FIG. 12 shows temporal relaxation encoding in the presence of a gradient field according to an embodiment of the current invention.

If a gradient field or FFR structure is present during a substantially constant period of a pulsed waveform, this leads to a second encoding of spatial information related to the tracer distribution due to spatially-variant relaxation times. FIG. 12 illustrates how this spatial information is temporally encoded in the received signal associated with any substantially constant period in the presence of a spatially varying magnetic field such as an FFR. If a substantially constant period is applied with a duration that is sufficiently long, for example, much longer than the longest magnetic relaxation phenomena observed, then the entire tracer distribution evolves from one steady-state distribution to another steady-state distribution. Regardless of the exact duration of the substantially constant value and whether steady-state is achieved, however, the time-domain signal during the period encodes spatial information.

As FIG. 12 illustrates, tracer at any given location will evolve toward steady-state according to the magnetic relaxation response associated with the total applied field at that location. Because of the monotonic relationship between applied field magnitude and magnetic response time, generally, and across multiple physical mechanisms of magnetic relaxation, the result is that the time domain signal near the beginning of a substantially constant period is weighted more toward tracer located far from the fixed FFR isocenter (shorter relaxation times) while the signal at later time points or towards the end of the substantially constant period is dominated more by signal from tracer located closer to the FFR isocenter (longer relaxation times). The genesis of this temporo-spatial encoding is the monotonic relationship between the applied field and magnetic torque imposed on tracer at a given applied field. A high field magnitude, as experienced by tracer far from the FFR, imposes a very strong magnetic torque, leading to a faster response. This process will also lead to spatial encoding in the Fourier domain where the signal associated with tracer far from the FFR isocenter is composed of higher frequency components than the signal associated with tracer near the FFR isocenter. This separability in the Fourier domain can allow effective choice of receive bandwidth that limits noise and sharpens resolution. This second spatial encoding phenomenon occurs in tandem with the standard saturation-based spatial encoding underlying all MPI in which tracer farther away from the FFR isocenter will produce a smaller signal (smaller change in total magnetization and thus reduced signal energy) during a pulsed excitation regardless of the relaxation dynamics and according to the tracer's M-H or Langevin curve.

Figure 13:
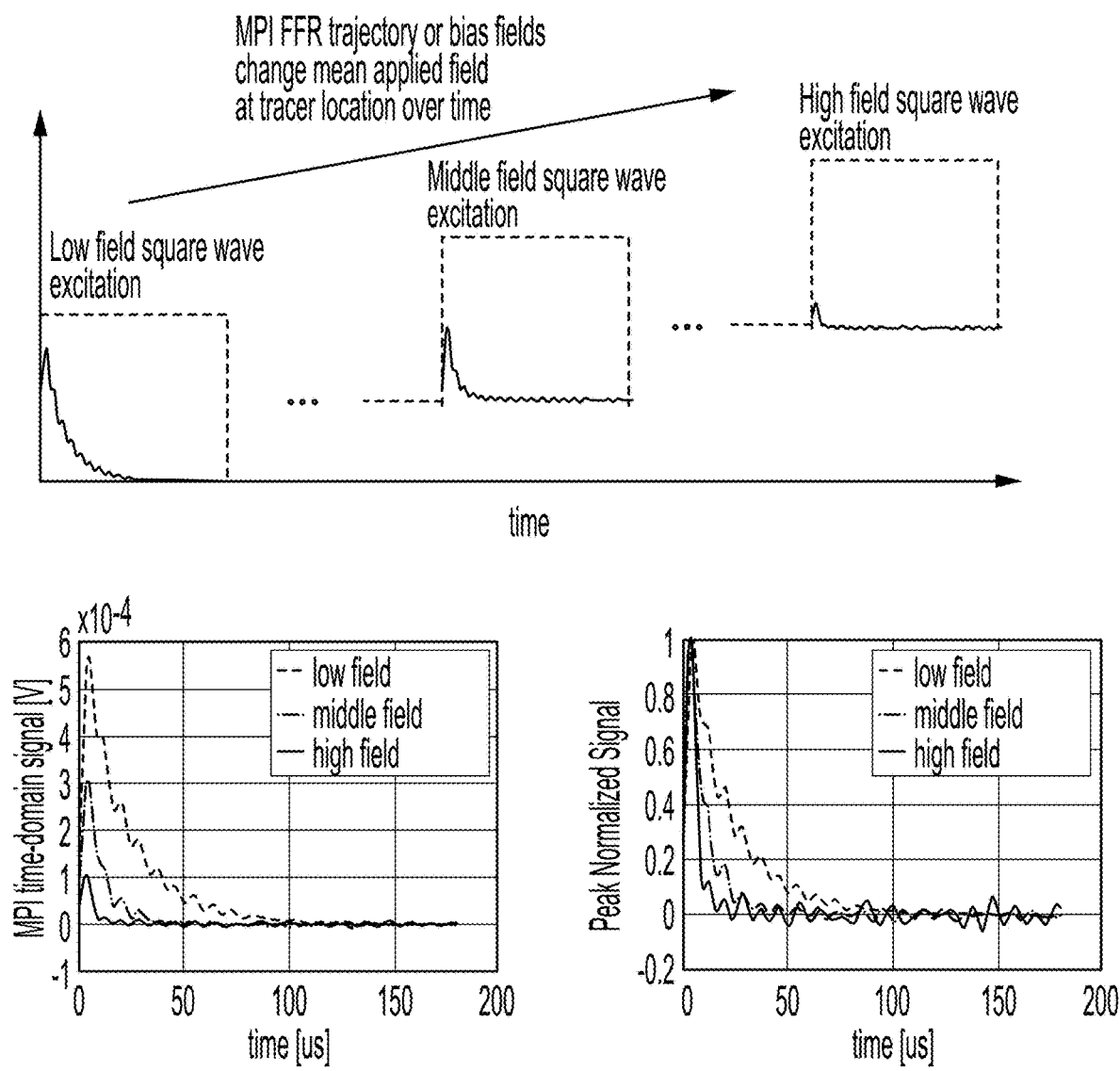
FIG. 13 shows AWR experimental data showing different time domain relaxation dynamics, and measured impulse responses as a function of total applied field according to an embodiment of the current invention.

This second temporal-spatial encoding phenomenon can be exploited both in a magnetization preparation aspect of a pulse sequence and during image reconstruction. FIG. 13 further illustrates how the total applied field influences both the total energy associated with the time domain signal during a substantially constant period (due to Langevin saturation effects) and the dynamics of the evolution of this signal (due to total field-dependent magnetization physics) in experimental data obtained with an AWR. In the AWR, the mean total field can be ramped or rastered over time while pulsed excitations are applied allowing for the querying of a tracer's signal and dynamics at various total applied field magnitudes.

Magnetization Preparation Periods

Figure 9:
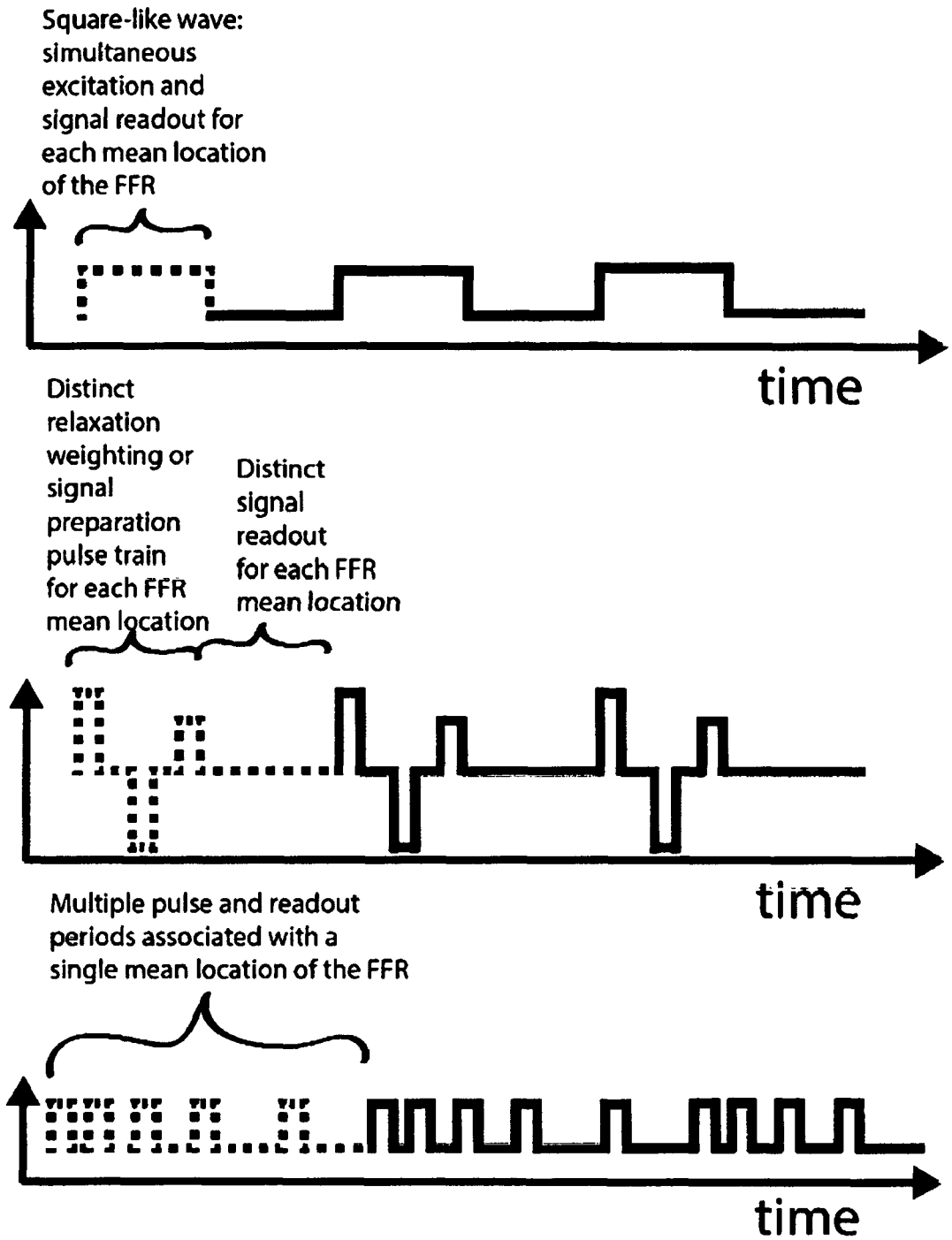
FIG. 9 shows a diagram of pulse waveform components according to some embodiments of the current invention.
Figure 10:
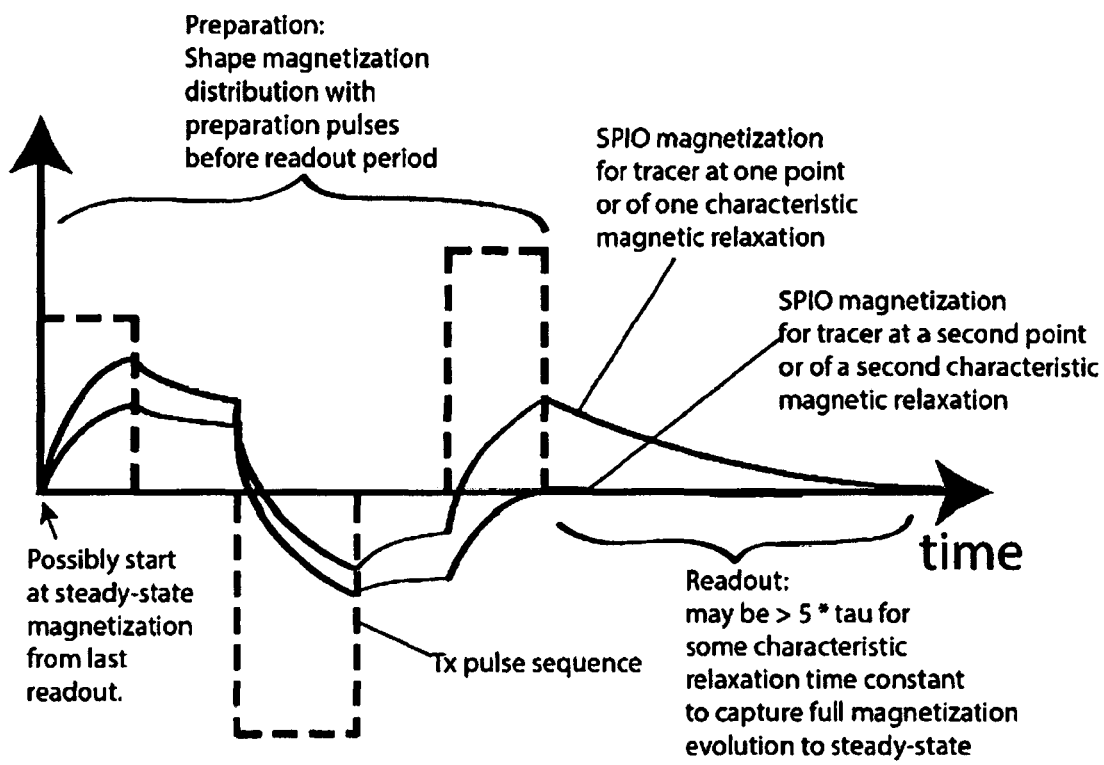
FIG. 10 is a specific pulsed waveform diagram showing selective nulling of tracer of a certain state according to an embodiment of the current invention.

One or more pulse components may prepare, setup, or otherwise dynamically shape the magnetization state of a tracer distribution prior to, or possibly simultaneous with, a readout period. FIG. 9 and FIG. 10 show some exemplary pulses and sequential collections of pulses that may be used in such a preparatory period. These pulses may be of sufficiently short duration to take advantage of spatially dependent magnetic relaxation dynamics in the tracer distribution. For example, a series of pulses in a preparation period may be of sufficiently short duration as to prevent steady-state magnetization achievement anywhere in the non-saturating region. However, the degree of change or growth in magnetization in this pulsing period will spatially depend on the precise trajectory of the FFR structure. In general, relaxation dynamics are slowest closer to the FFR isocenter due to the monotonic decrease of magnetic relaxation time with distance from the FFR (due to a monotonic relationship between relaxation time and total applied field strength) and fastest further from the FFR isocenter. In this manner, the signal in the readout periods can be pre-weighted by prior manipulation of the distribution in the preparation period.

FIG. 10 generically illustrates an exemplary pulse sequence consisting of a magnetization preparation sequence of pulses followed by a substantially constant readout period. The evolution of tracer located at two different locations and/or with two different intrinsic magnetic relaxation response times are shown. The preparatory components differently shape the magnetization of tracer at these two points (location or relaxation state) because of either their differing geometry with respect to the FFR, intrinsic magnetic relaxation differences, or both. In particular, it may be possible to attenuate, null, or cancel tracer with certain properties but not others with this approach, leading to MPI relaxation weighted encoding and inversion recovery and nulling sequences. Magnetization at only two locations and/or the same location but with two different relaxation response profiles are shown for illustrative purposes; in general, these magnetization preparation pulses will affect the tracer in the saturating region in a continuously varying manner over the spatial coordinates.

Readout During Magnetization Evolution

A general feature of pulsed waveforms is the possibility to define distinct signal readout periods, for example, subsequent to magnetization preparation periods. In some embodiments, a readout period will be comprised of a substantially constant period in which the evolution of the magnetization of a tracer distribution moving toward a steady-state position is observed. In some embodiments, this readout may immediately follow a rapidly transitioning rising and/or falling edge. In some embodiments, the temporal duration of a substantially constant readout period will be purposely designed to ensure the achievement of magnetic steady-state of the tracer distribution in a sample of interest. In other embodiments, a substantially constant readout period will be purposely designed not to achieve steady-state conditions. In some embodiments, a readout period may also include non-constant components. FIG. 9, FIG. 10, FIG. 11, FIG. 12, and FIG. 13 demonstrate exemplary readout periods in pulsed MPI excitation waveforms.

Pulse Types in MPI

Pulsed waveforms may be used to drive homogeneous excitation coils in MPI. These pulsed waveforms will affect the state and/or location of the FFR and generate signal in the presence of a magnetic tracer distribution.

Projective Excitation by Translation of an FFR.

Figure 14:
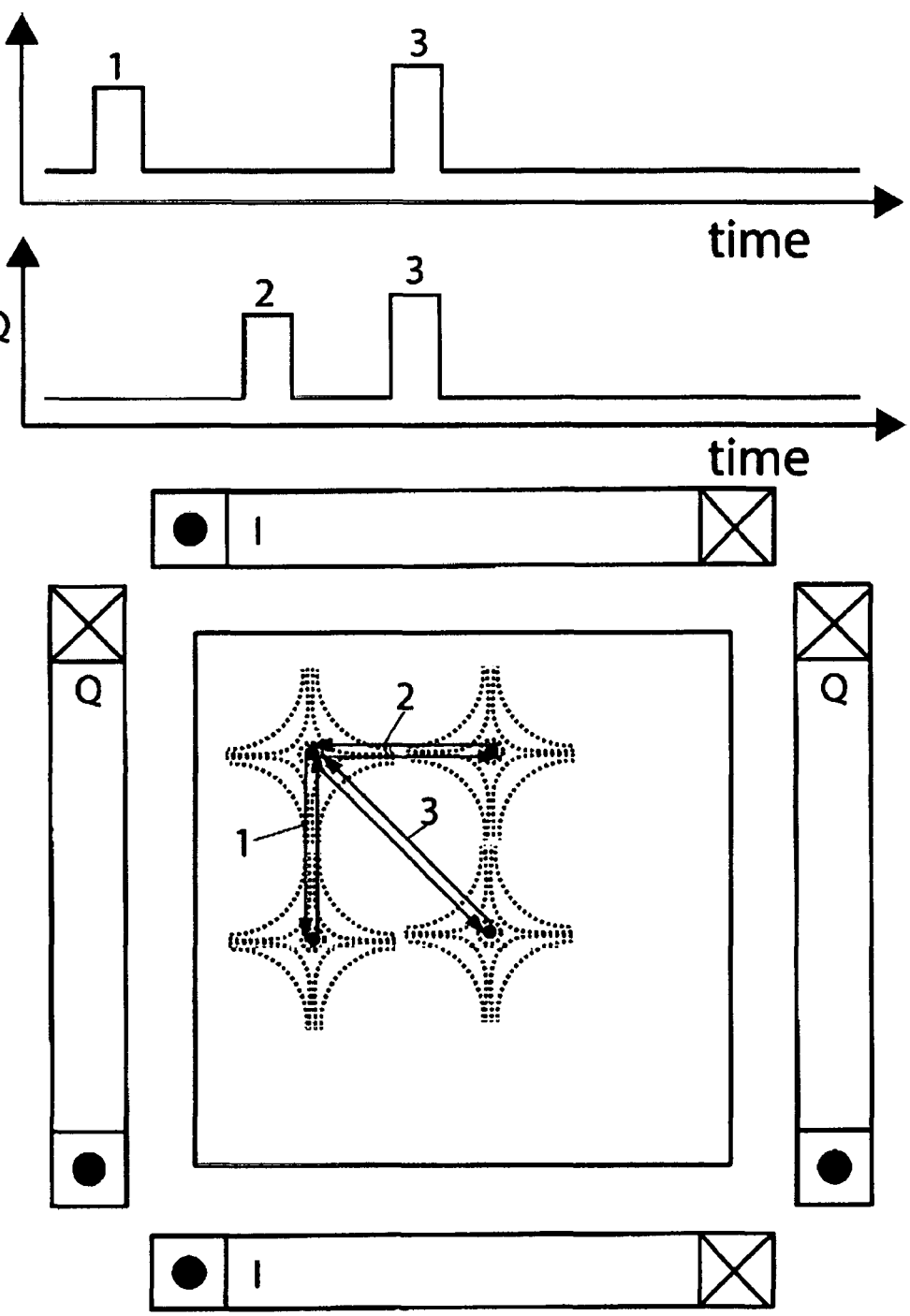
FIG. 14 shows an example of FFR translation with a series of pulses driving excitation coils in quadrature arrangement according to an embodiment of the current invention.

In some embodiments, pulsed waveforms will be applied by homogenous coils such that the effect of pulses is to translate the location of the FFR structure. During substantially constant periods of these waveforms, the FFR structure is stationary in the FOV. FIG. 14 illustrates how pulses in orthogonal homogenous coils act to translate the location of an FFR anywhere in the plane defined by the principal axes of the two excitation coils. For FFR structures with an isocenter localized in all three dimensions, such as an FFP, homogeneous coils can be used to translate the FFR structure in any direction. Any tracer along the curve connecting sequential locations of the FFR isocenter, for example lines 1, 2, and 3 in FIG. 14, will be excited by the pulse. The trajectory may be of a more general shape than a simple line, and the magnetic relaxation governing the tracer signal will generally depend on this trajectory and the instantaneous relative geometry between the location of the FFR and the tracer distribution. In the case of a simple square-like pulse, each step-like transition defines a line in x-space that connects the initial location of the FFR isocenter and the location after the step. Tracer located near the excitation line close to the initial FFR location will respond more quickly than tracer located near the excitation line close to the final FFR location for the duration of the pulse.

If two substantially constant components bracket an arbitrary dynamic trajectory, and the duration of both substantially constant periods is sufficient to establish steady-state magnetization conditions for the relative geometry between the FFR and tracer distribution associated with each substantially constant component (and there is no change in the tracer distribution in the intervening time period), then an initial magnetization state and final magnetization state are sampled without dependence on the particular intermediate trajectory. The instantaneous time-domain received signal, which measures the time derivative of the magnetization evolution, will depend on the specific trajectory chosen, but the integral of this signal may not. In this case, where the duration of the bracketing substantially constant components exceeds the time required for all magnetic relaxation phenomena to complete, then the signal may be viewed as encoding a full local projection in space along or near the line connecting the initial and final FFR locations. If steady-state is not established at one or another of the bracketing substantially constant periods, then this result will not apply: The difference in magnetization between the two components will be weighted by aspects of the specific trajectory.

Excitation in the Direction of an FFL

Figure 15:
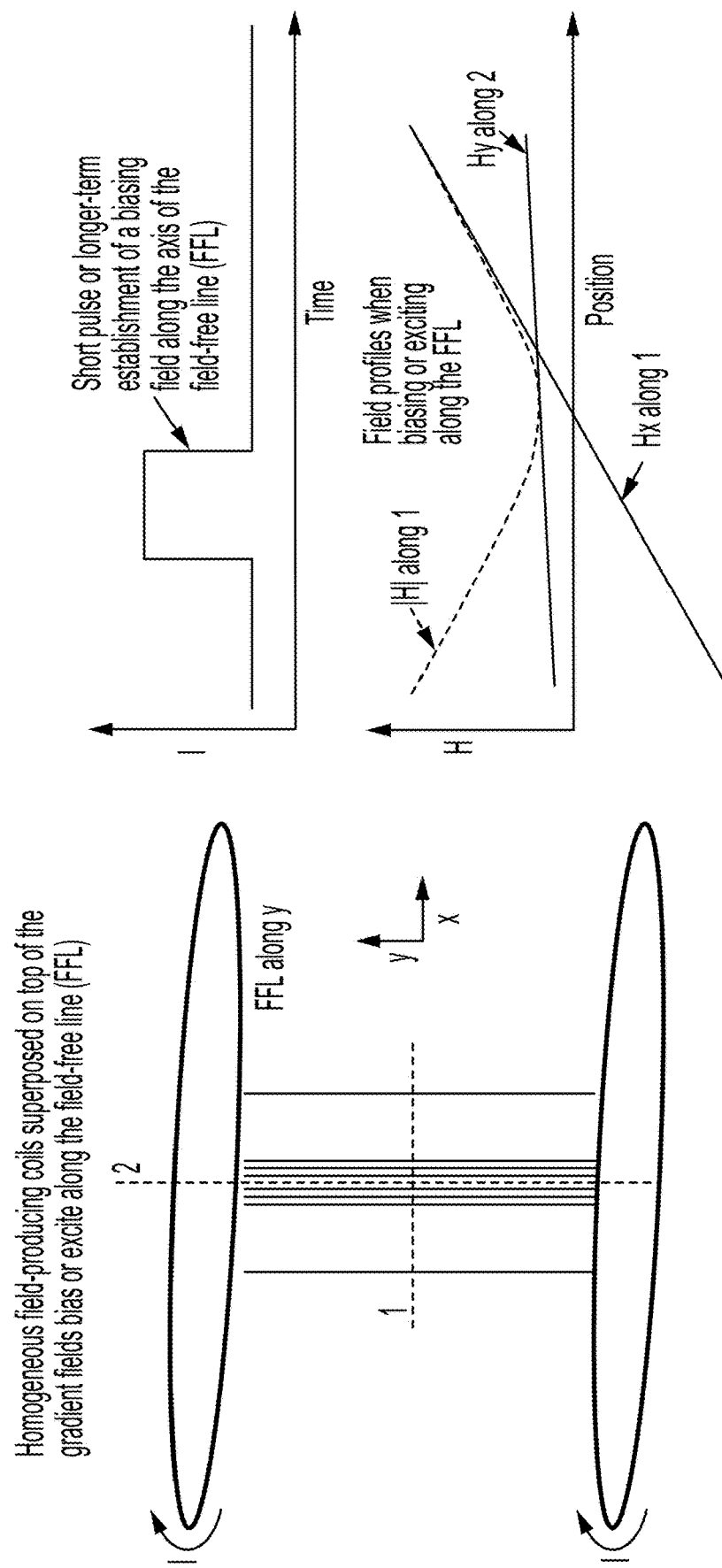
FIG. 15 shows x-space consequences of excitation in the direction of an FFL according to an embodiment of the current invention. This creates a low-field line (LFL) in which the FFL shape and spatial structure is maintained, but in which the line of symmetry does not pass through 0 field (it is biased at some field magnitude). Pulsed excitation along the line, biasing of the line with orthogonal excitation, or both may be performed.

In some embodiments, excitation pulses may be applied in the direction along the line of a field-free line (FFL). As illustrated in FIG. 15, the condition of the gradient field structure is modified, but the location of the structure does not change in the plane orthogonal to the line during the pulse applied in the line direction. The FFL does transition from an FFL to a low-field line (LFL), from an LFL to an FFL, or an LFL polarized in one direction to an LFL polarized in the opposite direction depending on the value of the field immediately prior to the application of the excitation pulse. An LFL may be characterized by the same or similar spatially varying structure but biased in magnitude such that there is no point or points that cross through a zero field magnitude. The vector direction of the field will rotate from one side of the plane orthogonal to the LFL to the other, as in the case of the FFL. In this excitation regime, all tracer along the line defining the FFL or LFL will be excited in the same manner and subject to the same relaxation physics in terms of the dependence on the total applied field, and this represents a full FOV projection encoding along the line but with no projective excitation in the orthogonal plane. Excitation pulses along the line may be performed in parallel or in series with excitation pulses in the plane orthogonal to the line.

Biasing of an FFL

In some embodiments, a homogeneous bias field in the direction of an FFL may be applied generally with distinct excitation pulses applied separately, for example, in the orthogonal plane, along the line, or both. Such a bias field establishes an LFL in place of an FFL. FIG. 15 illustrates an LFL with a biasing waveform. The addition of a biasing field may serve to break the symmetry of rotation of tracer aggregates when the LFL is moved in the orthogonal plane and because tracers are not excited by a zero field region at any point, more rapid relaxation dynamics may be induced generally for more SNR efficient signal encoding.

Pulsed Excitation Without an FFR

In some embodiments, homogeneous pulsed excitation waveforms will be applied to a sample without the presence of gradient fields or a spatially varying FFR structure. In this regime, a linear biasing field may be slowly ramped which will take the entire sample through a trajectory in the applied field magnitude space that is linearly proportional to the experience of a point source in a scanning system when linear gradient fields are used. Such a system can be used to rapidly test the effect of MPI pulse sequences and measure the one-dimensional (1D) PSFs associated with a tracer sample or sample object in aggregate. Note that such an approach excites all tracer, regardless of location, in the same manner. Thus the 1D PSF describes the aggregate or average behavior of all of the tracer in the observation volume. This type of scan can be accomplished with small tabletop relaxometer systems such as an arbitrary waveform relaxometer (AWR) or with a full imaging scanner if the magnetic sources that generate the FFR can be turned off.

Because sampling is only in one dimension—the applied magnetic field space—these spatially homogeneous scans are high throughput and, for example, may be completed in less than one second. A slew of scans testing different pulse sequence parameters or entirely different pulse sequences may easily be tested and vetted. Such scans can also quickly provide representative information about the entire tracer distribution in a sample, in terms of resolution, total tracer mass and SNR, and magnetic relaxation dynamics. This information may be used to guide choice of scan parameters such as the amplitude and period of substantially constant field values during a subsequent and generally longer imaging scan or series of scans. Moreover, this information may also be useful in choosing signal processing and reconstruction parameters such as the receive bandwidth and receive filter cutoffs. These values may be obtained through a standardized calibration procedure or on the fly before any scan using a fast gradient-less scan.

Figure 16:
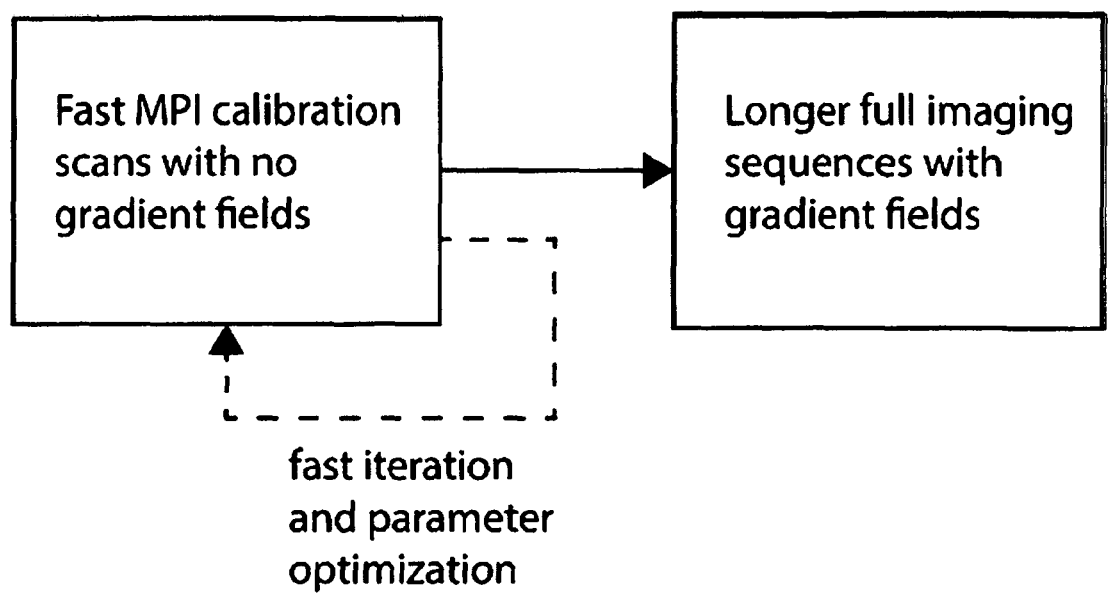
FIG. 16 shows parameter optimization using fast gradient-less scans before imaging scans according to an embodiment of the current invention.

FIG. 16 illustrates a pulsed MPI scanning workflow in which one or more fast scans without gradient fields are used to optimize pulse sequence parameters prior to the initiation of longer imaging scans using the gradient fields.

Pulse Sequences

Figure 17:
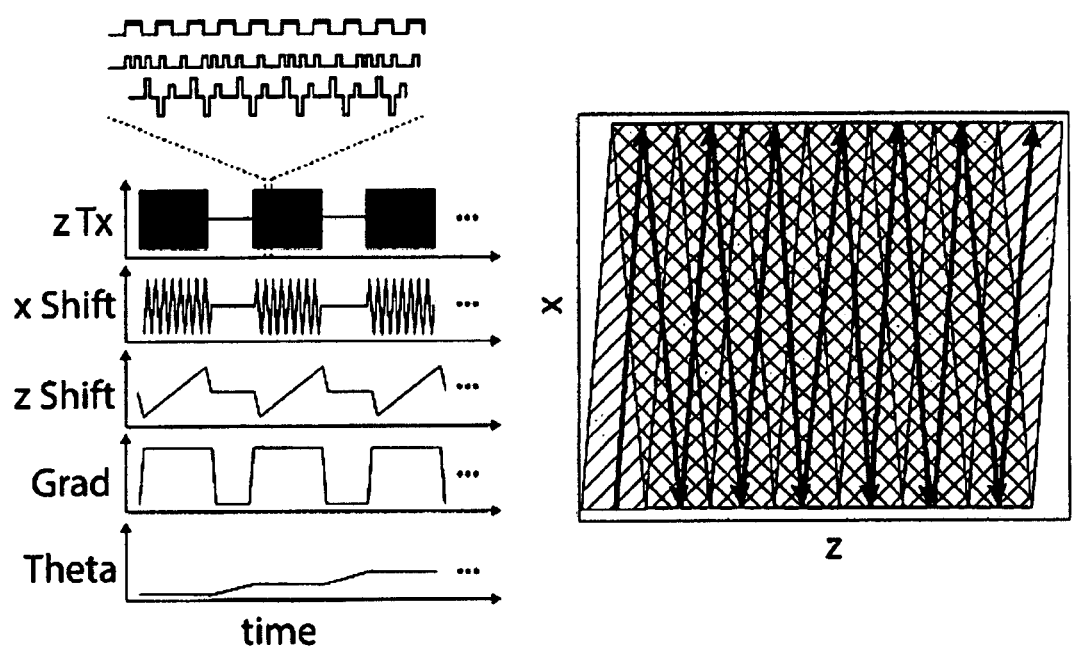
FIG. 17 shows an example of an x-space pulsed MPI pulse sequence and FFL trajectory diagram in which multiple 2D projection data sets are obtained with an FFL according to an embodiment of the current invention. The multiplicity of 2D projection data sets at different projection angles contains the information needed to reconstruct 3D tomographic images.
Figure 55:
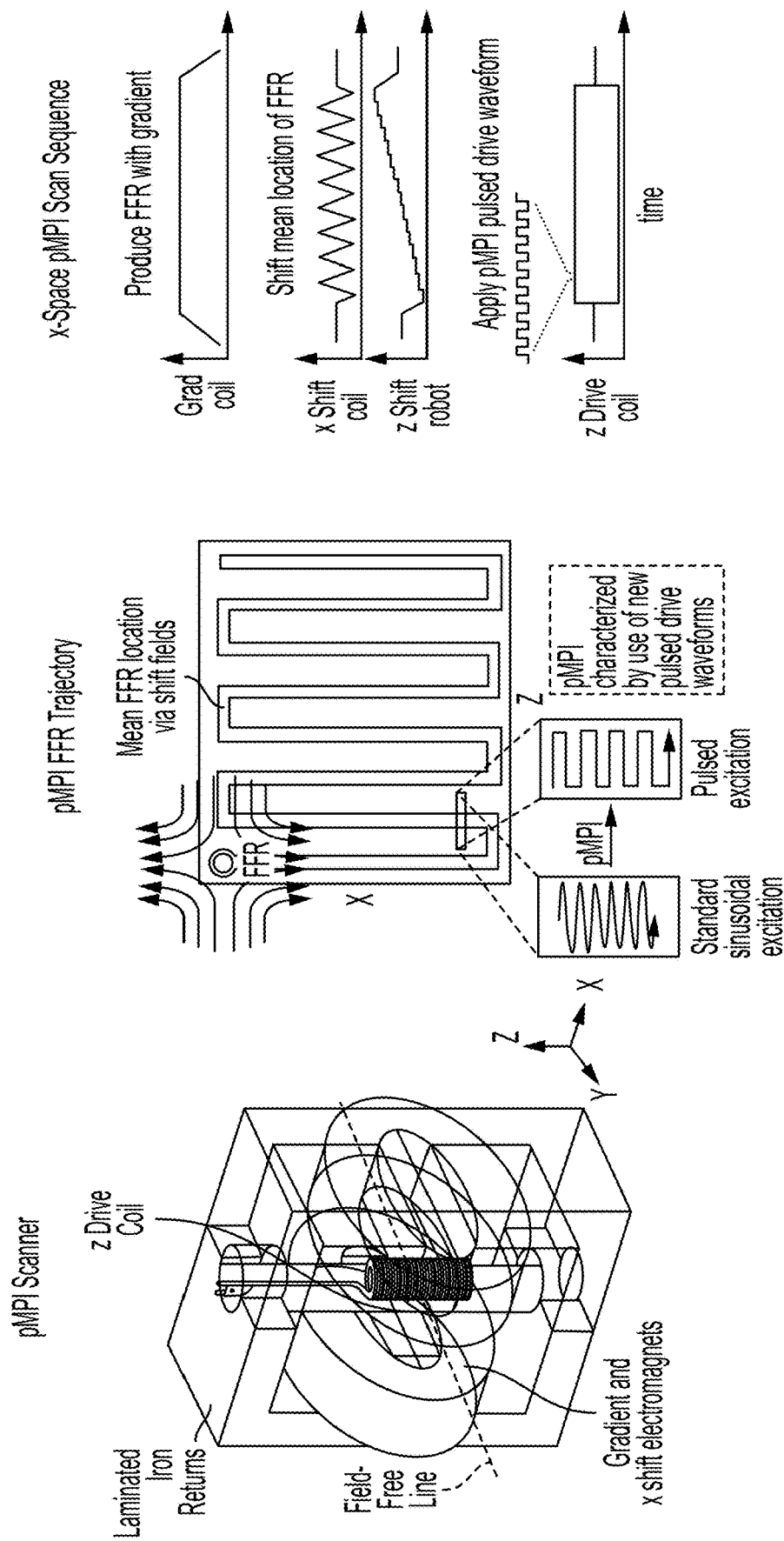
FIG. 55 is a schematic illustration of pulsed encoding in MPI acquisition with a field-free line scanner according to an embodiment of the current invention.

The encoding machinery available in pulsed MPI, including various pulse types, conceptual pulse waveform components, and coil arrangements driven by the pulsed waveforms can be combined to create complete pulsed MPI pulse sequences to fully sample an imaging FOV. An exemplary pulsed MPI pulse sequence diagram is illustrated in FIGS. 17 and 55, showing exemplary pulsed excitation waveforms in context with other system sequences. In these embodiments, one or more pulse sequences are used to fully sample 2D slices using an FFL scanning system; multiple slices with rotated geometries between the sample and FFL are sampled to enable tomographic 3D image formation using projection reconstruction techniques. Aside from the relatively fast pulsed excitations, slower shifting components allow sampling of the entire 2D FOV as illustrated in an exemplary raster scanning trajectory depicted in FIG. 18. In some embodiments, an excitation pulsed waveform containing one or more magnetization preparation components and one or more distinct readout periods may be repeated many times, with each repetition associated with a distinct mean location of the FFR structure defined by more slowly-varying shift waveforms. In general, the much slower slew rates associated with the slow shift components will not violate the substantially constant criteria (e.g., 1% or 10% of the desired value, etc.) imposed on substantially constant field periods in the excitation waveforms. In some embodiments this violation may be allowed or desired.

Some exemplary pulse sequences are described herein, including square wave-like pulse sequences, steady-state recovery sequences, and an illustrative more complex SNR efficient sequence. Neither the discussion of these specific pulse sequence embodiments nor the exemplary forms of these pulse sequences illustrated are to be taken as limiting.

Square Wave-Like Excitation Pulse Sequences

One pulsed MPI pulse sequence that illustrates many of the benefits of encoding the MPI signal with pulsed waveforms is the use of square wave-like excitation waveforms. These waveforms contain alternating periods of a substantially constant value of the magnetic field separated by rapid transitions through rising and falling edges. These components are depicted in FIG. 4, FIG. 5, and FIG. 6. The term square wave-like is used to emphasize that the overall shape of repeating excitation pulse components may resemble a square, may be trapezoidal, or may be more complex, such as containing exponentially or sinusoidally varying components, as long as the periods of rapid transitions and substantially constant values have the properties previously described. A square wave-like excitation pulse sequence so defined may be considered to have a minimal magnetization preparation period. A previous substantially constant readout period prepares the magnetization in a particular state and the rapid transition to the next substantially constant readout period provides the signal generating impetus where the second substantially constant readout period establishes the steady-state target to which the magnetization distribution evolves toward during readout.

Figure 58:
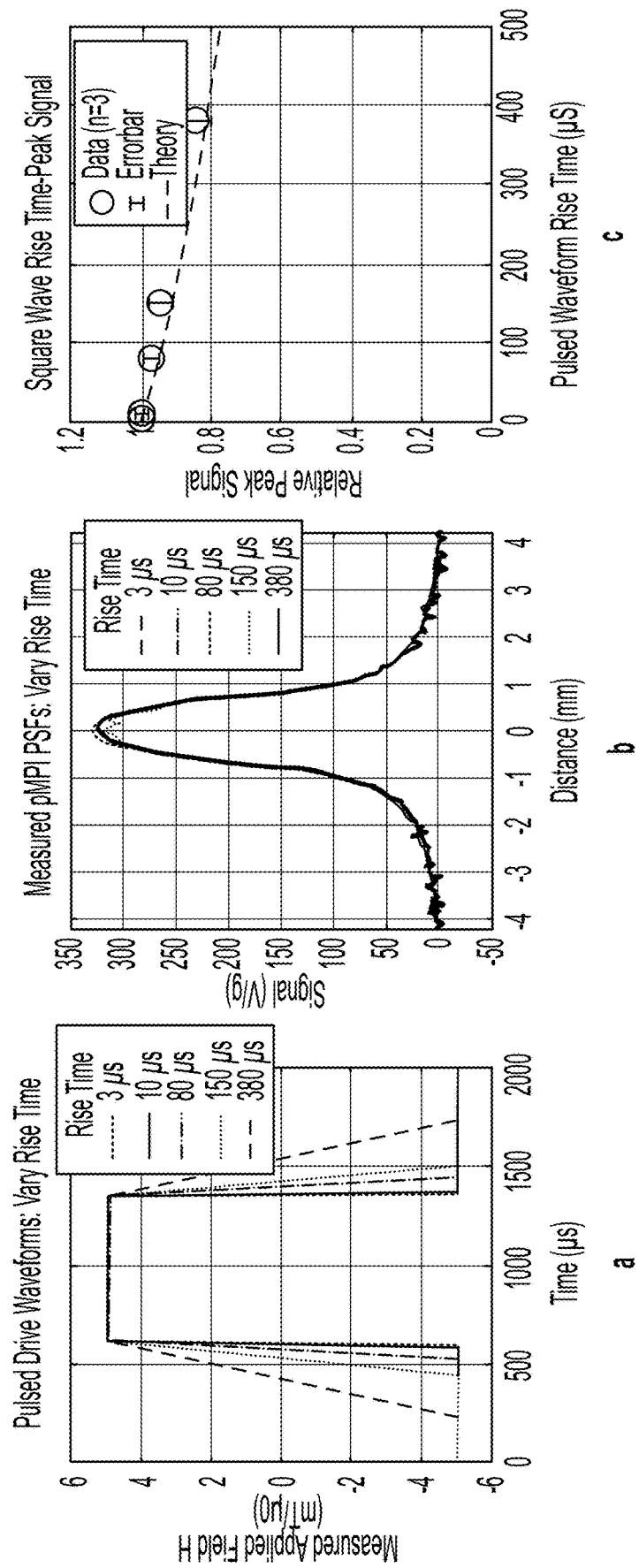
FIG. 58 shows experimental data showing the effect of varying rise time of dynamic/transient regions of excitation used in between substantially constant hold times in pulsed MPI excitation. For example, this indicates the effect of using an overtly trapezoidal waveform versus something close to an ideal square waveform in pulsed excitation.
Figure 59:
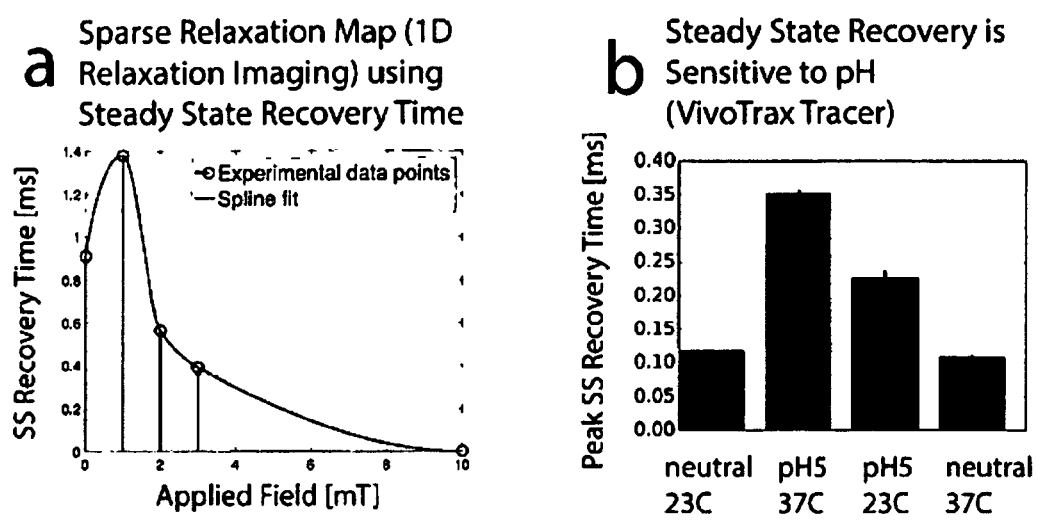
FIG. 59 shows exemplary experimental data using a steady-state recovery pulse sequence to produce a 1D relaxation image and to detect changes in the dynamic relaxation behavior of a tracer as a function of pH according to an embodiment of the current invention.

FIG. 58 shows experimental data showing the ramifications of transitioning from a more square wave-like to trapezoidal waveform in the context of a substantially constant hold time that is adequate to achieve steady-state magnetization for each excitation half-period. In this regime, the PSFs obtained from a sample when varying the trapezoidal rise time from 3 microseconds to 380 seconds are almost identical. The key to this performance is that the substantially constant hold time is the same and sufficient to induce steady-state. The effects of increasing rise time, in this case, are to reduce SNR efficiency and peak signal (more trapezoidal waveforms impose less of a peak magnetic torque or induce less of a peak dM/dt) and to reduce temporal decoupling between excitation feedthrough and the tracer signal.

Figure 19:
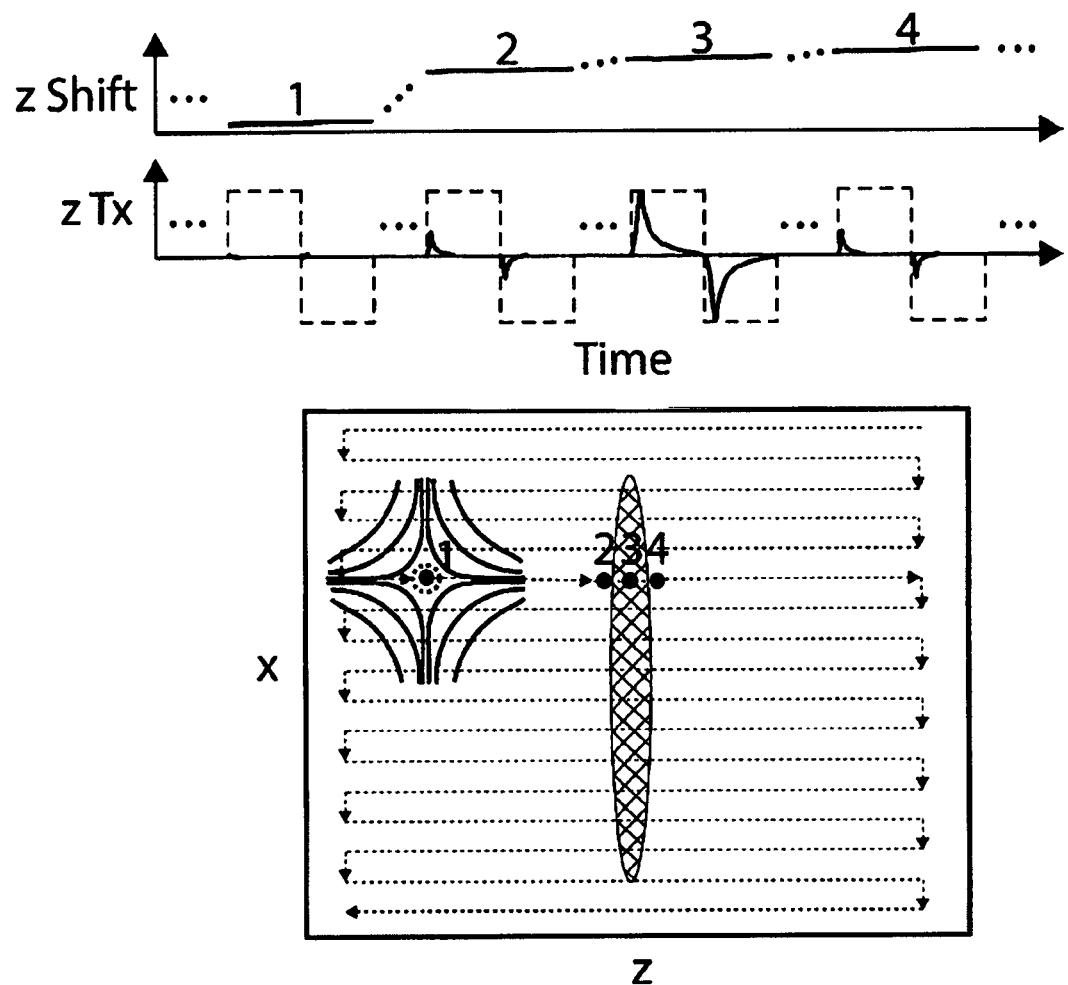
FIG. 19 shows a square wave pulse sequence sampling an ellipsoidal tracer distribution and trajectory of mean location of the FFR in space according to an embodiment of the current invention.

FIG. 19 shows an exemplary square wave-like sampling of a 2D FOV. As illustrated, the FFR is rastered across the image over time while a square wave-like excitation rapidly repeats. Examples of the received signal from receiver coils during alternating square wave half-periods at different mean locations of the FFR isocenter are illustrated. Only when the mean location of the FFR isocenter, as established by slowly varying shift waveforms, is near or coincident with the depicted ellipsoidal tracer phantom is a significant time domain response observed.

If the half-period of the square wave-like excitation waveform is greater than or equal to the magnetic relaxation or magnetic response time of the tracer distribution, then the tracer distribution will reach a steady-state in magnetization by the end of each square wave half-period. Here, the magnetic relaxation time or magnetic response time refers to the amount of time required for the magnetic response of the tracers to settle to a steady-state after each step-like transition of the square wave-like waveform. This time may be precisely defined in various ways. For example, if the magnetic impulse response of a tracer can be described adequately as one or more exponential time constants, then the response time may be defined as greater than or equal to some multiple of the largest or maximum time constant. For example: tchar*2, tchar*3, tchar*4, or tchar*5 where tchar is a mean, bounding, maximum, or characteristic exponential time constant. The experimental data of FIG. 57 show that even without knowledge of a tracer's characteristic time constant from first principles, the required square wave half-period (substantially constant hold time) can be obtained by varying the half-period and identifying asymptotic stabilization of peak signal intensity and/or resolution. In some embodiments, a tchar that is not necessarily the maximum associated with a heterogenous process may be used to define the target for steady-state or approximate steady-state establishment in a pulsed MPI signal encoding sequence.

Tracer magnetic response times are generally a function of the absolute magnetic field experienced by the tracer such that the zero field time constant is the longest, with a monotonic decrease in time constant with increasing applied field strength (and subject to limits at very high field strengths). The zero field time constant and/or low field time constants associated with a tracer, and also associated with the center of the FFR in an MPI system, will thus in general be associated with the longest relaxation times and will set the half-period requirements to ensure steady-state is achieved. This will also have ramifications on the receive signal bandwidth. The magnetic relaxation dynamics need not strictly follow a single or multiple exponential model. The ramifications of using a square wave-like (or more general) excitation waveform containing substantially constant periods pertain to any real magnetic physics as they are always characterized by finite temporal responses. In contrast, as long as the total applied field is continuously temporally varying, such as in the case of a sinusoidal excitation waveform or the non-substantially constant periods of a pulsed excitation waveform, the tracer distribution is subject to continuous excitation and the relaxation physics will be dynamically varying. In the special case of a substantially constant waveform, as in pulsed MPI, there is no continuous temporal stimulation. There is only a decaying response generated by magnetic relaxation of the tracer distribution evolving according to a fixed spatial pattern and the strong field dependence of magnetic relaxation physics. It is possible that other sources of time-variation in the factors that affect magnetic relaxation, e.g., physiologic sources such as viscosity, binding events, pH, or chemical reactions, may still lead to time-varying relaxation dynamics during a substantially constant field period, which may be separately visible, or encoded, by a pulsed MPI encoding scheme.

FIG. 11, FIG. 12, FIG. 13, and FIG. 19 illustrate various ramifications of excitation with a square-like waveform so defined. During each square wave-like half-period, the magnetization of the tracer distribution will move toward, and with sufficient duration, eventually attain the steady-state magnetization associated with the substantially constant magnetic field state, according to the magnetic physics associated with the tracer. The signal obtained from the inductive receiver coil will be proportional to the time rate of change of the magnetization and thus will decay to zero after some initial feature dictated by the specific response physics. In the limit of an ideal square wave, the magnetization of the tracer distribution will follow exactly the step response of the tracer distribution and the received signal will be proportional to the impulse response of the tracer distribution, in terms of the magnetic relaxation dynamics and with respect to the relative geometry between the FFR and tracer distribution associated with each step.

For a single point source, or a distributed sample excited without the presence of a gradient field/FFR, the magnetization at the end of each half-period will correspond to a single point on the steady-state M-H curve for the tracer at a given total field. For superparamagnetic tracers, as typically used in MPI, this corresponds to a point on the steady-state Langevin curve. For a distributed point source in the presence of a gradient field/FFR, the total magnetization at the end of each half-period corresponds to the spatial integral of the tracer distribution density mapped to corresponding points on the tracer's M-H curve according to the specific shape of the FFR in use. This relationship between steady-state inducing constantly held periods and sampling of the M-H curve is illustrated in FIG. 11 and represents the realization of steady-state signal encoding in MPI even in the presence of finite (and possibly arbitrarily large) magnetic relaxation. Such an encoding is desired and sometimes assumed in much of the original MPI theory in which finite relaxation is often neglected. But achievement of steady-state encoding in practice has not been attainable for larger particles with long relaxation times relative to the periods of the sinusoidal excitation waveforms typically used. This has precluded access to the greatly improved resolution possible with these larger particles according to the steady-state theory.

Steady-State Recovery Excitation Encoding

Steady-state recovery sequences can encode tracer response dynamics obscured in other encoding regimes or if multiple response dynamics that have greatly different response times contribute to the overall magnetization evolution and thus received signal.

In some embodiments, steady-state recovery pulse sequences are constructed with variable-duration substantially constant periods separated by short excitation pulses as illustrated in FIG. 10. In some embodiments, excitation pulses applied after a steady-state is established provide a baseline magnetization or signal value to contextualize the signal associated with other excitation pulses in which steady-state is not achieved preceding the pulse. For example, the first pulse associated with a specific mean location of the FFR isocenter may provide this information while a series of subsequent pulses with changing interpulse or recovery times encode the dynamics of the steady-state recovery. During the substantially constant interpulse periods, the original mean FFR isocenter location is recovered. When this substantially constant period is of an insufficient duration to allow full recovery of the steady-state magnetization after the previous pulse impetus, the signal associated with the next pulse will be attenuated compared to the case of full steady-state establishment. The degree of attenuation, or lack of full recovery, will be a function of the tracer response time of the excited components of the tracer distribution. The encoding of the tracer dynamic response with variable interpulse recovery times is apparent in the envelopes of the time domain signal as seen in the experimental data of FIG. 20.

The variation in signal associated with each pulse is directly related to the magnetic response time of the tracers when the FFR isocenter is located at the position associated with the interpulse period. In some embodiments, a small number of pulses will be associated with a given interpulse FFR isocenter location, such as in the range of 3 to 10. In other embodiments, 100 s of pulses may be applied per interpulse FFR isocenter location for a dense sampling of the relaxation dynamics. In some embodiments, a large range of interpulse times will be sampled, for example, in the range of 5 microseconds to 100 milliseconds to fully capture the entirety of all extant relaxation processes. Such broad ranges may necessitate sparse sampling of the interpulse periods or otherwise indicate a tradeoff; in some embodiments the interpulse period variation will follow a power pattern such as square, cubic, quartic and so on while in others exponential sampling may characterize the interpulse period sampling pattern. In some embodiments, much smaller ranges will be queried to increase the sampling density over a specific time range of interest.

In some embodiments, no gradient field or FFR structure will be present. The steady-state recovery sequence may then be applied to a sample with homogeneous excitation coils only to query the zero field relaxation dynamics of the sample in aggregate. In some embodiments, a bias waveform may be applied such that multiple steady-state recovery sequences are associated with mean total field values that are nonzero.

In other embodiments, the steady-state recovery sequence may be applied in the presence of an FFR, but along a low or zero-gradient field direction. For example, the steady-state recovery excitation may be applied along the line in an FFL scanning system. In this manner, it is possible to encode relaxation information as a function of total applied field but also spatially localized and associated with the mean location of an FFR or LFR isocenter.

Steady-state recovery approaches can have advantages over, for example, use of a square wave-like pulse sequence for encoding tracer relaxation dynamics. In general, the magnetic relaxation of a tracer may have both a significant Brownian and Neel component and/or significant relaxation components that occur very quickly, for example, within 10 microseconds, and other significant relaxation components that occur on the timescale of 10 s or 100 s of microseconds or even in the range of milliseconds. In a square wave-like encoding regime, the shortest relaxation components may completely dominate the time domain signal due to the time derivative nature of inductive signal reception. Encoding and observing longer and/or Brownian responses directly in the time-domain signal, which are of great interest for physiologic contrast and sensing, may be difficult in this regime because of time domain SNR, bandwidth restrictions, and/or noise floor limitations. A steady-state recovery approach, as described herein, can be a powerful tool for accurately and robustly measuring these longer and/or Brownian components of the magnetic relaxation signal. In general, multiple encoding regimes may be applied, such as including both square wave-like and steady-state recovery components in a single or sequential excitation waveforms. The time-domain data associated with each pulse in the steady-state recovery sequence may contain similar or equivalent information as a single square wave-like cycle. Using multiple encoding techniques simultaneously or in series can encode different relaxation information, for example in the case of tracers with heterogenous relaxation dynamics, in ways that lead to well-conditioned and robust reconstruction problems.

SNR Efficient Excitation Pulsed Waveforms

Figure 21:
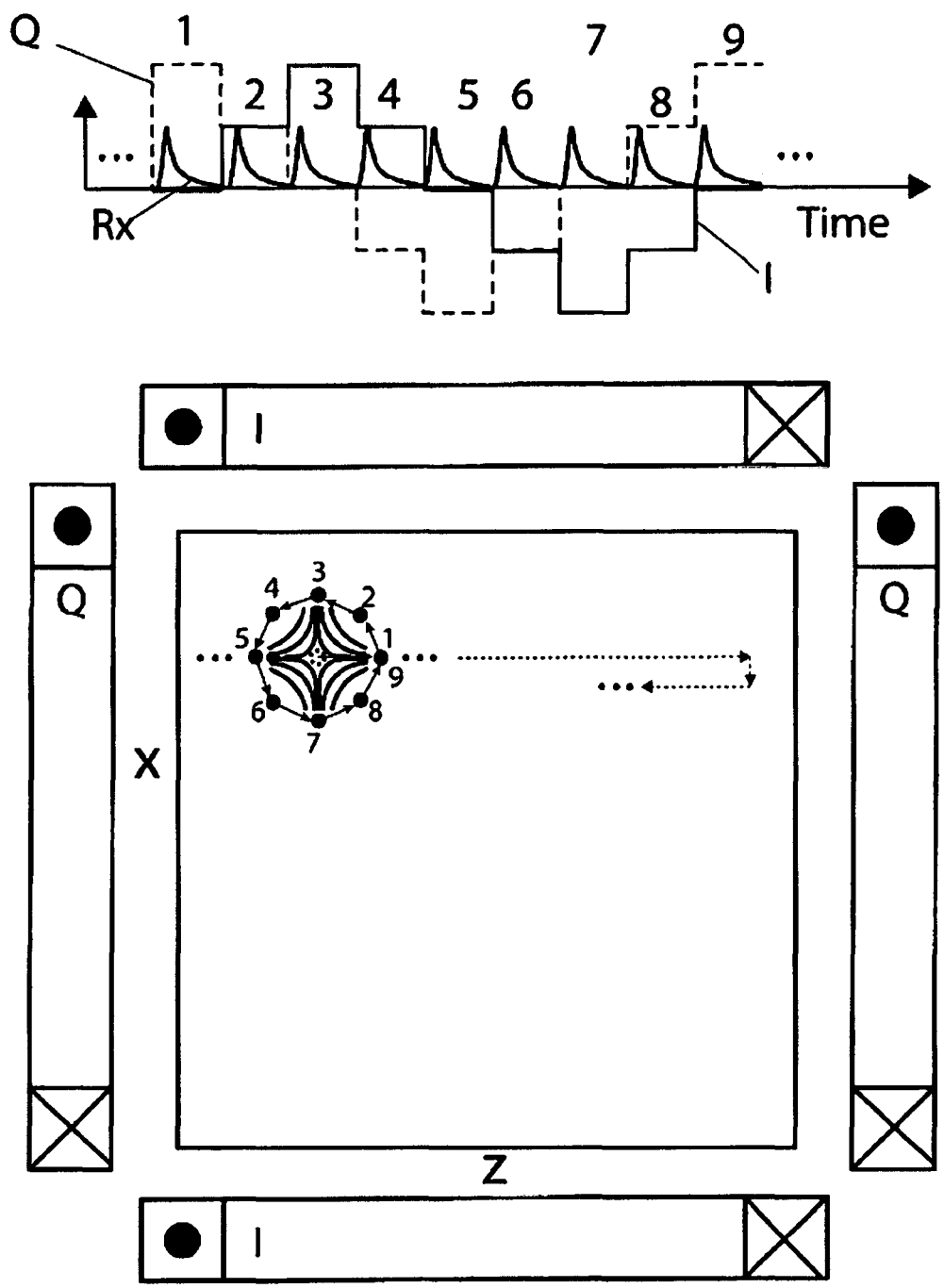
FIG. 21 shows quadrature-based circling of a location with the FFR and trajectory in space according to an embodiment of the current invention.

More complex encoding regimes and pulse sequences may be desirable, for example, to provide greater SNR efficiency. FIG. 21 illustrates how a series of pulses applied to orthogonal coils driven in a quadrature arrangement lead to the rotation of the FFR isocenter around a specific location in the FOV during a specific excitation pulse train. For illustrative purposes, the radius or size of the encircling pattern is not necessarily to scale with respect to the FFR geometry, imaging FOV, and slow shift raster pattern as shown. For example, the encircling pattern may be relatively much smaller in practice. Additionally, the pulse applied at each location may not be a simple substantially constant period; rapid transitions may separate any of a number of pulsing shapes as illustrated in FIG. 5, including brief sinusoidal pulses after rapidly transitioning the mean location of the FFR. The duration of the pulse associated with each of the numbered locations surrounding the central point may be much less than that required to establish steady-state conditions but will elicit a significant temporal peak associated with the rapid transitions and/or response to general excitations. In some embodiments, steady-state inducing substantially constant periods may be used in combination with such fast excitation and readout waveforms. In general, a rotating excitation may provide a relatively large aggregate signal associated with a location or small region in the imaging FOV and over a small period of time, increasing SNR efficiency when compared to simpler raster scans. This encircling pulsed waveform can be repeated in concert with slow shifting fields to sample an entire imaging FOV over time.

Other System Sequencing

Figure 18:
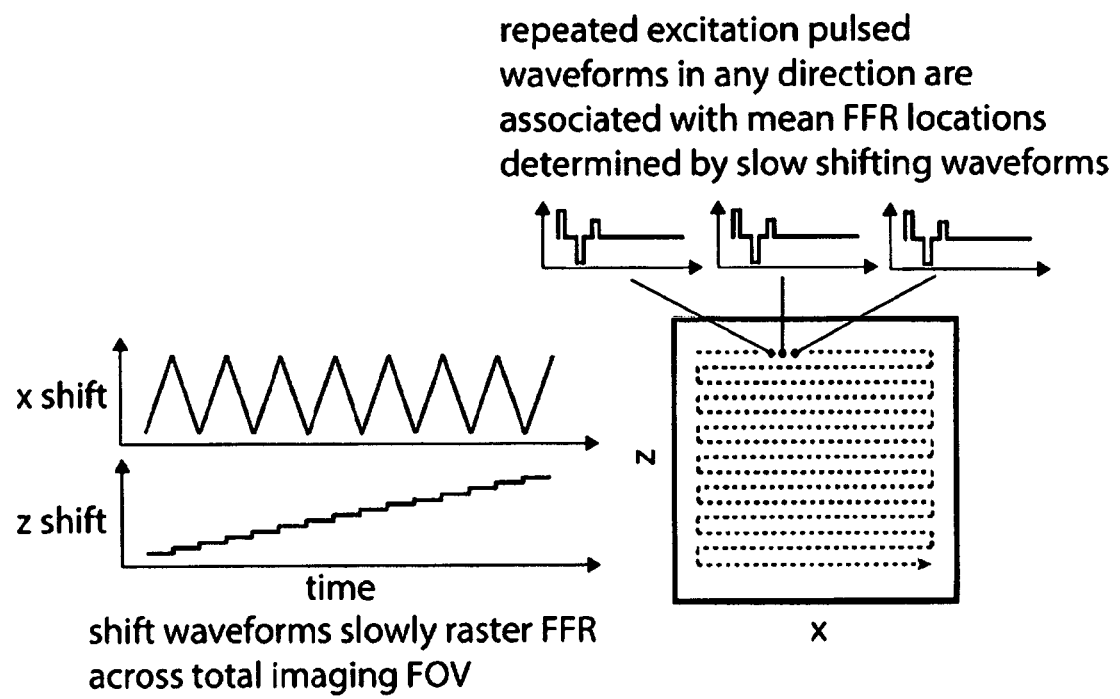
FIG. 18 shows repeated excitation pulse sequences associated with mean FFR locations from shift waveforms according to an embodiment of the current invention.

As illustrated in FIG. 17, FIG. 18, and FIG. 19 pulsed excitation waveforms will generally be used in conjunction with other important sequences to accomplish full tomographic or projective imaging. In general, we note that pMPI encoding may be used with system matrix methods in which many calibration scans are taken with a point source located at different locations in an imaging field of view (FOV) to construct a system matrix that may be inverted to produce images of possibly more complex samples taken with the same system and scanning trajectory.

Slow Shifting

To cover a large imaging field of view (FOV), e.g., larger than displacements associated with excitation waveforms, slowly varying homogeneous waveforms may be superposed with repeated excitation waveforms. This allows the mean location of the FFR isocenter to slowly translate over time as depicted in FIGS. 17, 18, and 55. Slow shifting waveforms may be sufficiently slow compared to the time scale of the individual excitation components of the periodic excitation waveforms that the influence of the slow shifting waveform on moving the FFR structure during an individual excitation period is negligible and the temporal guarantees on, for example, the maximum deviations from a desired magnitude in substantially constant periods of pulsed waveforms, are maintained. In other embodiments, especially in which fast acquisition is desired, the effect of slow shifting waveforms may augment the excitation of the tracer in a non-negligible manner.

Multiple slow shifting waveforms may be associated with each of the principal axes that are to be shifted in a given scan. For FFL scanning systems, two shifting components aligned with the plane orthogonal to the line of the FFL may be used in acquiring projection images and successive projection images may be taken after a rotation of the relative geometry between the FFL and sample about a fixed axis as depicted in FIG. 17. For an FFP scanning systems, shifting the FFP in all three dimensions is required.

FIGS. 17, 18, and 55 depict specific embodiments of shifting waveforms that raster the FFR across a total imaging FOV. In general, other shift waveforms may be used to sample a larger FOV over time with different trajectories. For example, non-Cartesian radial or spiral slow shift trajectories may be desirable in certain applications. Furthermore, depending on the FFR structure, shift waveforms may sample larger 3D regions over time. In the case of FFR structures localized in all three dimensions, such as an FFP, shift waveforms may be associated with all three principal axes to arbitrarily move the FFP through three-dimensional space. In the case of an FFL, rotational waveforms, as depicted in FIG. 17 will be required for tomographic imaging. In some embodiments, 2D slice data will be acquired with discrete projection angles as realized by the rotational waveforms. In other embodiments, the projection angle may be continuously varied during data acquisition. Rotation may be accomplished by one or both of: rotating the FFL-producing magnet system with respect to the sample or rotating the sample with respect to the FFL-producing magnet system.

Gradient Waveforms

Figure 22:
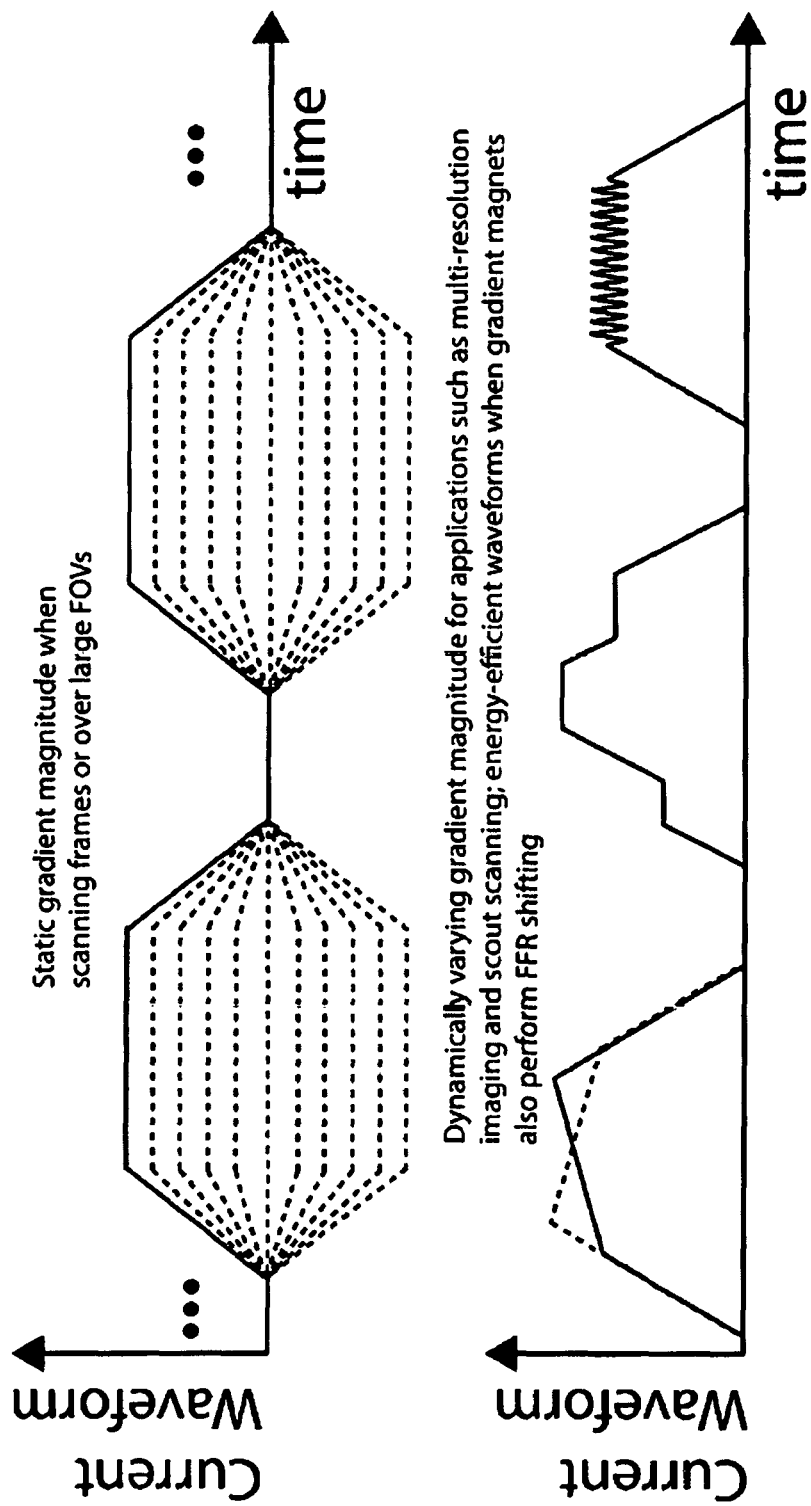
FIG. 22 shows examples of gradient waveforms according to some embodiments of the current invention.

When using electromagnets as the source of the gradient fields that generate the FFR structure, gradient waveforms of different types may be desired depending on the application as illustrated in exemplary gradient waveforms shown in FIG. 22. For example, a constant gradient strength may be applied throughout the entirety of an imaging scan. This strength may be modified in between multiple scans such that multiple imaging data sets are taken at different gradient strengths. For example, a fast scout scan taken at low resolution may be performed prior to longer scans with higher gradient strengths and improved intrinsic spatial resolution encoding. Information from the scout scan may be used to set imaging parameters in subsequent scans.

It may also be desirable to dynamically modulate the strength of the gradient during an imaging scan as shown in the bottom of FIG. 22. This may be desirable with active feedback from signal processing modules to coarsely scan regions of the FOV with little or no signal and increase the gradient, and therefore intrinsic MPI resolution encoding, only in the presence of signal. For sparse tracer distributions, this may provide much faster scanning. Repeated and fast modulation of the gradient waveform, subject to magneto-stimulation and/or SAR slew limitations, may be used to provide multi-resolution encoding throughout the imaging FOV in a single scan without requiring multiple traversals or scans.

Signal Processing and Reconstruction

Figure 23:
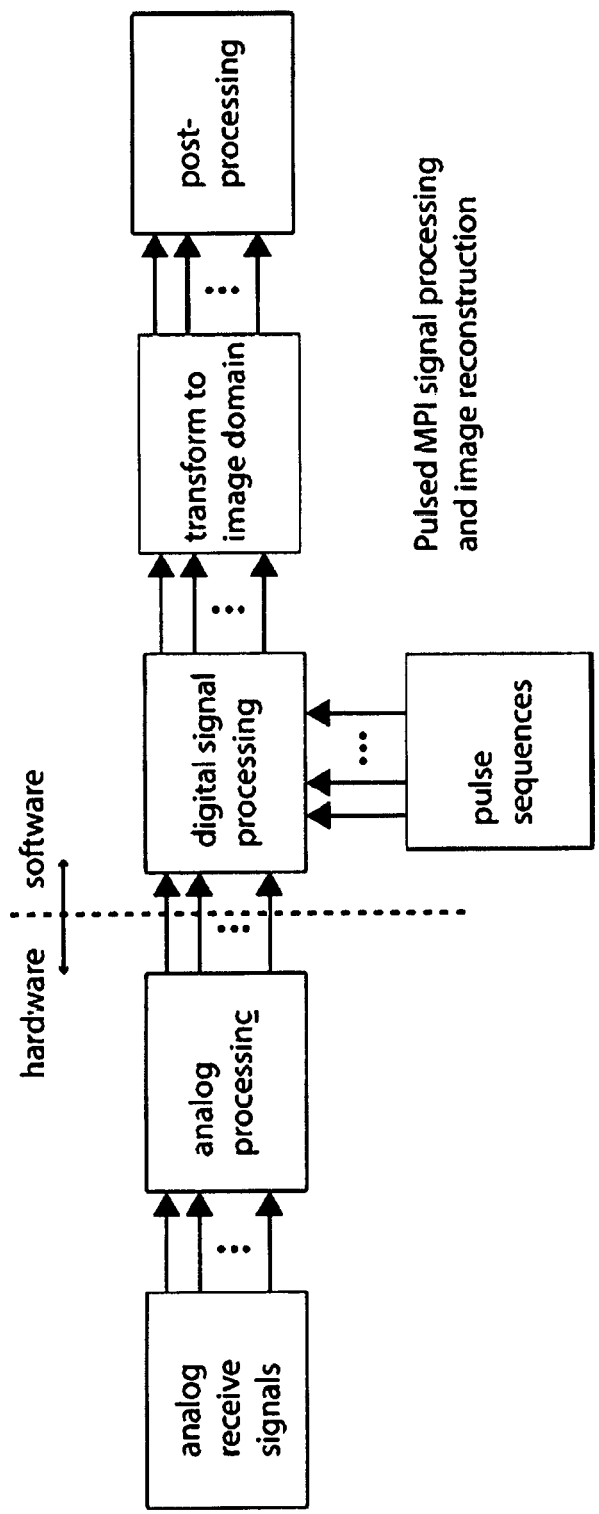
FIG. 23 is a digital signal processing and reconstruction block diagram according to an embodiment of the current invention.

Pulsed MPI encoding regimes admit multiple methods of forming images from received data. FIG. 23 describes major components in pulsed MPI x-space digital signal processing and reconstruction. Analog received signals from receiver coils are sampled and digitized at the end of the receive electronics chain. These signals are used, along with the known pulse sequences applied in the scan, to perform various signal processing and conditioning tasks. These may include tasks such as digital filtering, piecewise reduction steps such as integration or thresholding, and phase correction. These tasks may be completely performed in the time domain, without transforming data, for example, into Fourier space. In other embodiments, data may be transformed or projected onto a suitable basis set.

Figure 24:
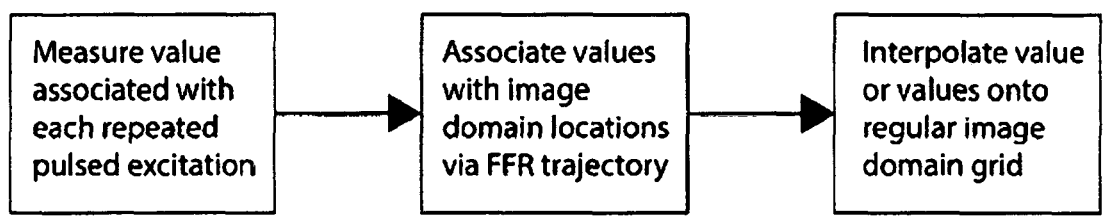
FIG. 24 is a schematic illustration of a general embodiment of image formation in pulsed MPI according to the current invention.
Figure 25:
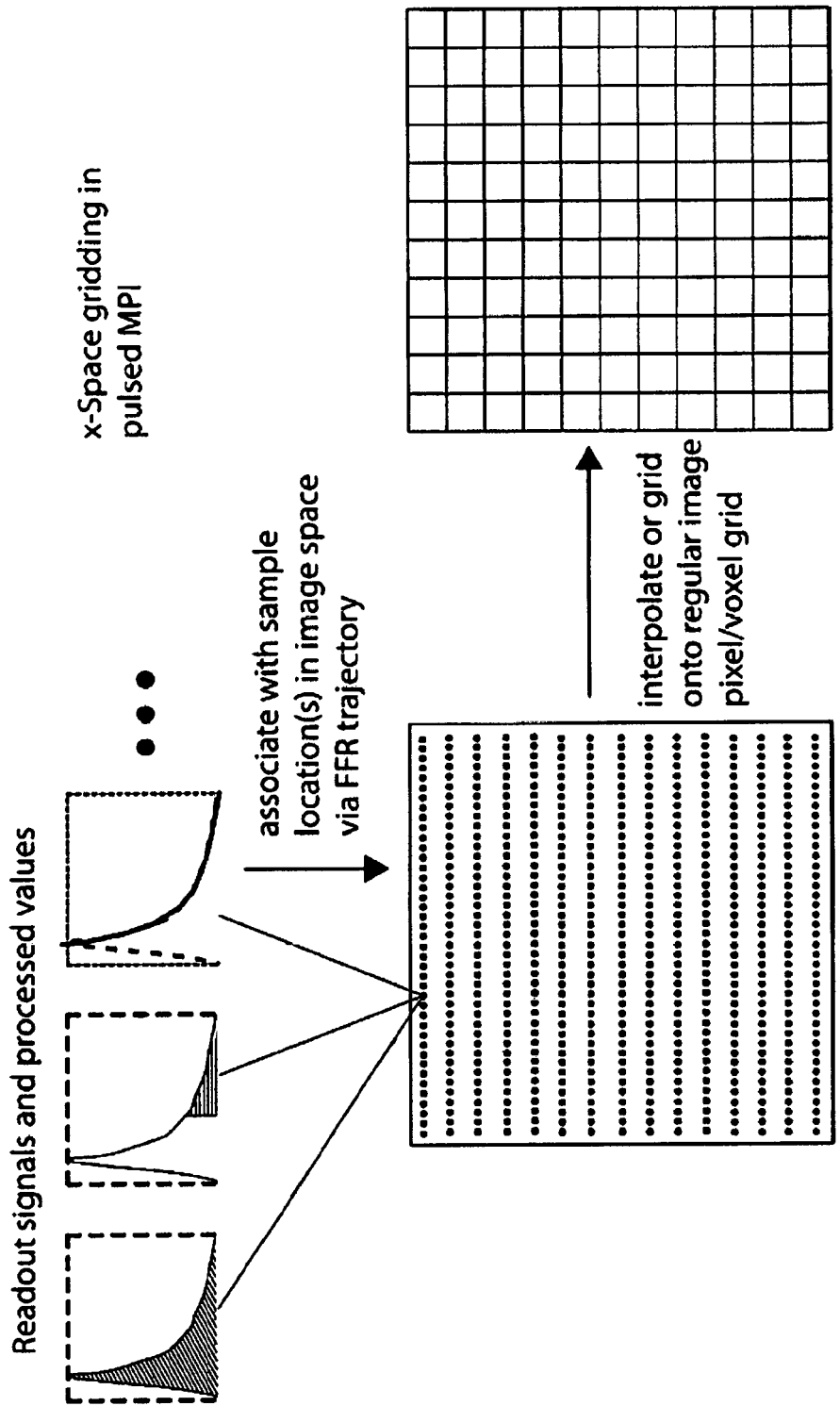
FIG. 25 shows generic x-space gridding in pulsed MPI according to an embodiment of the current invention.

After completion of digital signal processing steps, one or more resulting signals will be directly transformed, or combined and then transformed, into an image domain. A common pattern in pulsed MPI is to process the time domain signal such that a single value or a small number of values are associated with each of the repeated aspects of the excitation pulse sequence as illustrated in FIG. 18, FIG. 24, and FIG. 25. In an x-space method, these single values or small number of values may then be correlated with physical locations in image space, for example, based on the mean location of the FFR isocenter with respect to shifting and possibly excitation waveforms during each of the repeated excitation pulse sequence patterns or readout periods. The sampling density in terms of FFR locations associated with each pulsed excitation period may be non-uniform, and a many-to-one relationship will typically exist between the set of sample points and the set of final image domain pixel/voxel locations that constitute a desired regular image space grid. Some form of interpolative gridding procedure with averaging or weighted averaging may be employed to implement this mapping. Various interpolation schemes may be used in this process. For example, interpolation via the nearest-neighbor method, linear interpolation, or higher order interpolation algorithms such using polynomials or splines may be employed. The interpolative gridding step may also apply filtering processes, for example to reject values with low SNR, prior to or concurrent with gridding.

It may also be desirable to use a system matrix method of reconstruction. In such a method, a pulsed MPI system matrix is constructed from many sets of pulsed MPI acquisition data. In particular, a point source may be placed at the center locations of final pixel/voxel locations. For each location, a pMPI acquisition, such as described in FIG. 17, FIG. 18, and FIG. 19 is performed. The data associated with each such acquisition may be used to construct a single row or column of a system matrix. Between acquisition and storage as a matrix row or column, various digital signal processing and/or mathematical transformations such as transformation to the Fourier domain may be applied. Additionally, the data associated with each acquisition may be fit to an analytic model, mathematical function, minimal basis set, or otherwise compressed to minimize the storage requirements for the system matrix. For example, it may be desirable to perform x-space integrated gridding of the raw or processed data associated with each periodic readout-period using the known FFR-isocenter trajectory as previously described. The resulting x-space images for each point source location can then be used to fill the rows or columns of a system matrix. Regardless of precisely how the pMPI system matrix is constructed, imaging of a generic sample is then provided by applying the same excitation sequence, as applied to each point source, to a sample of interest. A manifest matrix inverse problem may then be solved using any of the standard algorithms, possibly including various regularization methods and constraints, to generate the final image. Using pMPI encoding for system matrix methods may be desirable or advantageous over continuous wave system matrix methods because the improved resolution encoding of pMPI improves the orthogonality of the rows or columns of a system matrix, which in turn improves the conditioning of the matrix inverse problem. When the voxel size of a system matrix approach is chosen that is similar in size to the native or Langevin FWHM size, then greatly improved conditioning of the inverse problem results. By reducing or removing the effects of magnetic relaxation, especially for larger tracers, pMPI encoding can provide well-conditioned system matrix formulations for smaller pixel/voxel sizes than that available using continuous wave pMPI encoding.

One or more images constructed as described previously may undergo final postprocessing steps. For example, one or more images reconstructed at different resolutions may be combined into a single image, one or more images may be used to create one or more new images with colorized contrast, or one or more tracer density images may be combined with one or more relaxation images to create four-dimensional imaging data sets with a relaxation spectral information axis. In general, the production of distinct tracer density and tracer relaxation images is a feature of pulsed MPI.

Tracer Density Reconstruction

Images of the tracer density may be reconstructed using various gridding methods. The time domain data associated with substantially constant readout periods or more complex and repeated pulsed excitation waveforms may be integrated and the resulting value gridded to a pixel or voxel location. The gridding procedure may use the known x-space trajectory of the FFR isocenter to map time domain signals to image space locations. In some embodiments, the mean location of the FFR isocenter during a repeated pulsed excitation or the single location of the FFR isocenter associated with a substantially constant readout period will provide the rule for this mapping.

Figure 26:
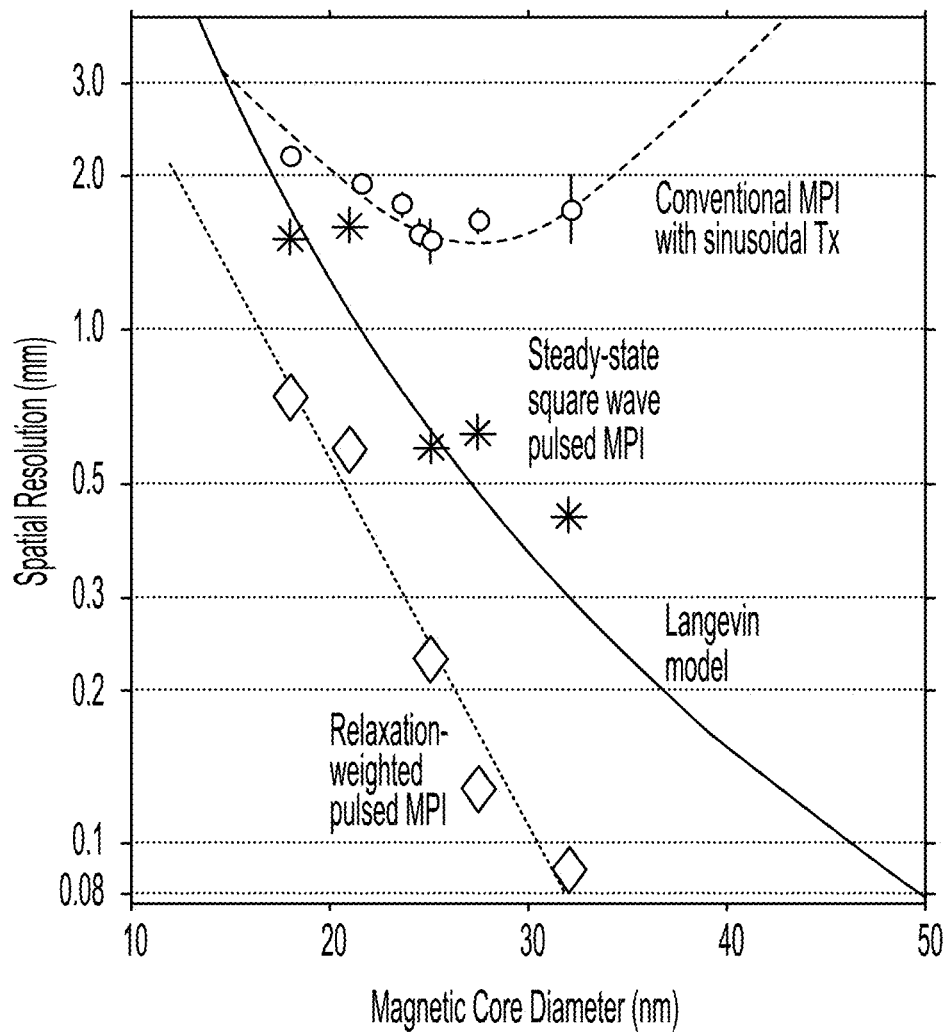
FIG. 26 provides experimental resolution comparison between traditional MPI, square wave pulsed MPI, and relaxation weighed pulsed MPI.

FIG. 26 shows a plot of native resolution as a function of tracer core diameter from experimental data using traditional sinusoidal MPI and two different reconstruction methods in pulsed MPI. The theoretical Langevin limit is also shown. In these data, traditional continuous sinusoidal wave MPI resolution does not improve beyond a tracer core size of approximately 25 nm due to the impact of magnetic relaxation on the reconstruction process. All other variables being constant, the degree of magnetic relaxation is typically a strong function of the tracer core size, with longer relaxation times associated with larger tracers. This generally prevents achievement of native resolution predicted by the ideal Langevin theory in standard MPI. However, pulsed MPI methods show continued resolution improvement for larger core sizes and relaxation-weighted reconstruction methods provide resolution greater than that predicted by steady-state Langevin theory alone.

Figure 27:
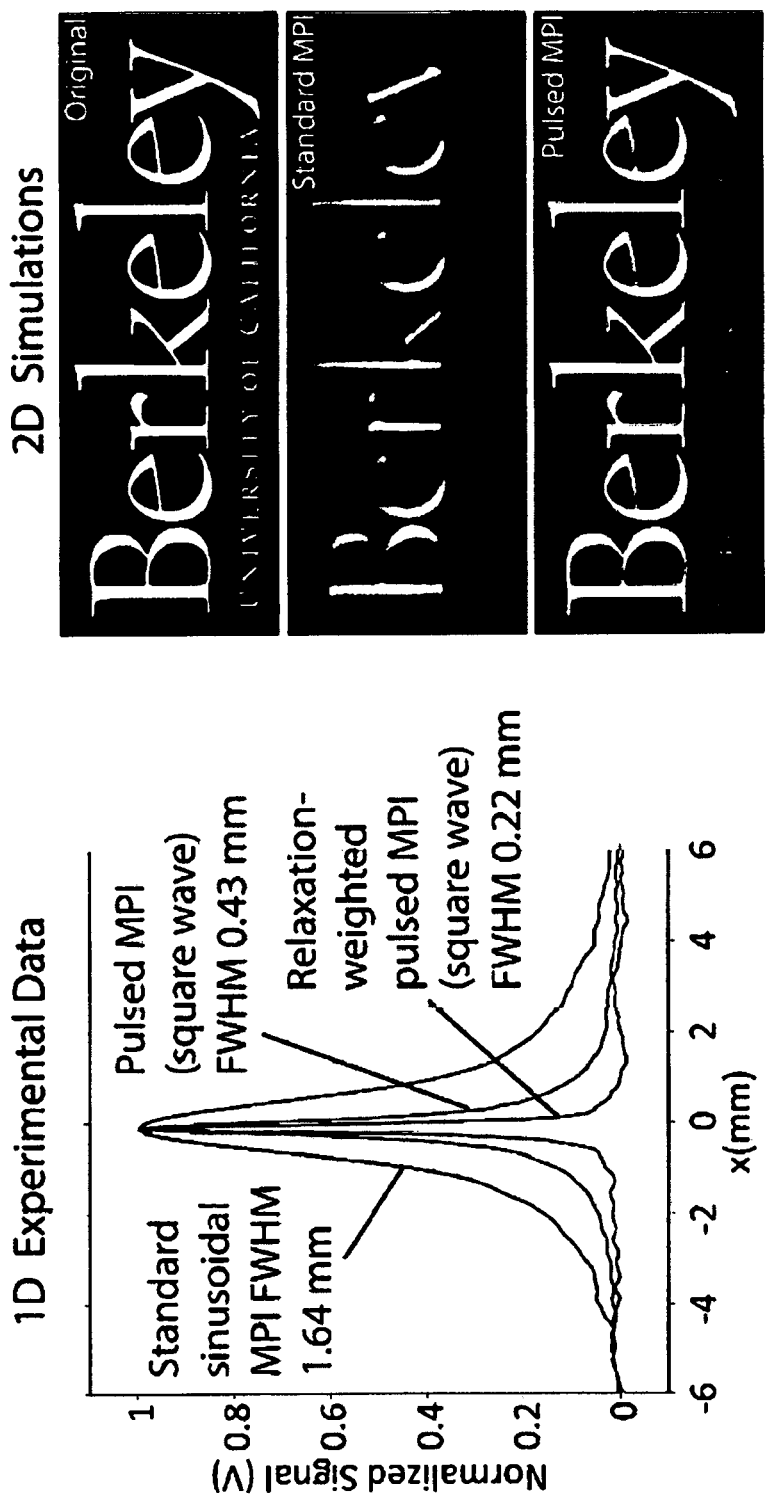
FIG. 27 shows experimental PSF comparison data and extrapolated 2D simulation.

FIG. 27 shows experimental 1D PSFs and resolution measurements (FWHM) obtained with the AWR for the same tracer using two different pulsed MPI reconstructions and showing the improved native resolution using pulsed MPI techniques compared to traditional MPI methods. On the right, the 1D PSF information was used to simulate the expected effect in a two-dimensional imaging context.

Figure 54:
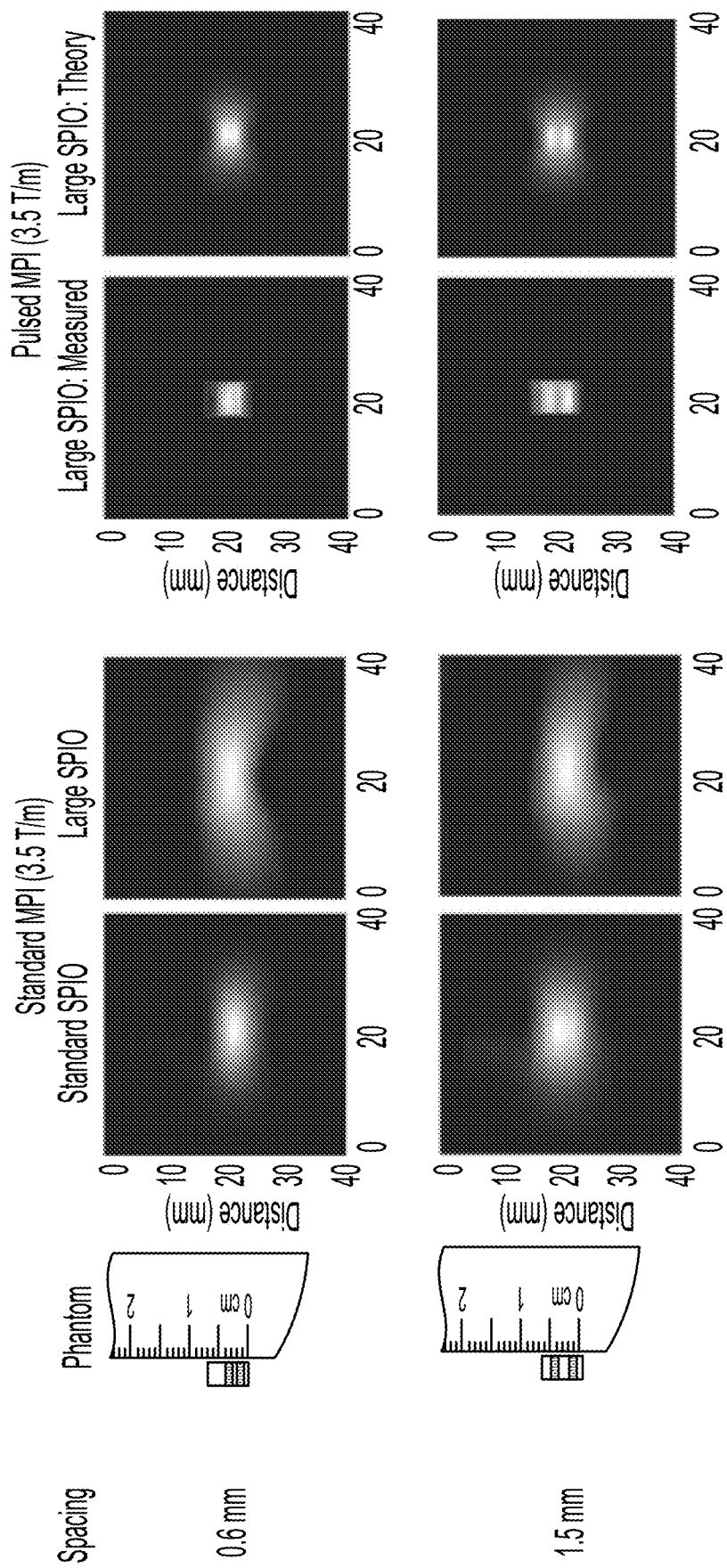
FIG. 54 shows experimental data demonstrating 2D pulsed imaging, comparing 2D pulsed magnetic particle imaging (pMPI) results with analogous sinusoidal excitation 2D imaging and theory, and demonstrates the resolution improvement capable using pMPI.

FIG. 54 shows experimental 2D images of phantoms comparing canonical sinusoidal MPI data obtained with a 3.5 T/m MPI system and 2D pulsed MPI images obtained with a 2D-enabled AWR system (AWR modified with an FFL magnet and shift system). The standard MPI data shows how a larger tracer (27.4 nm single core tracer) has poor resolution compared to a standard tracer (VivoTrax™). The 2D Pulsed MPI data using the larger tracer is much sharper and very similar to a theoretical Langevin simulation in an adjacent plot. The two points of the 1.5 mm sample cannot be resolved in the 3.5 T/m standard MPI images but can be resolved in the 3.5 T/m pulsed MPI images.

In some embodiments using an FFL-based or other projective FFR-based pulsed MPI system, projection reconstruction may first be applied to raw time domain data collected at different relative angles between the FFL/FFR and imaging volume prior to calculating image domain values and gridding or interpolating these values. In such a manner, time domain data may be associated with locations resolved in all three spatial dimensions prior to reducing the time domain data to image domain values.

Direct Integrated Gridding.

The integral of the time domain data associated with readout periods may be directly interpolated or gridded onto a regular pixel or voxel grid based on the location of the FFR during the readout. The grid location may also be partially determined by the locations of the FFR prior to readout, for example, during a magnetization preparation or a previous readout period.

Square Wave PSF Reconstructions with AWR

Figure 28:
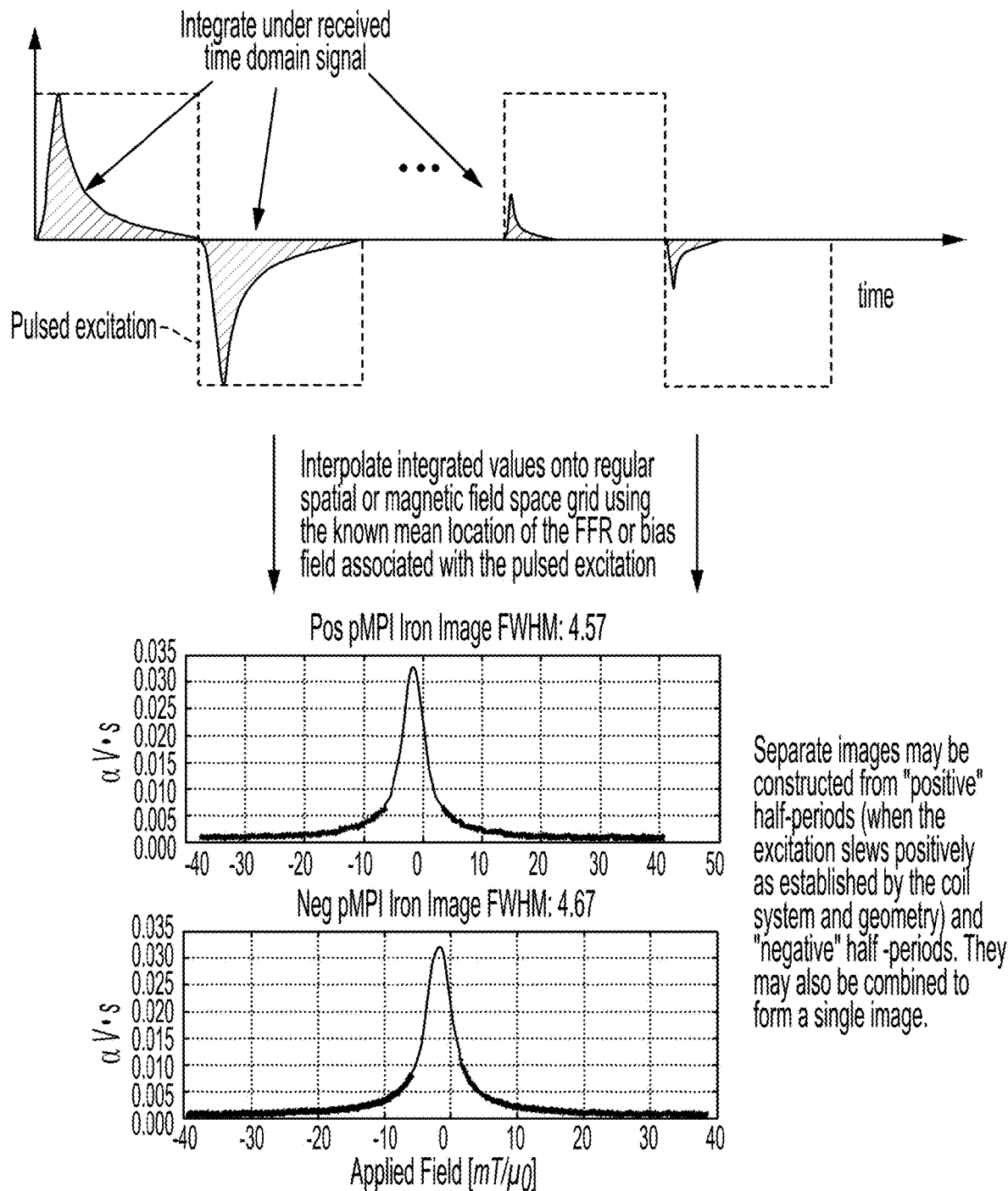
FIG. 28 is a diagram illustrating direct integrated gridding to mean FFR location with pulsed excitation experimental data.

FIG. 28 illustrates one embodiment whereby the integrated area under the curve of the received voltage signal for one or more receive coils and associated with each square wave-like half-period step is gridded to a mean FFR isocenter location. In the case of a scan without a gradient field or when using the AWR, this process corresponds to gridding to the mean of the total applied field when a bias field is used. In the embodiment described by FIG. 28, the single value obtained from integrating the received signal is gridded to the average of the FFR isocenter location in the previous half-period and the current half-period, or equivalently, the midway point along the line connecting the location of the FFR before and after each step. In the case of scan with no gradient, the corresponding grid location in applied field space is the mean of the two total applied field values associated with the previous and current step. Because the step jumps in a square wave excitation represent a projective excitation, exciting all tracer along the line connecting adjacent square wave half-periods to some degree, a direct integrated gridding approach as in this embodiment will incur a projective blur based on the size of the square wave amplitude. The blur will also depend on the duration of the square wave-like half-period unless fully steady-state conditions are achieved during each half-period. If steady-state is achieved, the blur reaches a maximum, becomes symmetric about the midway point, and may be characterized itself as a rectangle function mathematically.

The experimental data points closest to the theoretical Langevin curve in FIG. 26 were obtained using square wave-like pulsed MPI excitation and reconstruction in which the square wave half-period exceeded the tracer's maximum relaxation time and small square wave amplitudes, relative to the FWHM of with the derivative of the steady-state Langevin curve associated with the tracer, were used to minimize the projective blur inherent to this direct integrated gridding technique. The experimental PSF shown in FIG. 27 labeled as square wave pulsed MPI was also obtained with a low amplitude, steady-state inducing square wave pulsed MPI approach. In some embodiments the choice of the square wave amplitude will be small to achieve resolutions arbitrarily close to the ideal, such as in the range of 0.25 mT to 1 mT. In other embodiments, larger amplitudes will be used to increase SNR and incur a modest resolution penalty. In general, the SNR-resolution balance can be varied arbitrarily by choice of square wave amplitude subject to constraints such as magnetostimulation/SAR, hardware and power limitations, and signal digital resolution.

Integrated Gridding with Projection Reconstruction Techniques

Figure 29:
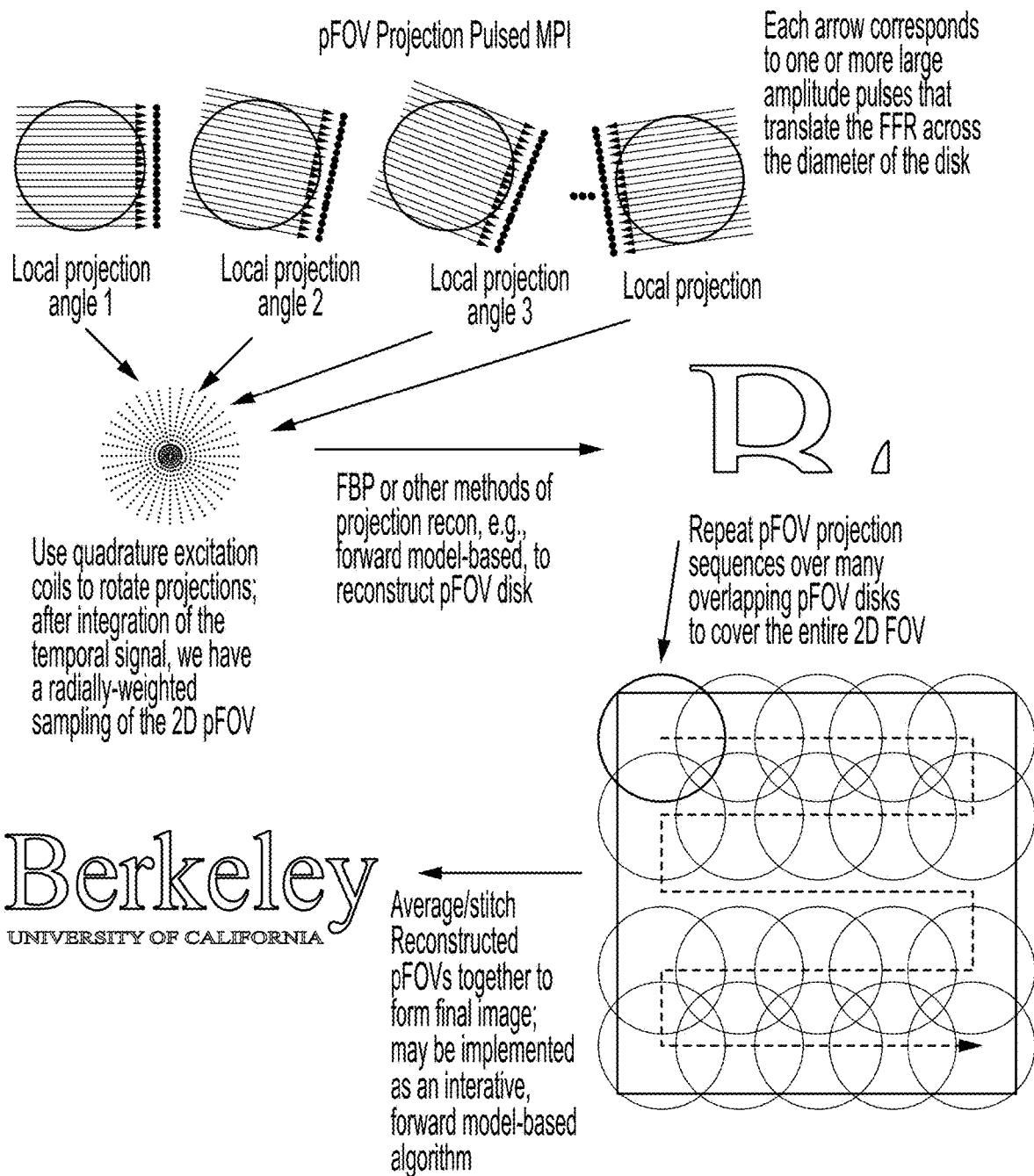
FIG. 29 is a diagram describing a local pFOV projection reconstruction according to an embodiment of the current invention.

In some embodiments, projection reconstruction techniques may be applied instead of direct integrated gridding. This may be a desirable approach to use larger pulsed excitation amplitudes without incurring a large projective blurring penalty. A pulsed excitation may be viewed as a local projection along the excitation direction. Quadrature excitation coils or other mechanisms of rotating the relative geometry between the sample and excitation direction of the pulses may be used to provide samplings of a local partial field-of-view (pFOV) at different excitation angles, enabling local projection reconstruction techniques as illustrated in FIG. 29.

Figure 30:
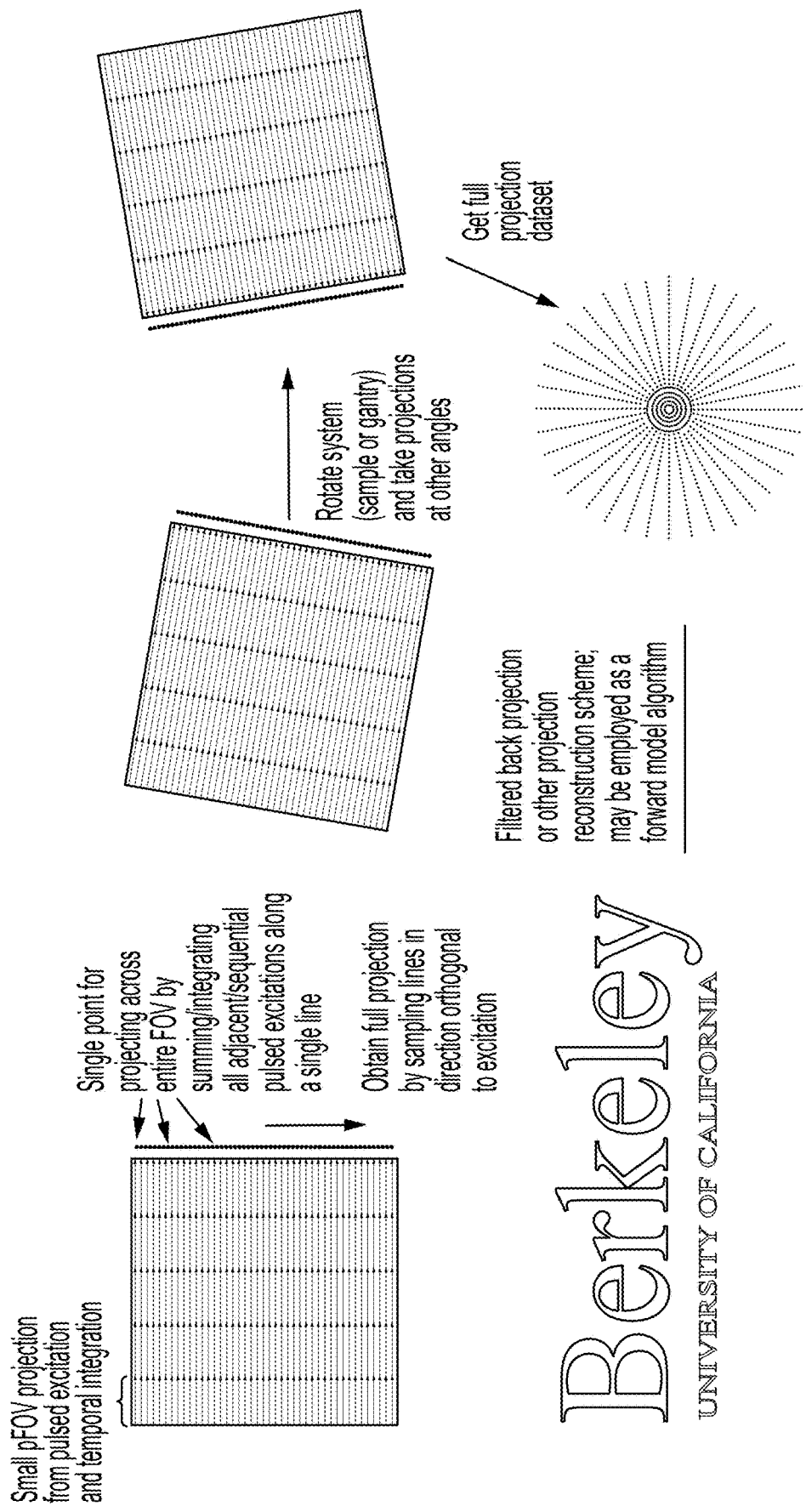
FIG. 30 is a diagram describing a full FOV projection reconstruction according to an embodiment of the current invention.

In other embodiments, many local pFOV projective excitations may be summed together or otherwise combined to obtain a full FOV projection. In this manner, a single full FOV projection reconstruction may be performed after many angles are sampled as illustrated in FIG. 30.

These projection reconstruction approaches may provide improved SNR efficiency due to the SNR benefits inherent in projection reconstruction approaches. In general such a benefit will depend on the number of steps required per angle, the number of angles, and the number of projection reconstructions per slice. From an encoding and reconstruction perspective, when used in an excitation direction orthogonal to the line direction of an FFL, these approaches represent a way of emulating the use of a field-free plane or field-free slab FFR geometry. In general, inverse formulations, forward model formulations, and iterative reconstruction algorithms may be desirable to solve these projection reconstruction problems.

Magnetization Image Reconstruction

When a pulsed MPI excitation sequence is used in which the magnetization of the tracer distribution achieves a steady-state by the end of each successive readout period, it is possible to consider reconstructing images of the magnetization directly, either as an intermediate or final image.

In the case where steady-state is established during each readout or more generally between successively repeated pulsed excitation waveforms, the area under the curve of the signal associated with the received coil during each repeated excitation period is proportional to the finite difference between the absolute magnetization state established in one excitation cycle and the previous cycle. In some embodiments, this constitutes a recursive relationship between all successive excitations. With known initial conditions, these recursion equations can be solved to yield a signal proportional to the absolute magnetization associated with the end (steady-state) of each pulsed excitation. These values may be gridded to mean FFR locations, as described previously, to obtain a magnetization image.

In some embodiments, finite difference and algebraic methods such as inversion of a Toeplitz matrix may be employed to solve the recursion equations. Depending on the pulse sequence encoding, this method of reconstruction may suffer from poor conditioning and be ill-posed. A priori assumptions or specific encoding regimes may be leveraged to improve this situation. For example, non-Cartesian FFR trajectories in which a single FFR location is used as a reference or anchor between sampling of many successive FOV locations may be employed. In some embodiments a zero field excitation in which the excitation source and possibly shifting sources are switched off will establish an absolute reference and break the recursive relationship.

Such a magnetization image may be characterized by a PSF that lacks the finite support and even symmetry typically desired in medical imaging. In some embodiments, a well-posed magnetization image reconstruction will be followed by the application of finite difference or numerical derivative techniques to realize a final image with a Langevin PSF more typical in MPI. In some embodiments, both procedures will be formulated into one reconstruction algorithm, for example using a forward model description of the system. Smoothing or regularizing measures may be taken when performing such transformations to avoid significant amplification of image noise. These may leverage robust a priori assumptions, for example, assumptions about the spatial bandwidth of the expected tracer PSF. An image so constructed will not suffer from projective-blur as in the case of direct integrated gridding.

Relaxation-Weighted and Relaxation-Filtered Reconstruction

Some pulsed waveforms with magnetization preparation sequences will inherently weight the signal using the spatially variant magnetic relaxation conditions present in the context of a gradient or FFR as illustrated in FIG. 10 and FIG. 12. In addition to any magnetization preparation, all readout periods that include at least one substantially constant region contain a well characterized intrinsic spatial encoding in the time domain data associated with the constant readout period as illustrated in FIG. 12.

Figure 31:
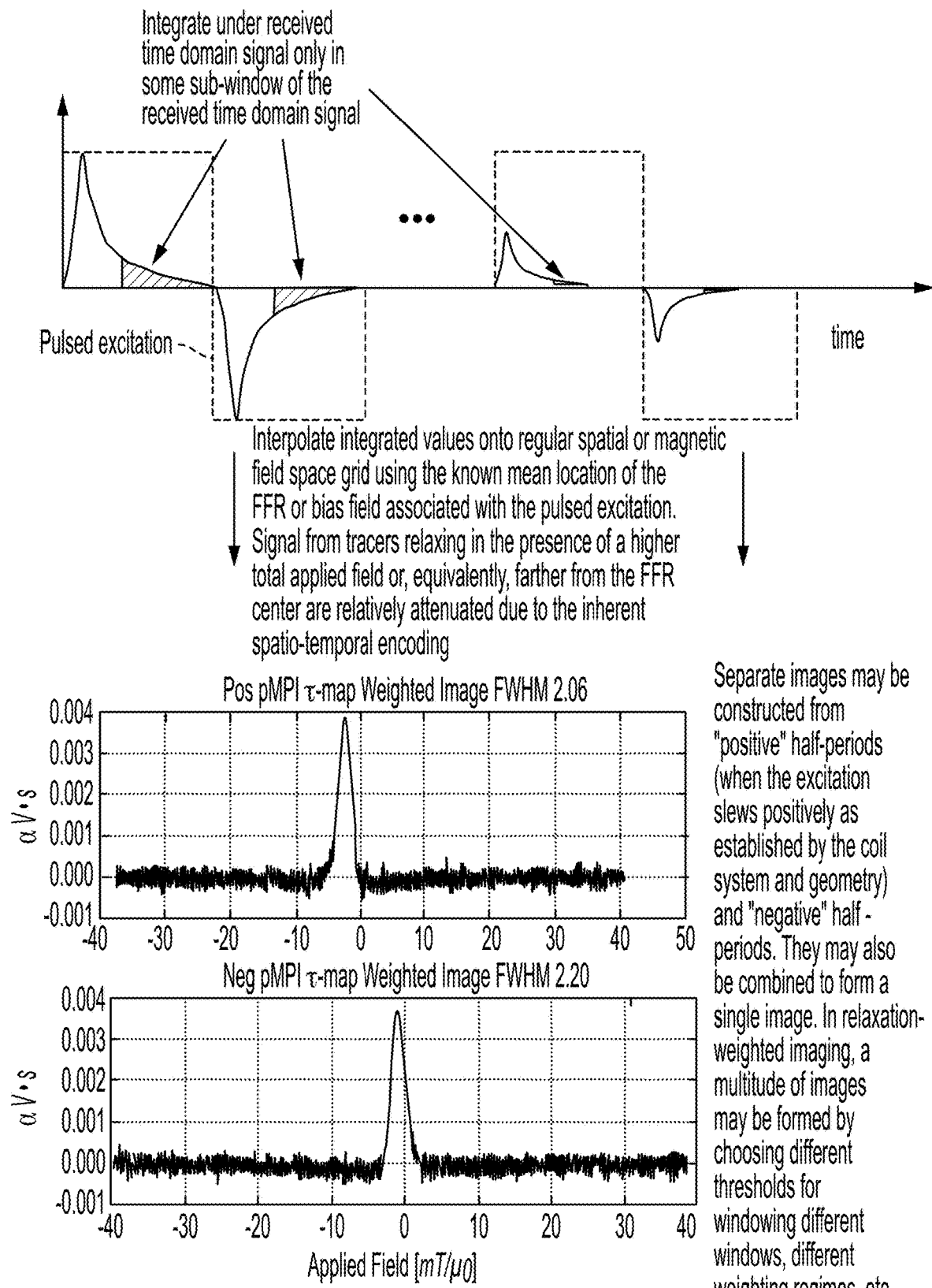
FIG. 31 is a diagram illustrating relaxation-weighted reconstruction with experimental data according to an embodiment of the current invention.

During reconstruction, selective integration, windowing, temporal decomposition, various temporal weightings, or filters can be applied to use this secondary spatial encoding to improve the resolution of tracer density images, possibly at the expense of SNR. This represents a coupling of the tracer density information with relaxation dynamics. One embodiment with resulting experimental data is shown in FIG. 31. Relaxation weighting so performed may improve resolution to better than that possible with steady-state Langevin physics, previously considered a fundamental limit in MPI with respect to native resolution, as illustrated in the experimental data points of FIG. 26. Relaxation weighting may be applied in digital signal processing of the received time domain signal prior to any of the reconstruction methods previously described.

Figure 33:
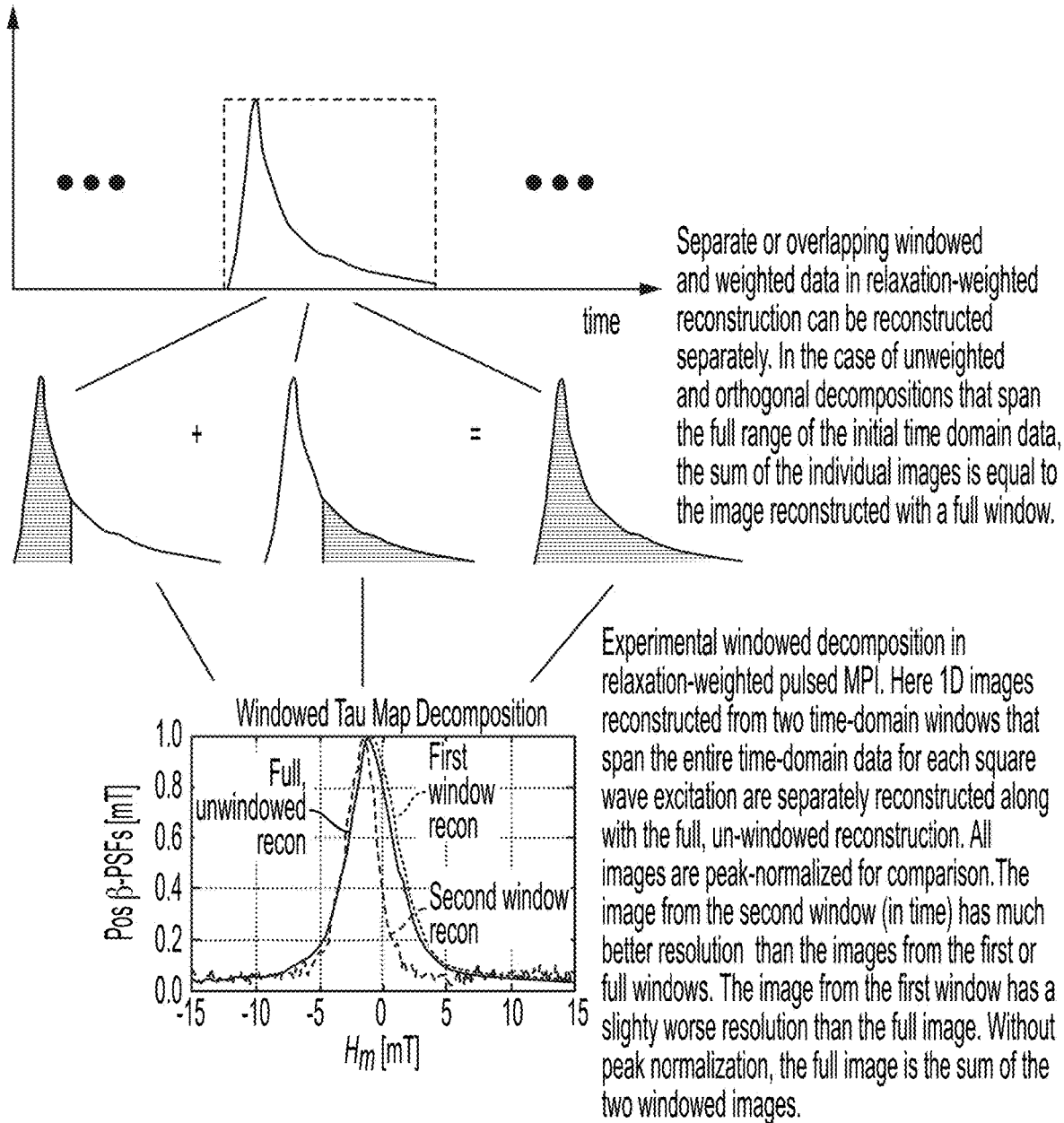
FIG. 33 shows an example of relaxation-weighted decomposition according to an embodiment of the current invention.

In some embodiments, relaxation weighting may be performed by selective windowing or thresholding of the time domain data associated with readout periods and prior to signal integration and gridding steps. Windowing may be performed in various ways, and distinct images may be produced associated with one of many different windows applied to the data. For example, multiple non-overlapping windows may be applied to a data set as illustrated in FIG. 33. As illustrated in these data and in FIG. 12, the time-domain signal corresponding to early parts or windows of the readout period is more associated with tracer farther from the FFR isocenter while the time-domain signal corresponding to later parts or windows is more associated with tracer closer to the FFR isocenter. Images reconstructed from data associated with later windows or after certain temporal thresholds can have greatly improved resolution at the expense of SNR. Images reconstructed from a set of non-overlapping windows that cover the full range of the time-domain dataset associated with the readouts have the property that the superposition of these images is equivalent to a single image reconstruction with a single window that covers the entire time-domain readout period. In this manner, these windowing procedures may be viewed as decompositions of the full signal.

More general weighting procedures may be applied to the time domain data, where the windowing and thresholding discussed previously represents a binary or step-like weighting. Weighting procedures may be applied to individual or across multiple decomposed data sets prior to integration and gridding of the time domain data. For example, the temporal data associated with the entire time domain readout period, or with one or more temporal decompositions, may be weighted by a linear ramp or by more complex temporal weightings such as piecewise combinations of linear ramps and unity weights, polynomial functions, or exponential functions. These weightings may be used to accentuate the spatio-temporal encoding via the relaxation dynamics. Smoother or more continuous weightings may provide more flexibility in or more favorable conditions associated with the SNR-resolution tradeoff intrinsic in relaxation weighting as discussed herein. The ability to tradeoff SNR and resolution via temporal weighting is a second method of trading off SNR and resolution in pulsed MPI, independent, for example, of the SNR-resolution tradeoff possible in choosing excitation amplitudes when using direct integrated gridding reconstruction methods.

Figure 32:
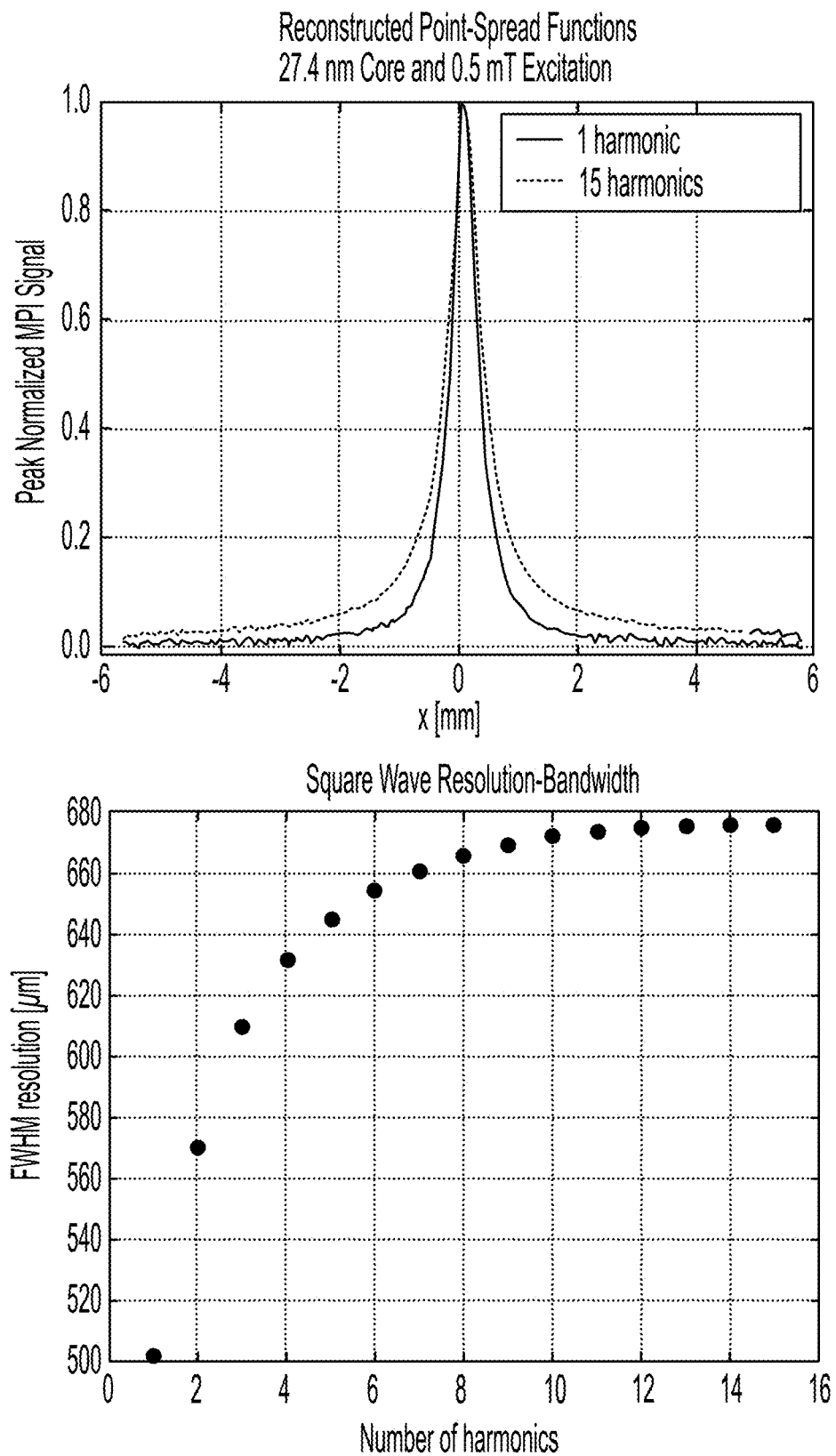
FIG. 32 shows experimental data using filtering to improve resolution by using a reduced receive bandwidth in a pulsed MPI context, including experimental peak signal and FWHM as functions of receive bandwidth.

In some embodiments, filters may be applied to achieve relaxation-weighted improvements in resolution. In canonical, single-tone continuous wave systems, it is well established that higher harmonics of the fundamental excitation frequency are associated with higher spatial frequency information in the image domain, which leads to a fundamental resolution-receive bandwidth tradeoff in which increasing the overall received bandwidth is required to improve resolution and vice versa. However, due to the effect of relaxation and the use of quiescent half-periods long enough to establish steady-state magnetization, we can have a very different relationship in pulsed MPI where retaining only the data associated with a small subset of the lower frequency signal bandwidth can lead to improved resolution, as shown in FIG. 32 for a square wave excitation embodiment.

The signal from tracer farther from the FFR isocenter is characterized by signal that both occurs earlier in the readout period and which is also generally and relatedly characterized by temporally more rapidly varying signal components. From a Fourier domain perspective, this means higher frequency components. Thus, relaxation generally admits a spatio-frequency separability. Time-domain or frequency domain filters (after application of a Fourier transform) may also be used to improve resolution, similar to the application of temporal windows. Unlike many of the time-domain methods described previously, these frequencies may allow for improved resolution without loss of SNR. In some embodiments, it may be possible to improve resolution and SNR simultaneously. This is possible because, while filtering out data associated with higher harmonics does generally remove information and thus signal intensity, it also removes noise due to a reduced bandwidth. If the reduction in noise is greater than or equal to the loss in signal, we maintain or exceed the original SNR. In general, the exploitation of relaxation information in reconstruction may be provided by simple temporal windowing, filtering, or both.

Certain pulsed excitation waveforms may be viewed as simultaneous excitation of the tracer distribution with the fundamental frequency of the periodically repeating exciting waveform (e.g., square wave) along with higher harmonics per the Fourier decomposition of the particular excitation waveform. In this context, the received time domain response signal from the tracer will also be concentrated in small bands surrounding the harmonics of the fundamental frequency. The size of the bands around each harmonic is dictated by other features of the system such as the shift field slew rates. This leads to a similar receive bandwidth structure as in the canonical single-tone continuous wave systems. But as FIG. 32 illustrates, we can have a very different relationship between signal intensity, resolution, and bandwidth. In the square wave embodiment of FIG. 32, high quality images can be constructed from only a single small band around the fundamental harmonic. It is also possible to select one or more bands around the other harmonics and FIG. 32 shows experimental relationships between number of harmonic bands included and 1D image FWHM and peak signal intensity. We see the opposite relationship between resolution and bandwidth as that observed in canonical continuous wave MPI—worsening resolution with increasing receive bandwidth. Such an approach leverages the same relaxation spatio-temporal encoding exploited by temporal windowing and related time-domain operations described previously, but is implemented through use of time domain filters rather than point-wise multiplicative windows. In other embodiments, pulsed excitation waveforms may be used such that a description of the received bandwidth as small bands around harmonics of some fundamental frequency is not appropriate. Nonetheless, in these embodiments, the same spatio-temporal and spatio-frequency coupling with relaxation may pertain and provide improved resolution with reduced receive bandwidth.

In general, relaxation weighting, windowing, filtering, or more general decompositions of the time domain data may be used to generate many images of differing resolutions and SNR which may be later combined into one or fewer images using, for example, multi-resolution image processing techniques. The windows and decompositions used may be non-overlapping or may include overlapping. It is also possible and may be desirable to formulate system matrix approaches to relaxation-weighted imaging, similar to that described earlier for the general case. In the case of relaxation-weighted system matrix reconstruction, a transformation of the data prior to construction of the system matrix, such as using x-space gridded and windowed and/or filtered point source images as the matrix rows or columns will be required. In this manner, a single calibration dataset taken to construct a system matrix may be used to construct many different system matrices, including the cases with and without relaxation weighting/filtering. The raw data associated with a sample scan will need to be transformed accordingly prior to solving the inverse formulation.

Relaxation Image Reconstruction

In general, magnetic relaxation information is directly encoded in the received time domain signal in pulsed MPI. This magnetic relaxation information may be measured, fit, quantified, or otherwise characterized. This quantification can be done without the use of gradient fields in a non-imaging, sensor, or spectral format or may be performed in the context of gradient fields to produce relaxation images and/or 4D imaging data sets. When producing relaxation images, measures of magnetic relaxation phenomena are gridded to image space locations based on the known trajectory of the FFR isocenter to create images of relaxation with information distinct from and largely or completely orthogonal to tracer density images. With some encoding regimes, it is possible to associate a relaxation map, as a function of applied field, to each pixel or voxel in the image space. If no gradient fields or FFR structure is present, a relaxation map as a function of applied field that is representative of the entire sample volume may be rapidly produced. In other embodiments, a 4D dataset describing tracer density as a function of space and a relaxation-associated variable may be provided. In some embodiments, it is possible to use system matrix methods to construct relaxation images. Partial x-space gridding and fitting, measuring, or quantification of dynamic parameters may be desirable in the construction of a suitable system matrix.

In MPI, magnetic relaxation of the tracer may be characterized by multiple and possibly interacting phenomena, for example Neel, Brownian, or ferromagnetic physical relaxation processes. A distinction may also be made between faster magnetic relaxation processes and slower ones in heterogeneous scenarios, regardless of the specific nature of the relaxation physics. Pulsed MPI encoding admits multiple ways of encoding relaxation information, including with respect to these different components, such that reconstruction processes can observe, query, or accentuate different aspects of magnetic relaxation.

In general in pulsed MPI, and especially when using tracers with larger magnetic core sizes, magnetic relaxation phenomena may be sensitive to local microenvironmental processes and conditions. Variables such as viscosity, pH, reactive oxygen species concentration, biochemical state, tracer binding events, state or viability of the cell when a tracer is used to label cells, the kinetics or dynamics of various biochemical processes, and many others may all affect the magnetic relaxation properties of the tracer. This may be especially true when a tracer exhibits significant Brownian relaxation phenomena in which the tracer physically rotates, including both the magnetic core and outer shell, in the process of aligning with the local applied field. The temporal dynamics of a tracer undergoing Brownian relaxation are a strong function of both the applied field strength which acts as a magnetic torque and any sources of rotational drag. In pulsed MPI, when a substantially constant period of the excitation field is applied, the magnetization of the tracer distribution evolves toward a new steady-state based on the interplay between the magnetic torques imparted by the FFR structure and local microenvironmental conditions. When the same pulsed excitation is applied repeatedly at different mean locations of the FFR isocenter, then any differences in local microenvironmental variables of interest will provide contrast in terms of the observable magnetic relaxation. Many of these variables may be associated with physiologic processes of interest and may therefore directly or indirectly encode physiologic contrast into the MPI signal. When a relaxation image is reconstructed from these data, physiologic contrast not observable in the tracer density image may be provided.

Figure 34:
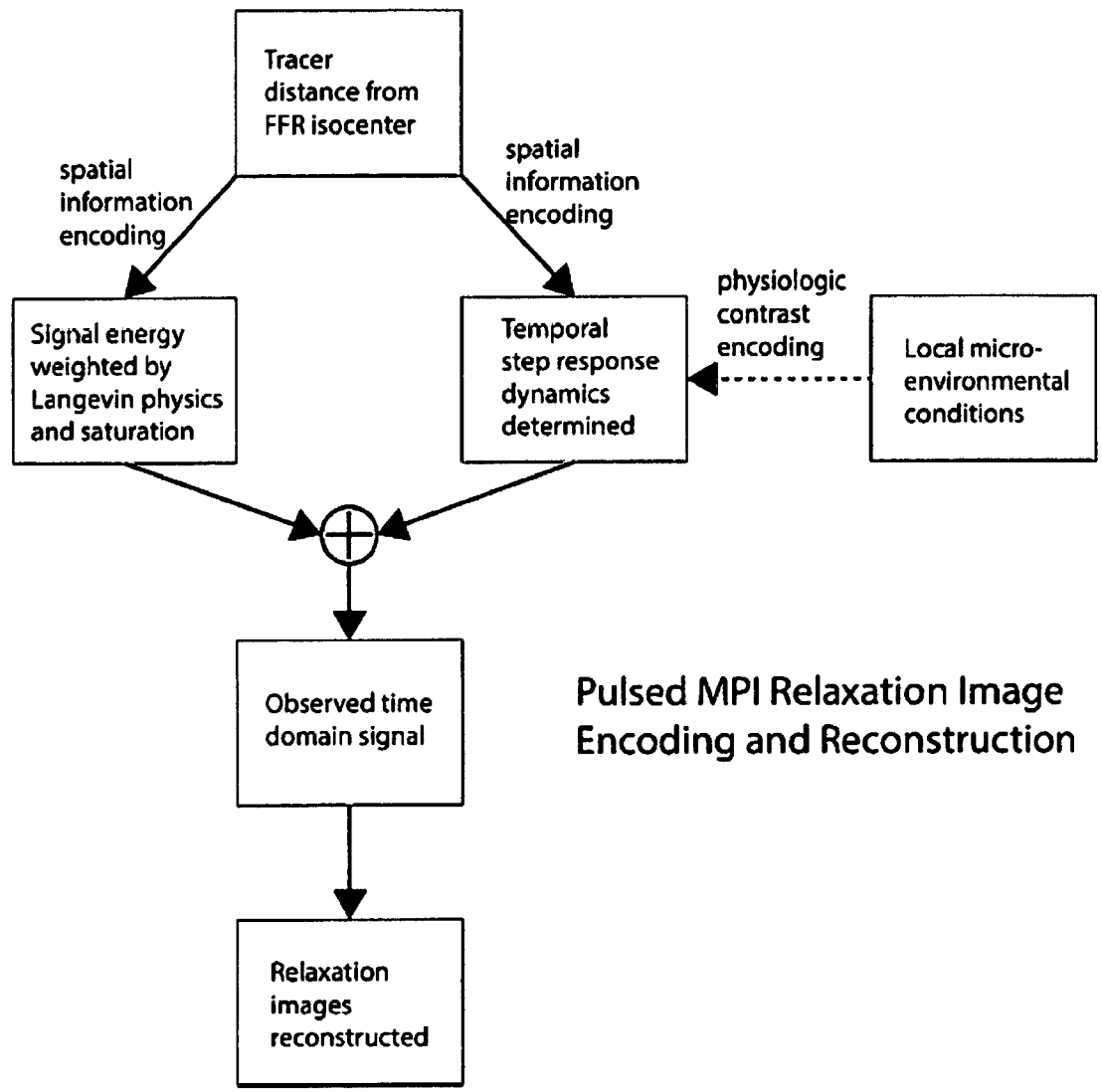
FIG. 34 shows a schematic organization of encoding of relaxation information in pulsed MPI and associated reconstruction methods according to an embodiment of the current invention.

FIG. 34 illustrates key features of the encoding of relaxation information when using pulsed MPI waveforms and how this encoding leads to the ability to reconstruct relaxation images. As in the case of tracer density imaging, spatial information about the tracer distribution is encoded both via Langevin saturation phenomena and temporally in the signal dynamics of readout periods. Langevin physics mean that, regardless of relaxation properties, tracer far away from the FFR isocenter contributes little or no signal energy to the time domain signal associated with a given pulsed excitation. For tracer near enough to the FFR isocenter to contribute non-trivial signal energy, the contributions will vary based on distance from the FFR isocenter such that tracer closest to the FFR isocenter and associated with lower total applied field strengths will undergo relaxation characterized by longer relaxation times while tracer farther away will undergo relaxation characterized by shorter relaxation times. In general, the time-domain signal associated with a given pulsed excitation readout period will be a weighted mixture or superposition (from volumetric integration when using inductive signal reception) of tracer impulse responses following relaxation processes determined by their position relative to the FFR isocenter and local microenvironmental conditions and also weighted or scaled by distance from the FFR isocenter by Langevin physics. The impact of local microenvironmental conditions on relaxation dynamics may provide a strong coupling of physiologic information into the pulsed MPI signal.

Relaxation images so constructed may have various post-processing steps applied to accentuate or identify imaging aspects of interest, for example, particular physiologic contrast or signals of interest. In some embodiments, thresholding of the relaxation image may be used to separate distinct phenomena of interest or to colorize the image. It is also possible to combine relaxation images and tracer density images, possibly constructed from data from the same scan, into one or more colorized images.

Direct Response Gridding

In some embodiments, the raw time domain signal associated with each readout period directly encodes a magnetization impulse response. For example, in the presence of a substantially constant period subsequent to a rapid transition, the magnetic tracer distribution will evolve to a new steady-state magnetization distribution in a step response-like manner. The time derivative applied by use of an inductive receive coil will realize an impulse-like response observable directly in the raw time-domain signal. In these circumstances, one or more characteristic relaxation parameters may be measured or fit for each readout period and gridded or interpolated onto a regular pixel or voxel grid to form a relaxation image. In some embodiments, the image domain grid point associated with each step is the known FFR isocenter location during that step.

Square Wave-Like Relaxation Map or PSF in the AWR

Figure 35:
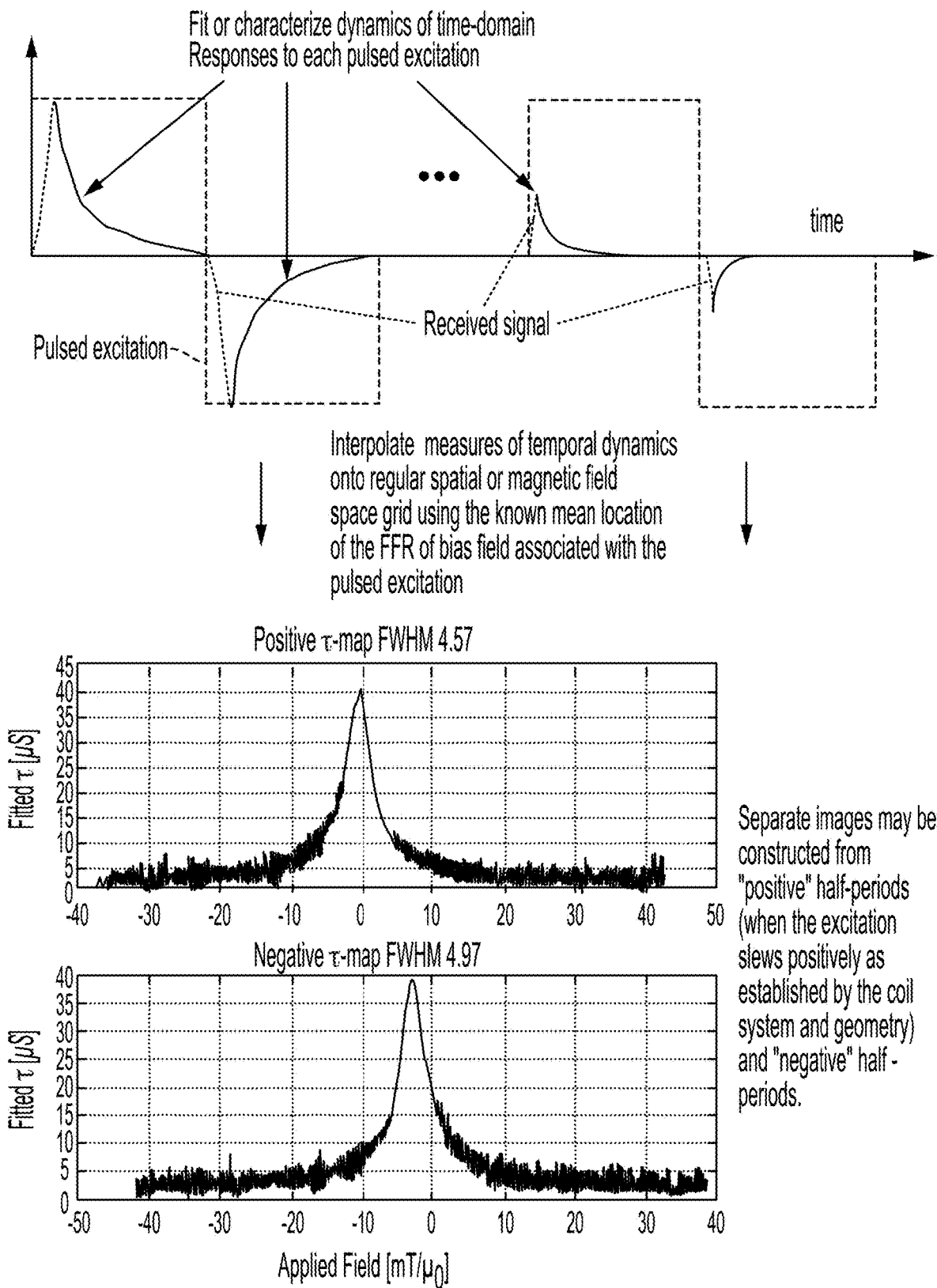
FIG. 35 is a diagram illustrating relaxation image reconstruction by gridding of experimental relaxation image data to mean FFR locations with pulsed excitation according to an embodiment of the current invention.

FIG. 35 illustrates one embodiment of relaxation imaging using a square wave-like pulse sequences encoding and reconstructed as described in FIG. 24 and FIG. 25. In this embodiment, a square wave excitation leads to alternating time domain impulse responses. Each of these impulse responses is the result of a weighted superposition of relaxation phenomena associated with tracer near the FFR isocenter. In general, individual and constituent relaxation responses are determined by distance from the FFR isocenter and local microenvironmental conditions and are weighted by distance from the FFR isocenter according to Langevin physics. In this context, each impulse response may be viewed as a locally aggregated (with respect to the FFR) tracer response. Each impulse response may be quantified, for example, by fitting a single mean, characteristic, or aggregate exponential relaxation time constant to the time domain data associated with each square wave step or half-period. Each fitted value may then be associated with the mean position of the FFR isocenter during the step, or with the total applied field in an excitation with no gradient fields present. As in the case of tracer density imaging, the result is, in general, a many-to-one relationship between sample points and a final imaging grid. An interpolative gridding step may be performed to map the set of measured relaxation times to a final regular grid of pixels or voxels. Relaxation weighting or filtering, as previously described, may be applied prior to measuring, fitting, or quantifying the relaxation dynamics to, for example, localize the measure of the relaxation fit further. In some embodiments using an FFL-based or other projective FFR-based pulsed MPI system, projection reconstruction may first be applied to raw time domain data sets collected at different relative angles between the FFL/FFR and imaging volume prior to fitting dynamic relaxation values and gridding or interpolating the fitted values to x-space. In such a manner, time domain data may be associated with locations resolved in all three spatial dimensions prior to reducing the time domain data to image domain values, which may improve the conditioning of the dynamic fits and better localize true relaxation behavior in 3D space.

An AWR can be used to measure the aggregate relaxation time constant of a sample as a function of applied field strength, as shown in FIG. 35. A square wave-like excitation was superposed with a slow, linearly ramping bias field to sample a large magnetic field of view. This one-dimensional relaxation map, as a function of applied field strength, may be viewed as a relaxation image PSF, analogous to a tracer density PSF similarly constructed and describing how the magnetic relaxation dynamics change as a function of total applied field and/or distance from the FFR isocenter in an imaging context where gradient fields are present. Additionally, this relaxation map describes how the aggregate tracer sample responds to the aggregate microenvironmental conditions in the sample. Local microenvironmental conditions in the same sample, or across many different samples, may be queried as desired with scans and relaxation map reconstruction when the sample is exposed to different conditions. This process may be used to sense, detect, and quantify the sensitivity of the tracer dynamics and relaxation PSF to microenvironmental conditions, providing information about the expected contrast available in a relaxation imaging format with a given tracer.

Although in the embodiment shown in FIG. 35 a single representative relaxation time constant was fit per excitation readout, in other embodiments, it may be desirable to fit more than one relaxation parameter. For example, more than one exponential time constant may be fit and one or more exponential amplitudes may be fit along with the time constant or time constants. Such approaches may be desired or well-motivated if the physics of the tracer is governed by multiple processes, such as combined Neel and Brownian processes, if the tracer is heterogeneous in characteristics such as magnetic core size and shell diameter, if any other non-idealities exist, or if spectral decomposition of relaxation is desired for 4D imaging. A single exponential time constant itself is not necessarily precise, as it is known that the time domain signal will be a weighted average or mixture of various response times associated with tracer at different locations and subject to different conditions. However, simple models such as a single exponential time constant may effectively and robustly capture the dynamics and provide very meaningful contrast from a physiologic or molecular imaging point of view.

In general, relaxation dynamics may be fit against phenomenological or physical models of magnetic tracer relaxation more complex than a simple linear first order process described by an exponential time constant. In some embodiments, relaxation parameters other than time constants may be fit, measured, or derived. For example, parameters such as peak delay time, FWHM, or finite support time as defined by some threshold such as an SNR threshold may be more instructive, better characterize the temporal dynamics, or accentuate contrast of interest in relaxation imaging.

Steady-State Recovery Image Reconstruction

Figure 20:
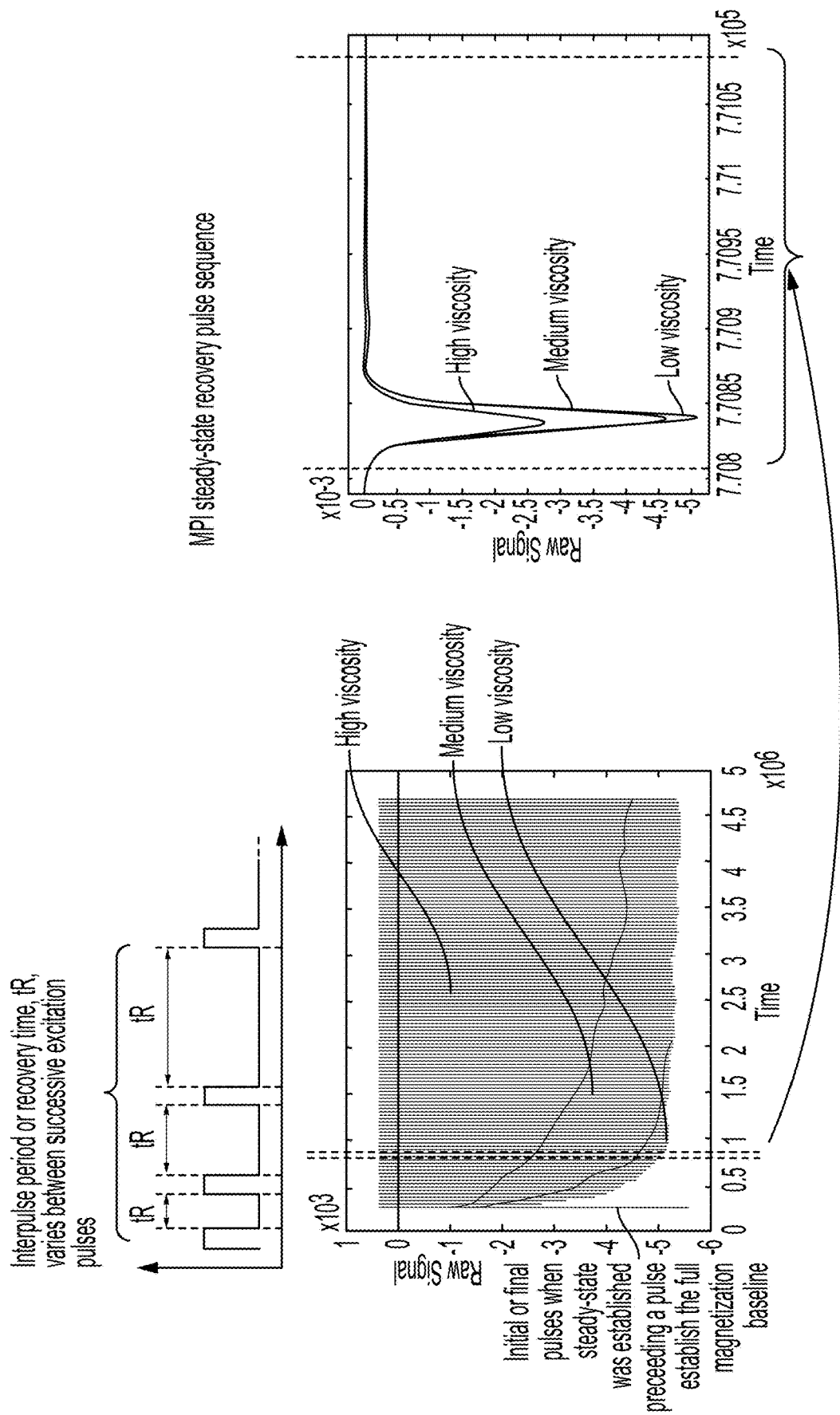
FIG. 20 shows a steady-state recovery sequence and AWR data according to an embodiment of the current invention.

In some embodiments, pulse sequences may query the time to achieve steady-state for tracers near a given mean location of the FFR using a steady-state recovery pulsed excitation waveform. Embodiments of this type of encoding and associated raw data are shown in FIG. 20. In this case, a measure of steady-state recovery or relaxation times may be quantified or fit. Steady-state recovery excitation allows much longer or total time constants to be measurable or detectable in the presence of much faster time constants and associated physical phenomena acting simultaneously. Some MPI tracers under certain conditions may be characterized by simultaneous relaxation processes differing by an order of magnitude or more in characteristic time. Furthermore, the slow process may be responsible for a significant fraction of the total energy of the tracer response, but the dynamics of this process may be difficult to capture in the raw time domain signal when juxtaposed to the fast process and a noise floor. In this case, steady-state recovery encoding provides a robust method to quantify the slower process and/or the total or combined relaxation time associated with a process.

Figure 36:
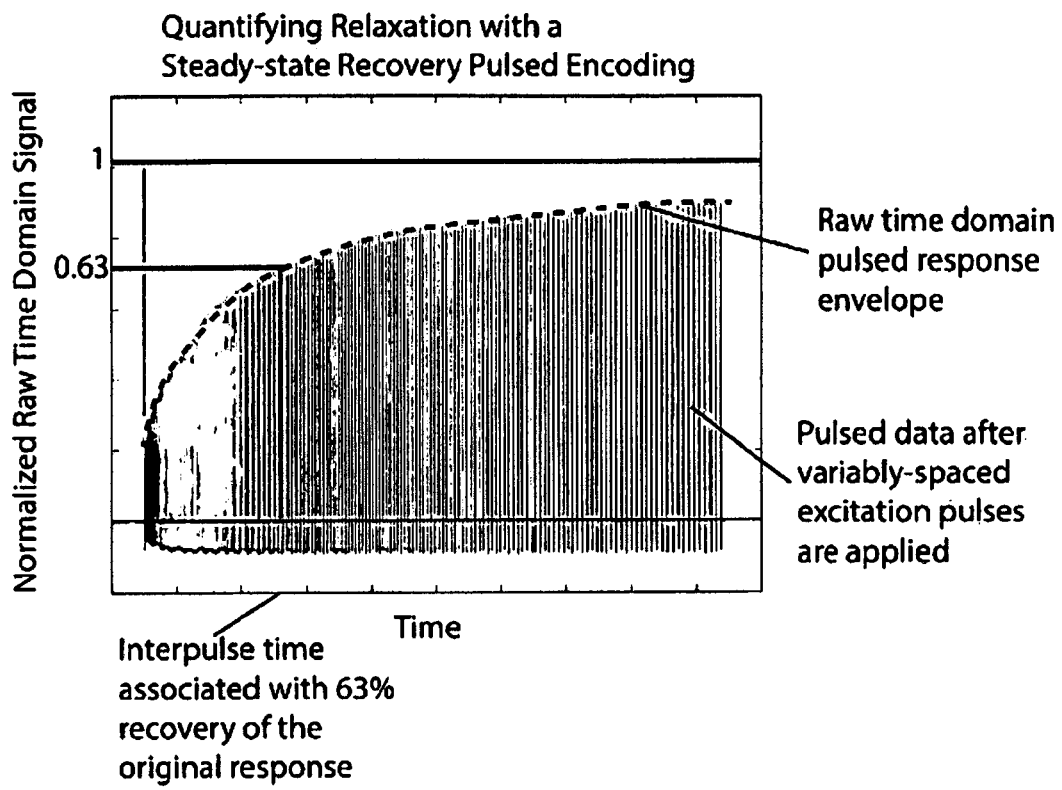
FIG. 36 shows steady-state recovery quantification of tracer magnetic relaxation according to an embodiment of the current invention.
Figure 37:
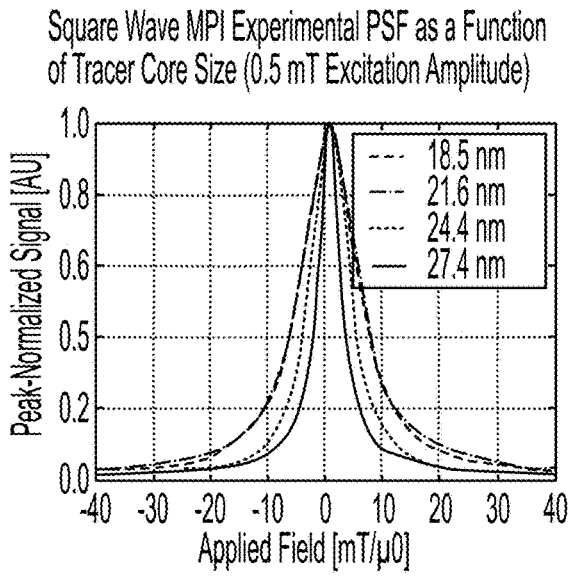
FIG. 37 shows square wave reconstructions for different particles, excitation amplitudes, etc. according to an embodiment of the current invention.
Figure 37:
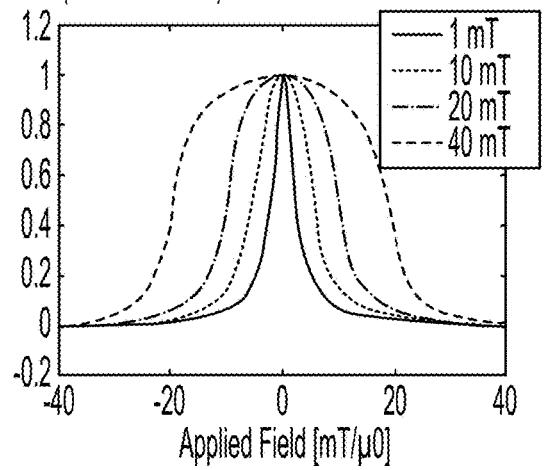
Figure 37:
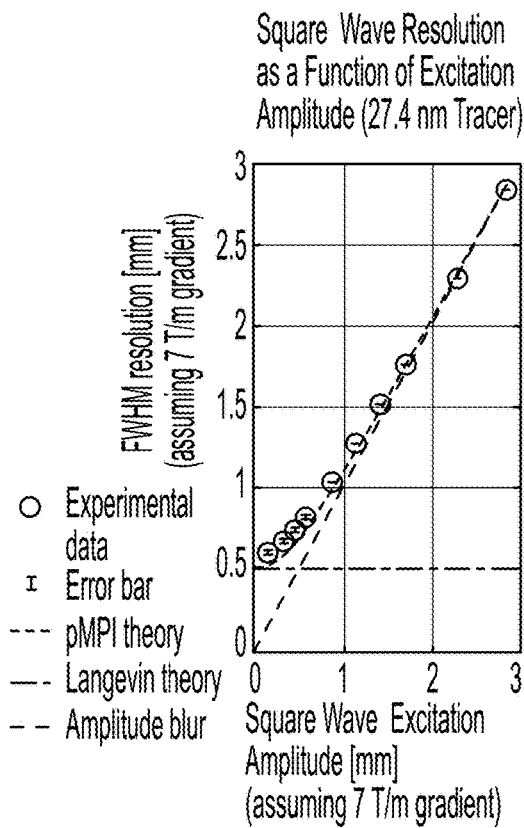
Figure 37:
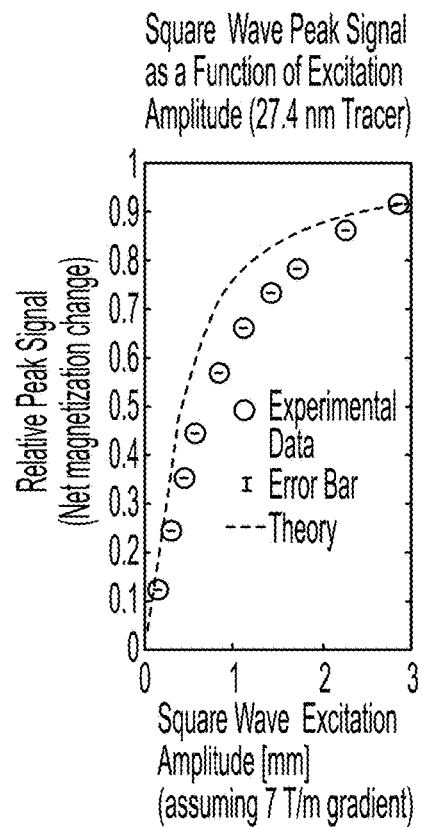
Figure 38:
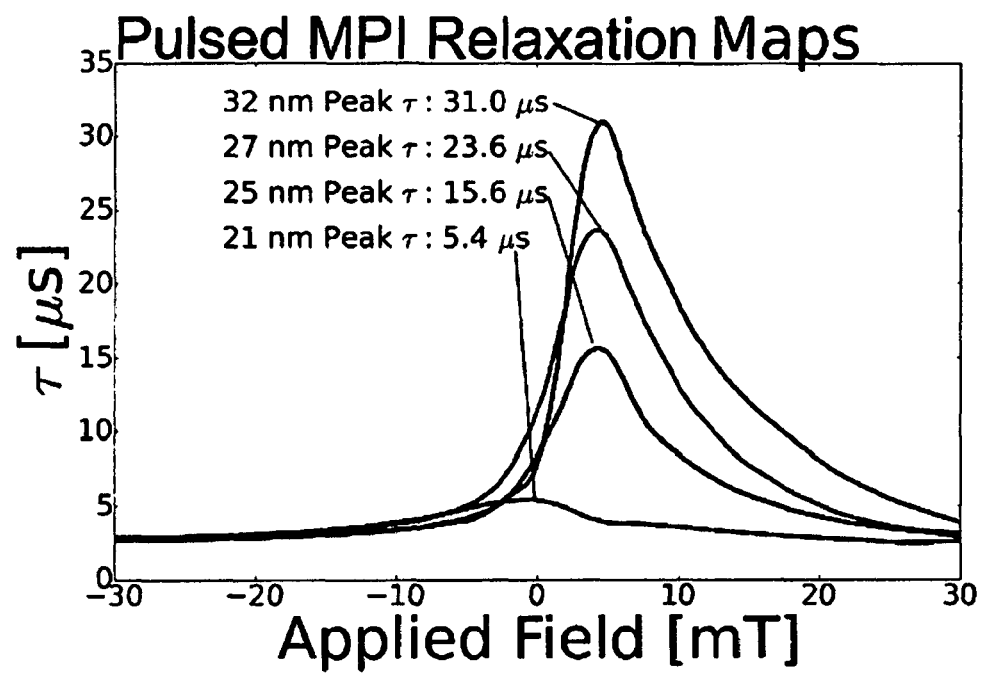
FIG. 38 shows relaxation map reconstructions for particles of different magnetic core size according to an embodiment of the current invention.
Figure 39:
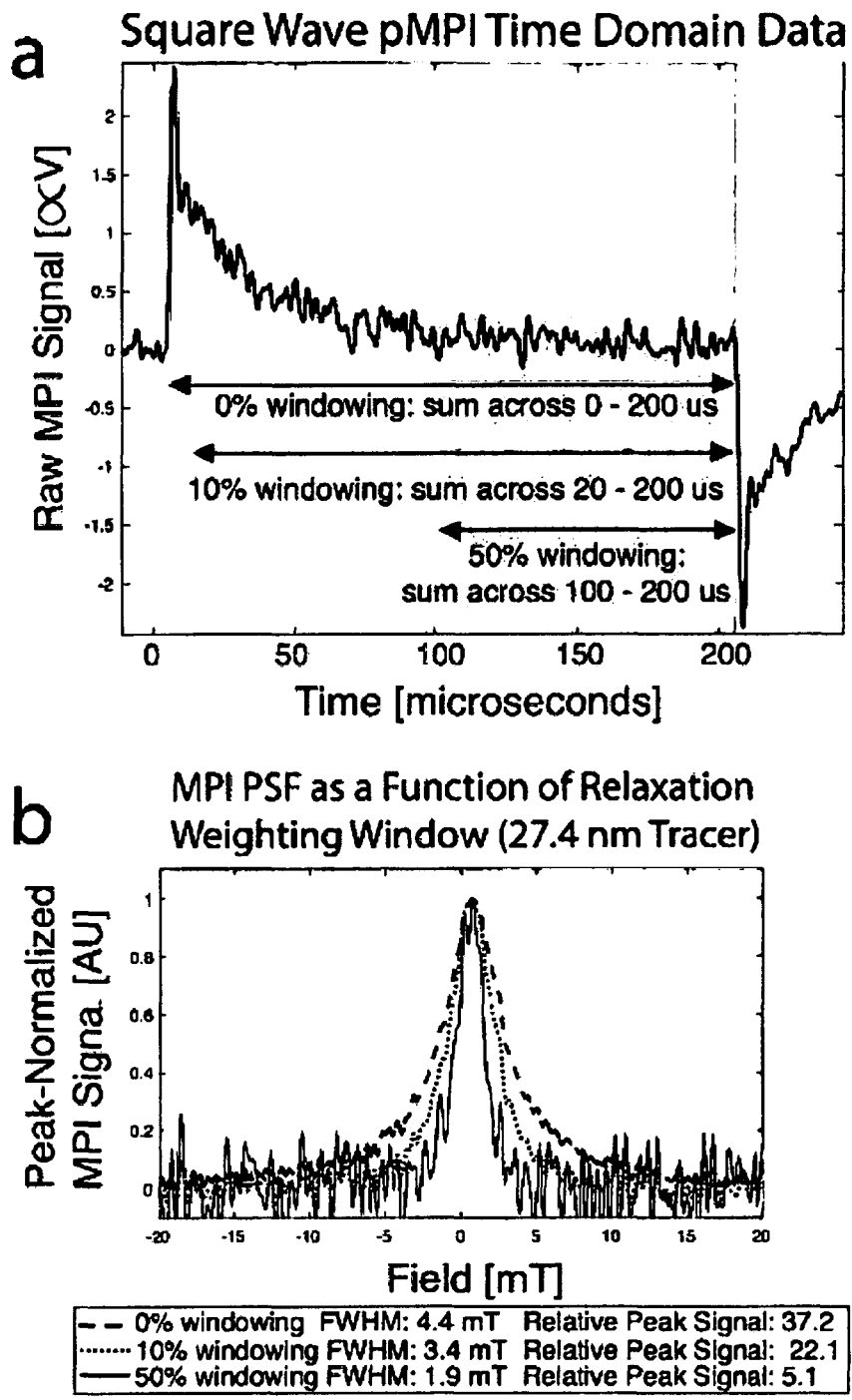
FIG. 39 shows relaxation-weighted PSFs with different windowing options according to an embodiment of the current invention.

FIG. 36 shows how steady-state encoded signal may be processed to yield quantified relaxation information. Per mean location of the FFR, or as a standalone sensing system without gradients, a series of pulses with variable interpulse-period are applied. The output raw data contains characteristic signal impulse responses associated with each pulse. Early and/or short duration interpulse-periods between excitation pulses disallow the tracer distribution to reach steady-state prior to the next excitation. In this case, the distribution will be in some intermediate state between that associated with each pulse and that associated with the interpulse period. Pulses applied after shorter duration interpulse periods will lead to signal spikes with lower total energy, e.g., lower peak values and/or area under the curve. This is readily seen in the raw data of FIG. 20 and FIG. 37. The full steady-state energy may be associated with an initial pulse, applied after steady-state associated with the interpulse period FFR location is achieved, or by a final pulse applied after an interpulse period guaranteed or known to achieve steady-state, or both. Many pulses may be applied between the first and final pulses, with variable interpulse periods to sample the relaxation dynamics of the tracer distribution. In some embodiments, imaging applications will use relatively fewer pulses to ensure reasonable total scan times. In some embodiments, non-imaging (no gradient) applications will use many more pulses to more densely sample the relaxation dynamics.

Many methods may be used to quantify the relaxation dynamics queried by a steady-state recovery excitation. In some embodiments, an envelope will be fit to the raw data as shown in FIG. 36. For example, an exponential may be fit such that the exponential time constant of the envelope corresponds to the relaxation time associated with the tracer via steady-state encoding analysis. In other embodiments, a characteristic time will be directly fit or interpolated from the raw data and/or an envelope fit to the raw data. For example, the interpulse time required to achieve 63% of the steady-state peak or energy value may be directly calculated or interpolated and may be reported as a characteristic time constant.

Excitation Along the Line

In some embodiments pulsed excitation will be directed along the line of an FFL. In this regime, the line is not translated in the orthogonal plane but instead transitions from an FFL to an LFL or from an LFL at one strength or polarization to an LFL at another strength or polarization. The mean location of the FFL or LFL in the orthogonal plane is constant regardless of the excitation pulses applied in the line direction. In some embodiments, it is possible to query relaxation of tracer along the line at different applied field strengths. Similar to relaxation maps constructed with pulsed encoding in an AWR or when no gradient is present, the relaxation dynamics of the tracer distribution may be probed against the total applied field strength with an excitation pulse sequence. However, this information is now spatially localized by the excitation line. This excitation may be applied at different mean locations of the FFR and/or FFL. Either in a projection mode or following full tomographic projection reconstruction, 1D relaxation maps or other non-scalar values may be associated with individual pixels and/or voxels. In general, these multi-value data sets may be reduced to scalar values of merit to yield scalar relaxation images as in other relaxation image embodiments. These data may also be reduced or transformed into 4D data sets describing tracer intensity as function of space and a temporal relaxation-associated variable.

Temporal Decomposition

As in the case of tracer density imaging, the spatio-temporal encoding inherent to the time-domain signal itself may be used in the construction of relaxation images. The same or similar weighting, windowing, or filtering procedures as applied in relaxation weighted tracer density imaging may be applied to the time domain signal prior to relaxation image formation. In some embodiments, a relaxation parameter of merit, such as an exponential time constant, may be fitted to each of a number of distinct windowed decompositions or distinct filtered versions of the time-domain signal. Because earlier aspects of the readout signal will be weighted more by fast relaxation processes, including those due to particles farther from the FFR isocenter and later aspects by slower relaxation processes, including those due to particles closer to the FFR isocenter, measures of relaxation parameters associated with different windows or filters provide a mechanism of filtering out or selecting for relaxation times associated with specific phenomena. In some embodiments, this procedure will improve the resolution of the relaxation images. In some embodiments, this procedure can be used to filter out or select for distinct relaxation states such as bound versus unbound, regardless of spatial weighting.

4D Imaging

Certain embodiments of forming distinct tracer density images and relaxation state images have been described. Mathematically, these can be described as yielding distinct images of the form rho(x, y, z) and r(x, y, z) where rho corresponds to a scalar tracer density image and r corresponds to a scalar relaxation image. In general, it may also be possible to combine the information more explicitly to form 4D image datasets of the form I(x, y, z, tau) in which a reconstructed dataset contains intensity information about tracer as a function of space and relaxation time. Such a reconstruction would yield a point-spread function (PSF) and images that more fully characterize the MPI process and provides spectral information about tracer dynamics. In some embodiments the scalar intensity variable I collapses to the tracer density rho if the 4D image is projected along the tau direction. In some embodiments, windowed decomposition techniques applied to the raw time domain data may be used to form such a 4D image dataset. In other embodiments, mathematical tools such as Laplace transforms may be leveraged to recover, deconstruct, or reconstruct relaxation time or relaxation spectral data. In other embodiments, the raw time domain data may be projected onto a suitable basis set, or transformed and then projected onto a suitable basis set. The basis set may, for example, be associated with known physical relaxation processes that characterize a tracer.

Postprocessing Approaches

Various postprocessing techniques may be leveraged in the context of pulsed MPI. In general one or more images may be reconstructed by the signal processor for each scan and one or more scans may be associated with a single sample. A set of images so obtained may be processed in various ways to produce a final output for a user. For example, single images may be processed, filtered, or thresholded. Multiple images may be similarly processed, filtered, or thresholded prior to being combined in some manner.

Multiresolution Image Combination

In some embodiments, a plurality of images may be obtained from encodings or reconstructions that lead to differing native resolutions and/or SNR levels. For example, the use of dynamically varying gradients, multiple scans taken at different fixed values of gradient magnitude, the use of dynamically varying pulsed excitation amplitudes, multiple scans taken at different fixed values of excitation amplitudes, and/or scans taken with different pulsed MPI encodings, e.g., through different magnetization preparation designs, may all be combined to produce a smaller set or single image. The final image or images may be designed to maximize one or more of resolution, SNR, and image contrast and may be dependent on the desired application.

Density and Relaxation Image Combination

In some embodiments, one or more distinct density and/or one or more distinct relaxation images may be combined into one or more new images. In some embodiments, relaxation information will be used to colorize a tracer density image to improve image contrast and map relaxation information onto the tracer density images. Relaxation information may be directly overlaid onto density images and/or anatomical reference images from another modality with a continuously varying color map. In some embodiments, continuously varying relaxation information may be thresholded or mapped onto distinct colors by other means. For example, forward model-based algorithms may be employed to unmix relaxation species of interest, such as MPI tracers in a bound or unbound state or in the separation of distinct tracers if multiple are applied to a sample volume. These results may be used to form standalone images or applied and overlaid onto density images as a color mapping.

Projection and Slicing of 4D Data

In some embodiments, signal processing and reconstruction will provide 4D MPI datasets where an MPI intensity value is mapped against three spatial coordinate variables and a temporal relaxation variable. Projections along various dimensions may allow seamless interrogation of the information-rich dataset. For example, projection along one or more spatial dimension will allow for visualization of relaxation spectral information against the remaining spatial dimensions. Projection along the relaxation dimension may recover a tracer density image. Slices through the 4D data set may provide easily visualized 3D data sets such as MPI intensities localized in space as one steps through the enumeration of the relaxation spectral variable.

Applications of Pulsed MPI Encoding

Enhanced Imaging through Use of Larger Core Tracers

Using pulsed encoding and reconstruction techniques, all current applications of MPI may be improved in terms of imaging parameters such as resolution, SNR, and image contrast. For example, use of tracers with mean core sizes larger than 25 nm with pulsed MPI techniques can improve resolution in current areas of active MPI development such as stem cell tracking, cancer diagnostic imaging, lung ventilation and perfusion imaging, cardiac and angiography applications, stroke diagnostic imaging, and perfusion imaging such as cerebral blood flow (CBF) and cerebral blood volume (CBV).

Examples of Applications of Pulsed MPI

The unique aspects of pulsed MPI such as quantification of relaxation information, the prospect of 4D imaging, and the ability for magnetization shaping through magnetization preparation may provide for new, previously unforeseen applications of MPI. With the ability to robustly quantify relaxation information, and especially that associated with environmentally-sensitive physics such as Brownian relaxation, these pulse sequences may be used across a broad range of new molecular imaging applications. Pulsed MPI pulse sequences can allow for all of the following, optionally with tracers with a mean magnetic core size of 25 nm or more: in vivo viscometric imaging, pH imaging, inflammation imaging, reactive oxygen species imaging, imaging of binding events using functionalized tracers, design and use of MPI magnetic switches, observation of biochemical kinetics via functionalized or specialized tracers, elucidating bleeding in the body, infection imaging, diagnosis of pulmonary embolism and perfusion disorders of the lung, sentinel node biopsy.

In some embodiments pulsed MPI methods and apparatuses are used to image and/or quantify relaxation properties for ex vivo samples of interest. These samples may have originated from whole organisms in which MPI tracers were introduced, e.g., by systemic delivery or local injection, or MPI tracers may have been introduced in a separate step after harvesting. These samples may include tissue and organ samples, biological fluids, and other biologically-derived samples. These samples may also include non-biological samples of interest such as tracer samples. In some embodiments, pulsed MPI methods and apparatuses are used to image and/or quantify relaxation properties for live animal subjects after MPI tracers of interest are introduced, such as by, but not limited to, systemic injection into the circulatory system or direct tissue injection. In some embodiments, pulsed MPI methods and apparatuses are used to image and/or quantify relaxation properties for human subjects after MPI tracers of interest are introduced, such as by, but not limited to, systemic injection into the circulatory system or direct tissue injection.

Figure 40:
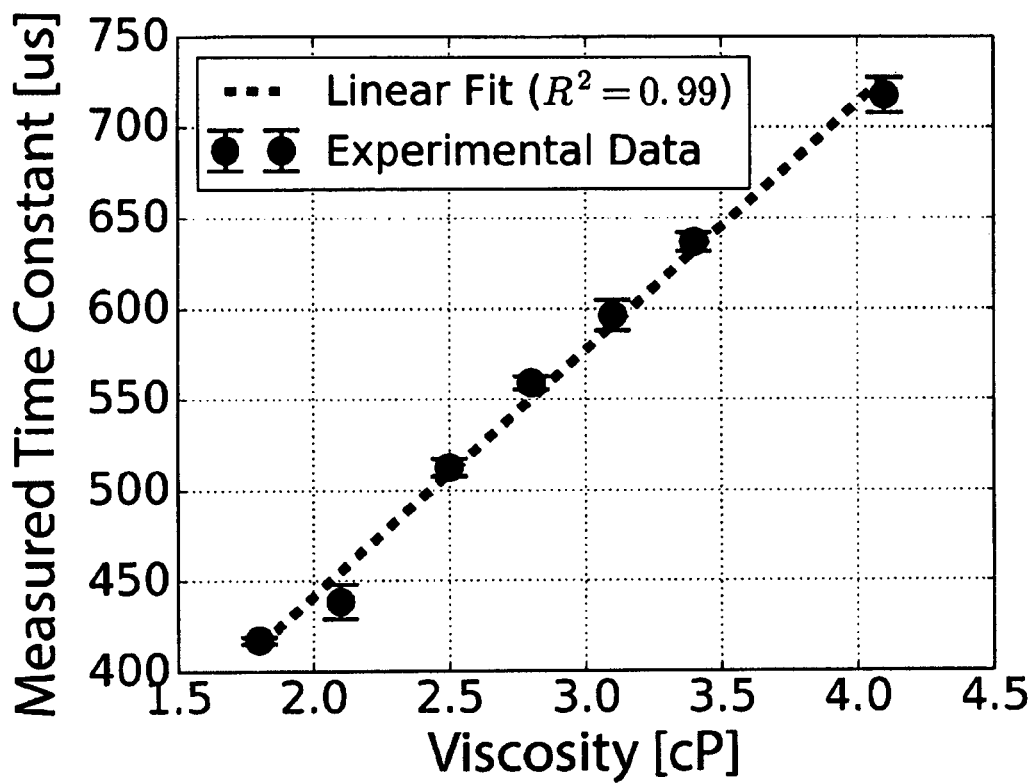
FIG. 40 illustrates experimental viscometry using pulsed MPI to correlate measured relaxation time constants to fluid viscosity using an MPI tracer exhibiting Brownian physics according to an embodiment of the current invention.
Figure 41:
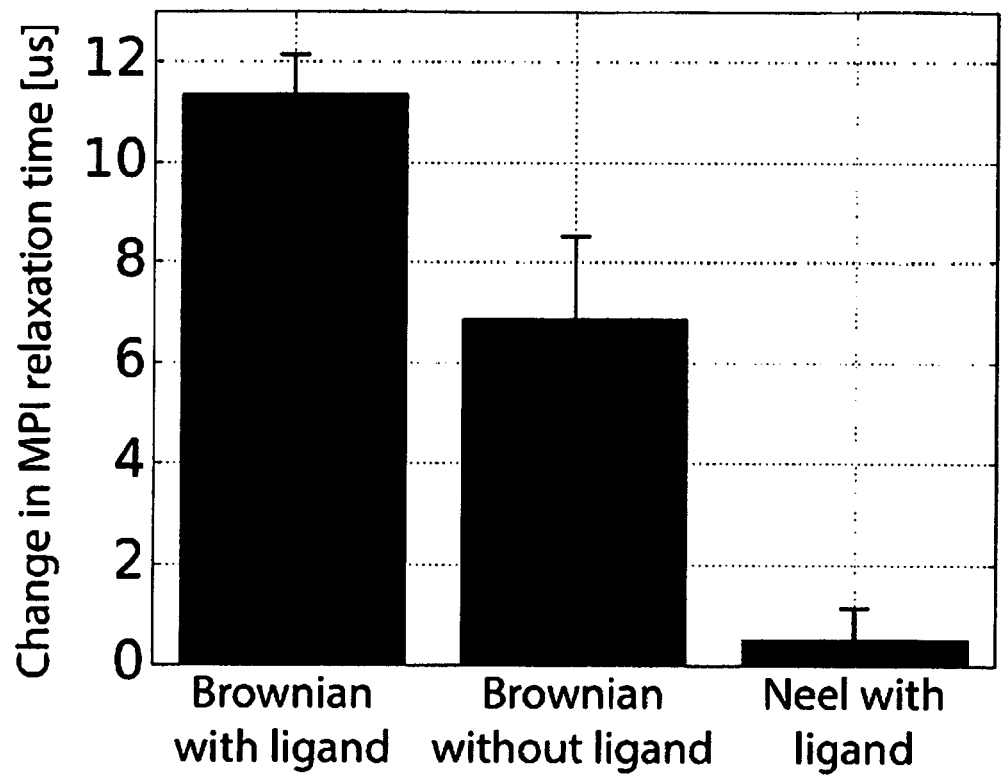
FIG. 41 provides experimental data showing sensitivity of MPI particles to the introduction of a ligand-containing mixture according to an embodiment of the current invention. Tracer with significant Brownian physics show appreciable change when a ligand mixture is added and for which the tracer has a receptor (left). Even without a receptor, the Brownian tracer shows a different relaxation behavior after the addition of the ligand mixture due to changes in viscosity and other states of the microenvironment. A tracer without significant Brownian nature and which is Neel dominant shows no sensitivity to changing microenvironmental and binding events.

FIG. 40 and FIG. 41 show experimental data obtained using pulsed encodings and pulsed MPI techniques with an AWR. FIG. 40 shows a robust ability to detect changes in magnetic relaxation for a larger core MPI tracer (>25 nm) as a function of viscosity, across a physiologically relevant range of viscosities. These data indicate the sensitivity and possible physiologic contrast capabilities inherent to relaxation imaging in pulsed MPI. FIG. 41 further illustrates the ability to detect binding events using pulsed MPI relaxation imaging techniques and shows a measured distinction between tracer that responds to binding and that which does not.

Pulsed MPI Hardware

Figure 42:
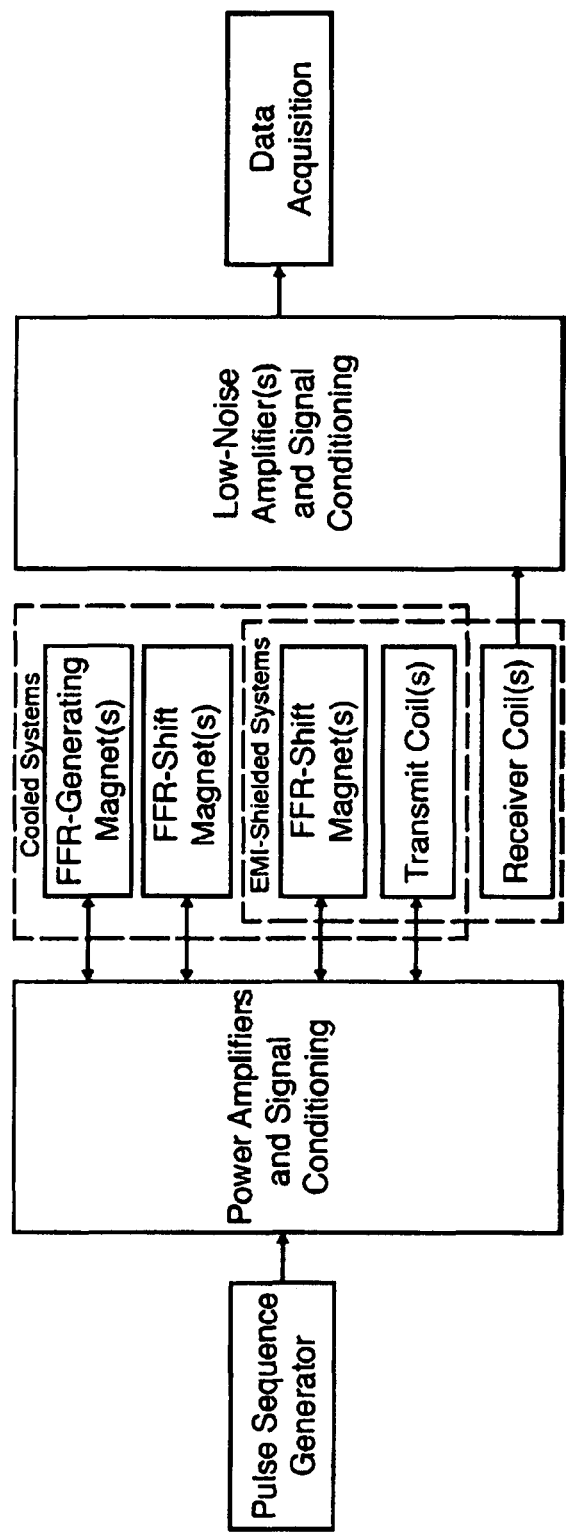
FIG. 42 is a generic electronics block diagram for some embodiments of the current invention.
Figure 43:
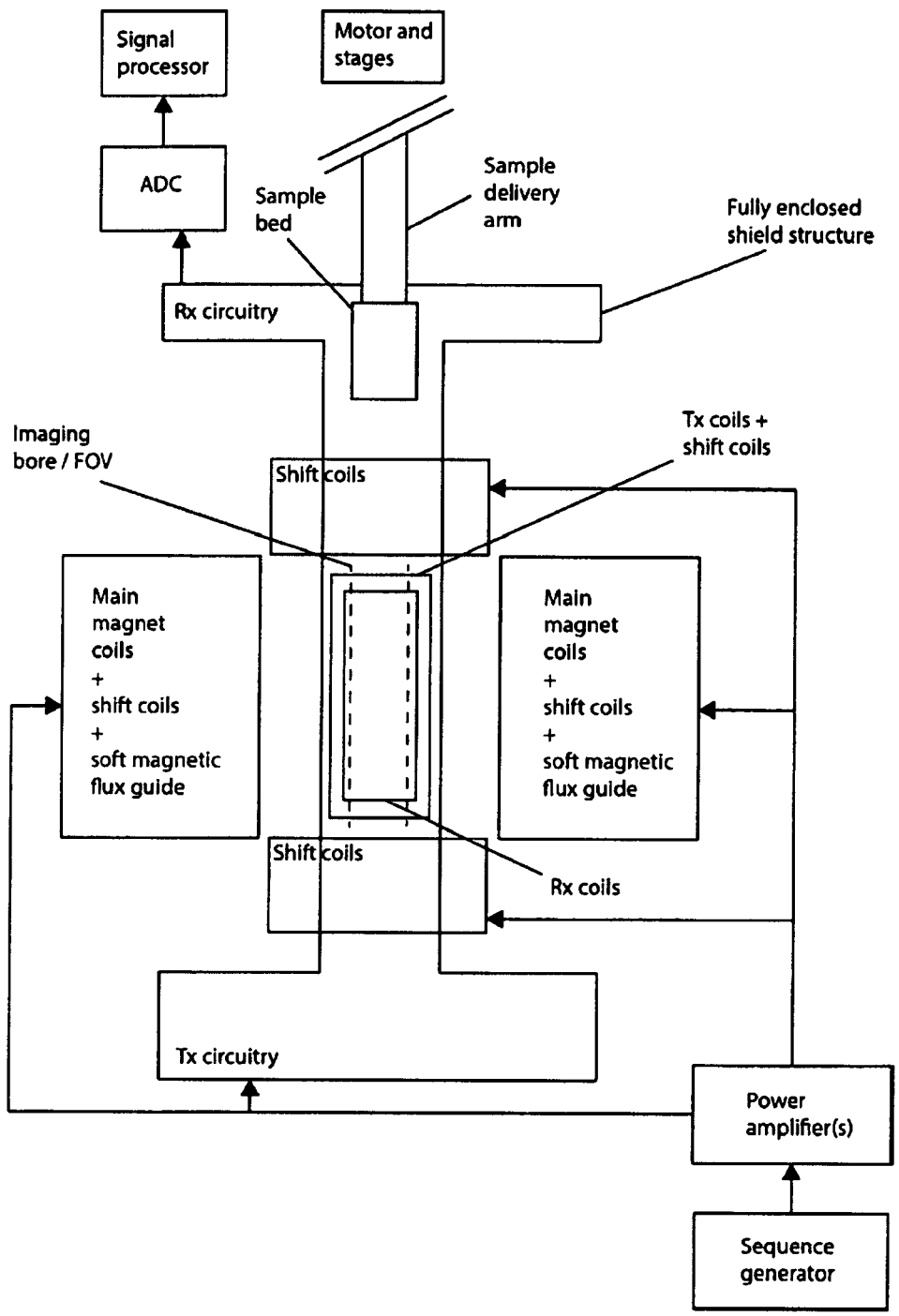
FIG. 43 is a schematic illustration of a pulsed MPI scanner system according to an embodiment of the current invention.

Multiple hardware systems are required to realize pulsed MPI excitation in practice. FIG. 42 describes components and relationships among constituent subsystems in a pulsed MPI scanning system. FIG. 43 further illustrates aspects of an exemplary pulsed MPI scanning system.

Generation of an FFR

Figure 44:
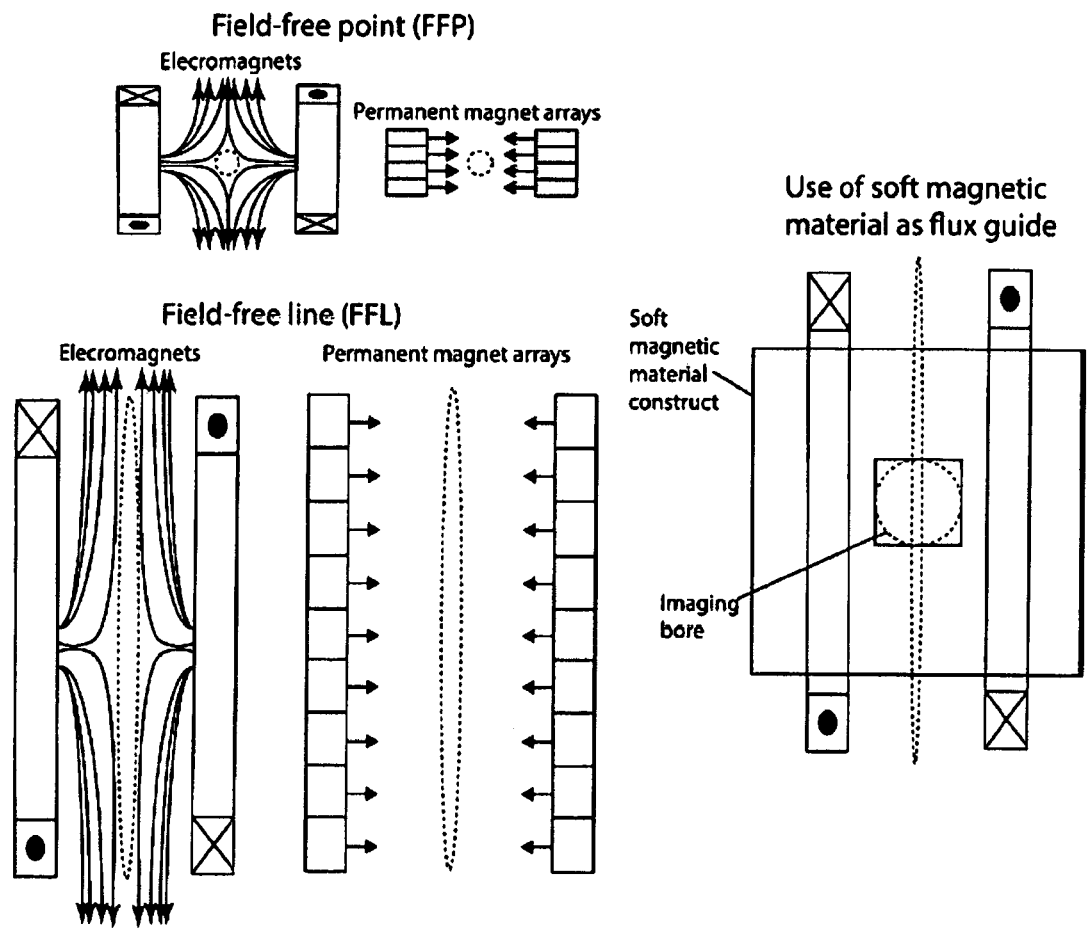
FIG. 44 shows some examples of generating FFRs with magnets and passive flux guides according to an embodiment of the current invention.

A crux of all MPI systems is spatial localization of the signal through manifestation of an FFR structure of some type, as illustrated in FIG. 2. To generate an FFR structure, a typical MPI scanning system contains one or more active or passive magnetic field sources used to generate a particular spatial field pattern that constitute the FFR. The FFR is characterized by containing at least one region in which the applied field is below a tracer-specific saturation value and one region where the applied field is above the tracer-specific saturation value. FFRs often, but not necessarily, contain linear spatial gradients in magnetic field and so transition smoothly and linearly between these regions. The FFR may be a field-free point, field-free line, or of a more general shape as depicted in FIG. 2. The FFR may be produced by one or more active or passive magnetic sources such as electromagnet coils, superconducting magnets, or arrays of permanent magnets as illustrated in FIG. 44. Passive soft magnetic materials such as iron as shown in FIG. 44 may also be used in the design as flux concentrating guides to improve desirable aspects of the FFR pattern such as linear gradient strength at reduced power.

Moving, Exciting, and Manipulating the FFR-Sample Geometry

A typical MPI scan may be thought of as shifting the location of the FFR pattern relative to an imaging FOV of interest to sample the imaging FOV of interest as depicted in FIG. 17. In this exemplary x-space pulse sequence embodiment using an FFL, the mean location of the FFL line isocenter is slowly rastered in the plane orthogonal to the line to acquire a projection image. Rotation of the FFL-sample relative geometry allows multiple projections to be obtained for tomographic projection reconstruction. The cross-hatched regions of the figure illustrate the pFOV regions that are sampled or covered by excitation pulse sequences in the plane orthogonal to the line. Alternatively, in some embodiment, excitation may be entirely in the direction of the line. Shifting waveforms are required to fully sample the larger FOV. These regions are for illustration and or not necessarily to scale. For example, the pFOV region widths may be much smaller in relative size in some embodiments. Furthermore, the specific raster trajectory shown is not limiting. Other raster or Cartesian trajectories as well as radial, spiral, or other types of trajectories may be used to cover the total FOV. pMPI excitation can also be used in developing a calibration or system matrix for system matrix reconstruction methods.

In general, the same magnetic field sources, such as in the case of electromagnets, used to create the FFR pattern may be used to accomplish some or all components of the time-varying FFR trajectory. In other embodiments, distinct magnetic source components provide one or more of these shifting fields. Both of these cases are illustrated in FIG. 43. Small passive or active shim components, such as small electromagnet coils, permanent magnet pieces, or soft magnetic material pieces, may be included in the design to ensure fidelity of the target FFR is maintained during scanning trajectories of interest. It is possible to shift the location of the FFR with respect to the imaging FOV using mechanical motion of the sample relative to the FFR, of the FFR relative to the sample, or a combination of both. It is also possible use a combination of a time-varying magnetic field source or sources with mechanical motion to sample an imaging FOV. For example, in some embodiments, the sample may be mounted on a linear stage driven by a motor which is used to place the sample in the imaging bore and also to provide all or part of the relative shift in one direction during scans. Shift in one or both of the orthogonal axes may be provided by distinct electromagnets as illustrated in FIG. 43. In the case of rotation with projection imaging, mechanical or electromagnet sources may provide the relative rotation between the sampling volume and FFL or more general FFR.

In general, fast (e.g., bandwidths >1 kHz) excitation or drive waveforms may be distinguished from slow shift waveforms (e.g., bandwidths <10 Hz) for conceptual clarity, differences in the way they interact with system components such as eddy-current shielding subsystems, and in consideration of the imaging signals. However, both types of waveforms act to shift or condition the FFR pattern over time, possibly differing substantially in field magnitude and power requirements in addition to speed or slew rates. When using electromagnets to shift linear gradient FFR designs, excitation and shift waveforms are typically applied to coils arranged to produce spatially homogenous, but time-varying, fields. Homogeneous fields will act to shift or translate many FFR implementations in time while maintaining the spatial integrity of the FFR pattern throughout. In some embodiments, such as excitation along the line of an FFL, the FFR is not translated but rather transformed as previously described. When using such homogeneous coils, homogeneity requirements may be on the order of 90% or better, in terms of deviation in coil sensitivity over the imaging FOV, although coils with poorer homogeneity may be used.

Pulsed Excitation Transmit Systems

In pulsed MPI, fast excitation or transmit hardware systems must be capable of realizing time-varying magnetic fields that are described by pulsed waveforms. Whereas a typical MPI trajectory includes a fast, temporally sinusoidally-varying excitation or drive field, some embodiments of the present invention contemplate the use of pulsed excitation waveforms with non-sinusoidal temporal variations that lead to non-sinusoidal scanning trajectories. These non-sinusoidal excitation waveforms may include periodic or non-periodic components in which a specific value of the field is held substantially constant for a period of time as well as rapid transitions through rising and/or falling edges, as well as more arbitrary transient waveform components.

To realize these pulsed waveforms, specific transmit electronics and coil designs are required. The ultimate goal is for the current through one or more excitation coils, and therefore the induced magnetic field, to follow a prescribed temporal trajectory defined by pulse sequences. In particular, the ability to support both substantially constant periods of various durations and rapid transients and/or excitation waveforms with larger bandwidths than the single tone of traditional sinusoidal transmit systems is required.

Linear Amplifier and Low Inductance LR Circuit

Figure 45:
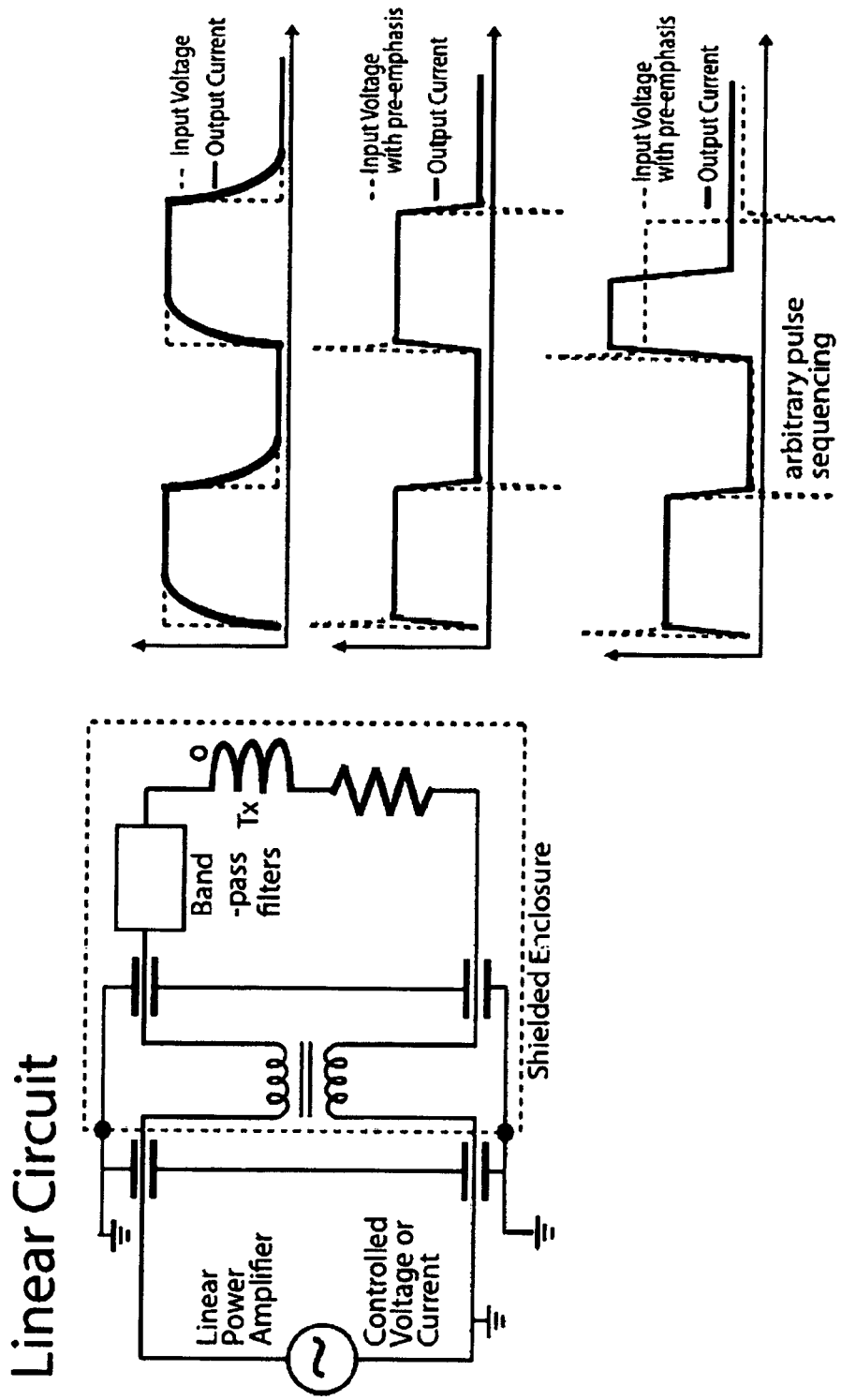
FIG. 45 shows a transmit system for pulsed excitation using a linear power amplifier according to an embodiment of the current invention.

In some embodiments, the transmit, drive, or excitation electronics chain contains an LR circuit powered by a linear amplifier in a non-resonant filter chain that does not substantially alter this inductance as illustrated in FIG. 45. The power amplifier may be run in either controlled voltage or controlled current mode. When operating in controlled voltage mode, pre-emphasis may be applied to the input voltage signal supplied to the linear power amplifier as illustrated in FIG. 45. The requisite voltage waveforms to realize the desired pulsed current waveform, which may include rapid transients and substantially constant periods, are pre-calculated before input into the power amplifier. This may be accomplished by simulation of the circuit, mathematical optimization techniques such as a convex optimization formulation, and/or circuit characterization by measurement before running a scan. In general, when powering an LR circuit with a linear amplifier, maximum slew rates are dictated by the LR time constant of the system. It thus may be desirable or imperative to design transmit/excitation/drive coils with a low inductance for adequate slew rates.

A pre-emphasized voltage waveform so constructed may be supplied to the power amplifier in real time during a scan to achieve maximal field slew rates with minimal ringing or other forms of distortion. Common mode rejection, filtering components, and shielding systems may be installed. For maximum flexibility in temporal resolution in applying pre-emphasis, care must be taken in choosing the sampling rate for the waveform controlling the power amplifier. This sampling rate may be approximately 1 MHz or may require higher sampling rates such as 10 MHz or higher. Similar results in terms of driving coils with pulsed waveforms may be obtained by operating a linear amplifier in controlled current mode in which an internal feedback control loop works to achieve pulsed waveform components such as rapid transitions through rising and/or falling edges given an ideal waveform target. To achieve prompt and rapid feedback adjustment, the linear amplifier may be modified to allow for high voltage slew rates, or in the case where high voltage slew rates are not possible, set up with a predictive computational algorithm or electronic circuit to avoid instability in the feedback loop and avoid ringing.

Resonant Switcher Circuit

Figure 46:
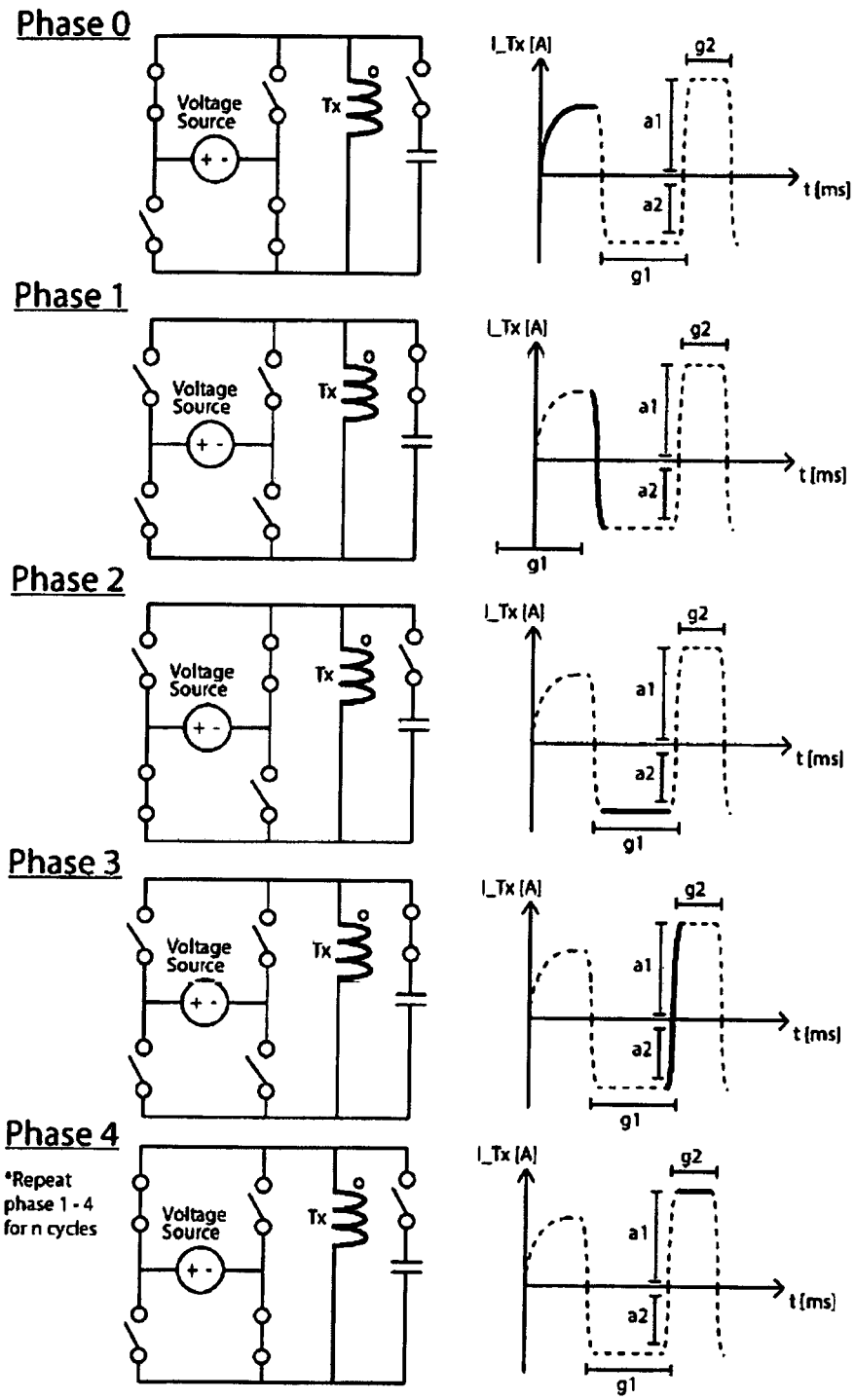
FIG. 46 shows a switching transmit circuit embodiment for pulsed MPI excitation according to an embodiment of the current invention.

In some embodiments, a switcher circuit may be used to realize pulsed excitation waveforms. In this approach, a transmit circuit system switches between various states according to precise timing diagrams as depicted in FIG. 46. A transmit coil is connected with a capacitor for a fraction of a resonant period in order to rapidly change the current in the transmit coil before disconnecting the capacitor, via controllable switches with rapid switch times, to achieve substantially constant current in the coil over a gliding period. The capacitance of the capacitor may be chosen to achieve a desired slew rate possibly providing more flexibility in the inductance of the coil. Each time the current needs to transition between substantially constant regions, the capacitor is reconnected briefly. Precise timing of the switching is crucial for circuit operation and is enabled by appropriately designed switches that can be controlled, for example with a temporal resolution of better than 10 microseconds, or better than 1 microsecond, or better than 0.1 microseconds. FIG. 46 shows an exemplary switch timing diagram used to generate the desired features, the current through the excitation coil over time that results, and the circuit topology at each distinct stage. These designs are meant to be instructive and exemplary and in no way limiting.

Transmit Coil Designs

The pulsed waveforms may be applied to transmit, drive, or excitation coils. These excitation coils will generally be designed to provide a spatially homogeneous but time-varying field to the imaging FOV. To facilitate certain desirable signal encoding strategies and MPI trajectories in pulsed MPI, this disclosure contemplates multiple transmit coil arrangements. To support certain rotating or projective encoding strategies, it may be desirable to have excitation coils with principal axes that are orthogonal to each other. For example, in an FFL MPI system in which the direction of the line is taken as the y-axis, excitation coils may be placed concentric with the x- and z-axes as shown in FIG. 3. These coils may be driven in quadrature mode to provide excitation or shift pulses along any direction in the xz plane as illustrated in FIG. 14. In the case of an FFP system, a system of at least three orthogonal excitation coils, aligned with each of three established principal axes can provide analogous flexibility in terms of excitation direction.

To achieve the rapid transitions through rising and/or falling edges required in some pulse sequences, high slew rates (of voltages, currents, or magnetic fields) are required and it is important to prevent or minimize sources of ringing and distortion. Excitation coils may be designed with a low inductance, for example, with an inductance value between 1 microHenry and 30 microHenries. This will facilitate faster current transitions (shorter rise times for each pulse) in embodiments where the coil is part of an LR circuit and driven with a linear voltage amplifier. In some embodiments, the transmit coil is a single wire loop that may be hollow for passage of cooling fluid, such as a liquid or gas. In some embodiments Litz wire will be used to construct excitation coils. These coils may be of solenoidal, saddle, Helmholtz-like, or other coil designs, depending on factors such as geometric relationship with the fixed imaging bore and the need for low inductance coils. In some embodiments, the transmit coil is made up of a single Helmholtz or Maxwell pair. In some embodiments, the transmit coil has a small diameter to reduce inductance.

In some applications in which an FFL-like scanning system is used, it may be desirable to install transmit coils concentric with the axis of the line of the FFL as illustrated in FIG. 3 and FIG. 15. This is in addition to one or more coils oriented with sensitivity in the plane normal to the line. The coil concentric with the FFL axis provides an ability to bias or excite all particles along the line without physically translating the line in the orthogonal plane and enables various signal encoding schemes described in previous section.

Methods of Shifting the FFR-Sample Relative Geometry for Full FOV Coverage

As illustrated in FIG. 17 and FIG. 18, a general pulsed MPI acquisition will entail repeated application of pulsed excitation waveforms while shift waveforms provide a total x-space trajectory that allows sampling of a large imaging FOV over time. The shift waveforms denoted in these pulse sequence diagrams refer to movements of the FFR isocenter and/or total FFR structure location over time relative to the imaging FOV and sample. This relative movement may be accomplished in more than one way. In some embodiments, shift waveforms are applied to high power homogeneous electromagnets arranged to shift the total FFR structure along the central axis of the electromagnet. In some embodiments, the sample itself may be moved by mechanical means, such as using an arrangement of a sample holder, moveable stage, and motor. In some embodiments, both mechanical movement of the sample and electromagnet shifting of the FFR will be employed in a total x-space imaging scan. FIG. 43 illustrates how mechanical apparatuses and shift magnets may be arranged in this context.

An important component of an imaging scanner is shielding between an inner region and an outer region. As depicted in FIG. 43, the inner region contains the area defined as the imaging bore into which the sample is placed, one or more excitation coils, one or more receive coils, and possibly one or more shifting electromagnets. The inner region is fully electromagnetically isolated from the outer region: the rest of the space in the scanner and the external world. One or more of the shifting electromagnets may be located in the outer region, the FFR generating source (electromagnet or permanent magnet), motors, stages, etc. are all placed in the outer region. The electromagnetic isolation may be provided by a single continuous solid copper eddy-current shielding system. This shield removes interference and noise sources from coupling into the excitation or receive systems and disallows the transmit and/or shift systems of the inner bore from interacting with elements in the outer region (e.g., the soft magnetic materials, shift magnets, or FFR generating magnets). As depicted in FIG. 43, the entirety of the excitation electronics chain and the receive electronics chain may also be located in the inner shielded region.

Cooling

Many aspects of an MPI scanning system may require cooling during operation. In some embodiments, the transmit or excitation coils will be actively cooled as well as shift magnets and FFR-generating electromagnets. In some embodiments, aspects of the eddy-current shielding system may be cooled as well. In some embodiments, water or alternative cooling fluids such as the fluoro-carbon based Fluorinert will be used to cool hollow electromagnet wire and coils. In some embodiments, elements will be cooled by placement in thermal fluid baths.

Safety Considerations.

Care must be taken in using such large slew rates in terms of specific absorption rate (SAR) considerations for the subject. In some cases, magnetostimulation effects may apply as well. The high slew periods in pulsed MPI are by definition short and thus may represent a small duty cycle inside of a single excitation period. In the context of the larger periodicity of the pulsed excitation waveform, pulsed MPI waveforms will be subject to the same or similar measures of SAR limitation as, for example, calculated in a root-mean-square (RMS) sense.

Pulsed MPI Receive Systems

In MPI, inductive receiver coils are used to detect the magnetization signal from magnetic nanoparticle tracers. Traditionally, a continuous sinusoidal excitation waveform is applied while the signal is received. Because the transmit and receive coils are strongly coupled, in general, this leads to significant excitation feedthrough into the receiver coil. Without mitigation, this feedthrough is orders of magnitude larger than the tracer signal. Geometric decoupling strategies such as use of receiver coils wound in a gradiometric fashion with zero net area with respect to the geometry defined by the transmit coil are typically used.

Figures 47, 48:
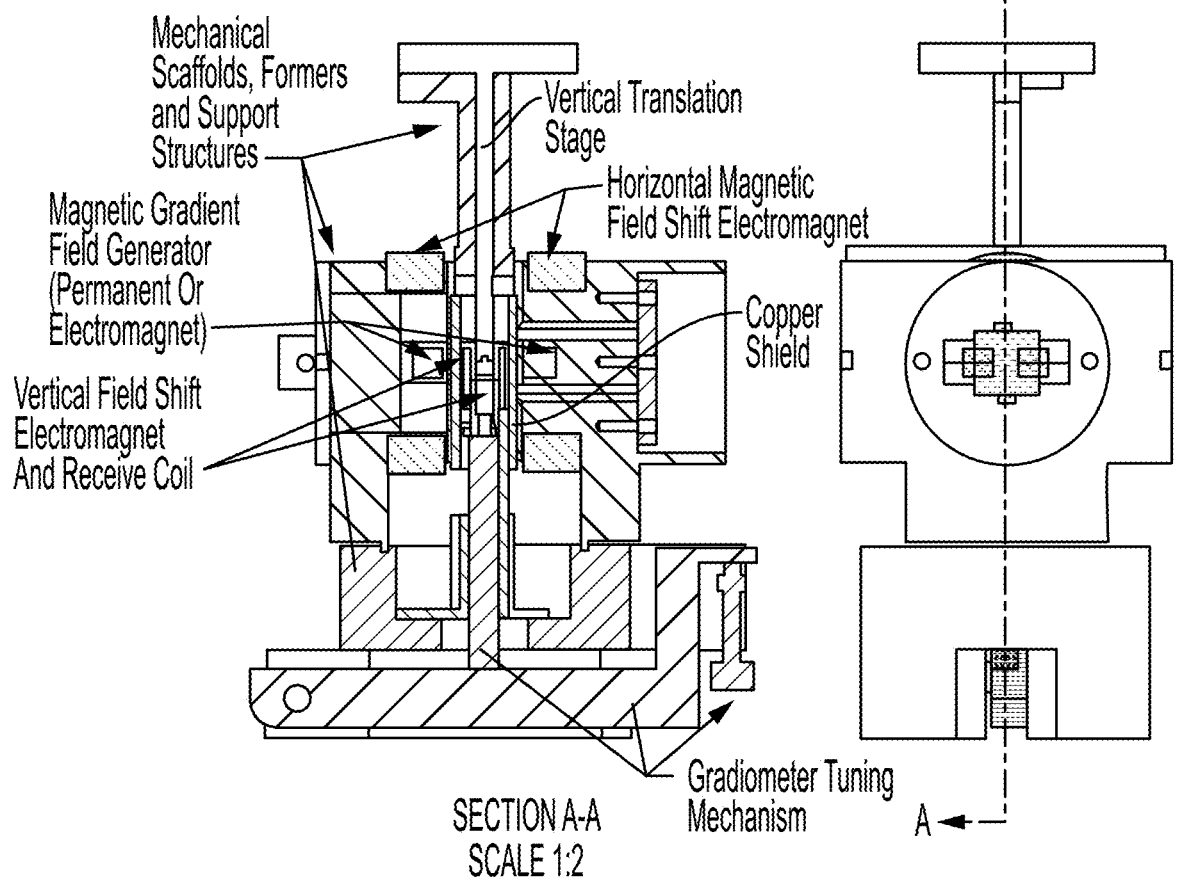
FIG. 47 is an illustration of an AWR device according to an embodiment of the current invention.
FIG. 48 is a cross-sectional view of the AWR device of FIG. 47 take at the cut line 48.

Pulsed MPI has direct feedthrough across a wide frequency band. In some embodiments inductive decoupling via finely-tuned gradiometers and/or active cancellation will be employed. In some embodiments, inductive decoupling is improved by spatial-shimming of the gradiometer coils relative to the transmit coil. In some embodiments, inductive decoupling is improved by a tunable voltage divider (to finely adjust amplitude of a portion of the receive coil) and/or a tunable capacitor (to finely adjust the phase differences between portions of the receive coil). FIGS. 47 and 48 show an exemplary tunable gradiometer design for an MPI arbitrary waveform relaxometer (AWR) and details of the AWR design. An AWR is a table-top MPI device that allows for characterization of a sample and typically does not have an implementation of a gradient. Instead, the entire sample is taken through a trajectory in the applied field magnitude space that is linearly proportional to the experience of a point source in a scanning system when a linear gradient is used. Such a device can easily measure 1D PSFs (e.g., both tracer density and relaxation imaging) associated with a tracer sample and allows for the testing of different MPI pulse sequences.

In addition to a gradiometric receiver coil design, a typical sinusoidal MPI receive chain may contain a notch filter at the fundamental excitation frequency as well as one or more other filters (low pass, high pass, or band pass) that, among other purposes, endeavor to fully remove all received signal at the fundamental frequency. It is typical to remove this component due to an inability to separate tracer signal at the fundamental frequency from excitation feedthrough and possibly the linear diamagnetic signal of imaged materials in the case of large samples. Loss of the tracer signal at the fundamental harmonic has major ramifications for signal linearity and shift invariance (LSI) in MPI and necessitates important steps in reconstruction to recover LSI. This requirement adds constraints on signal acquisition and encoding trajectories, adds complexity to the reconstruction process, and reduces overall signal-to-noise ratio (SNR). Further digital signal processing and baseline subtraction approaches may be leveraged for feedthrough mitigation and signal conditioning once the received signal is digitized and prior to image reconstruction.

A key aspect of pulsed MPI is the ability for temporal decoupling of the feedthrough from the nanoparticle signal.

This is not possible in standard continuous sinusoidal wave MPI. When using pulsed waveforms, the circumstances of excitation feedthrough will be very different, in general. When using pulsed waveforms with substantially constant components over a period of time, the excitation feedthrough is not present after the substantially constant value is attained and an amount of time has passed in which the system response falls to zero. Furthermore, if the substantially constant value is arrived at after a rapidly transitioning rising and/or falling edge, and the system response time is very short as previously described, then there is only a very short period of time during each excitation cycle or period in which feedthrough is significantly present. This allows complete temporal separation of excitation feedthrough from tracer signal in the limit of short system response times. For finite system response times, the degree of feedthrough and signal separation is a function of the system response time and the magnetic tracer response time. In general, system response times much shorter than the tracer response time may be desired.

Figure 49:
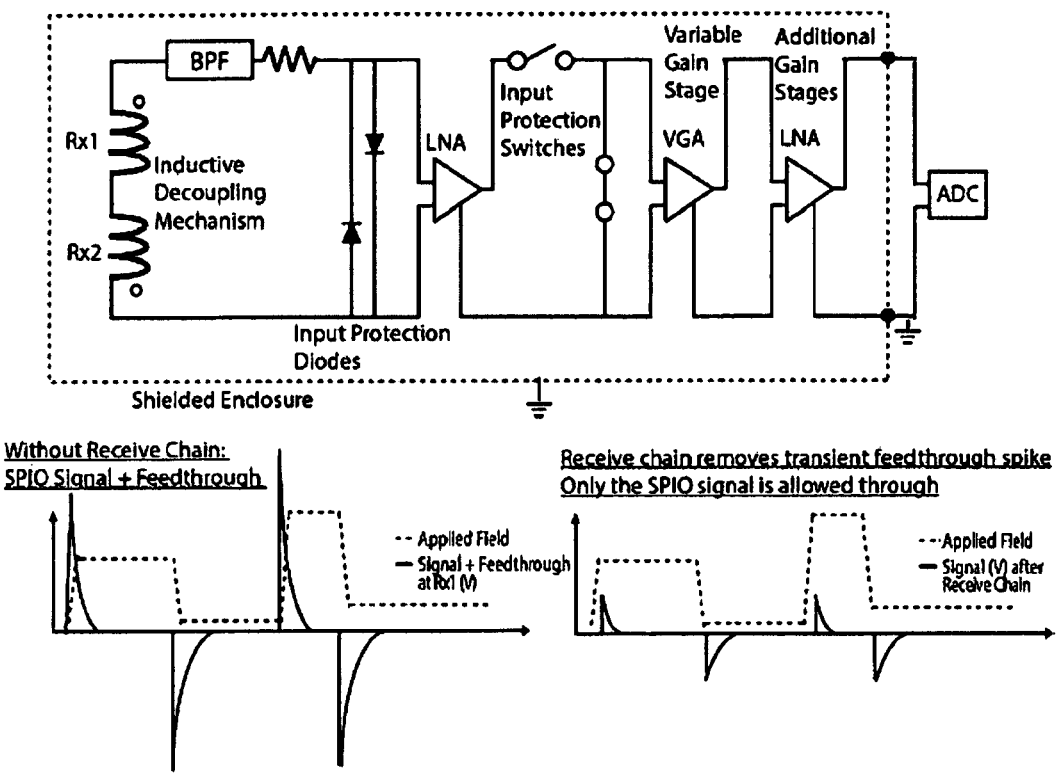
FIG. 49 illustrates a receiver chain according to an embodiment of the current invention.
Figure 50:
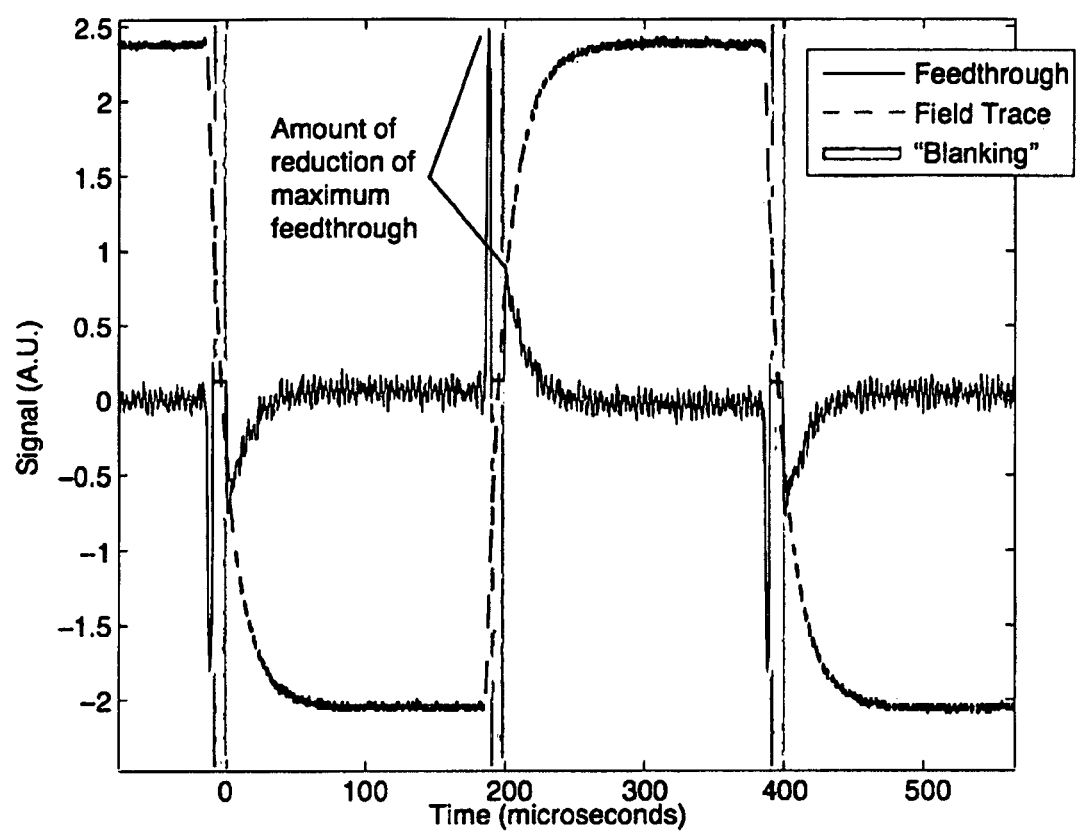
FIG. 50 provides data showing use of VGA, pre-emphasis according to an embodiment of the current invention.

Although direct feedthrough can be limited to a very short window of time with pulsed encoding strategies, without mitigation, it may damage sensitive pre-amplifier systems set with gains ideal for the part of the signal in which the magnetic tracer signal alone is present. If the gain of the pre-amplifier system or systems is reduced to accommodate this peak, one or more of reduced dynamic range, reduced SNR, and increased discretization error will result. To avoid these adverse effects and maximize received signal dynamic range, multiple strategies may be leveraged. In some embodiments, a variable gain amplifier selectively amplifies the temporally delayed nanoparticle signal while not amplifying the initial direct feedthrough signal. In some embodiments, a blanking signal, precisely correlated with the excitation feedthrough aspects of each excitation cycle, period, or pulse, may be sent to a variable gain amplifier (VGA) system to switch between a low gain during the period of feedthrough and a high gain at other times. The system response time may be characterized and the blanking signal used to lower the gain of the receiver system beginning some finite time before the system response begins and ending some small finite time after the system response decays to a small value of choice. Subject to the response time of this VGA system itself, the excitation feedthrough signal can be greatly attenuated and the dynamic range and total amplification of desirable signal in readout can be maximized. FIG. 49 shows an exemplary receive circuit design with these features and FIG. 50 shows exemplary data from a working system demonstrating the combined use of transmit voltage pre-emphasis with a linear amplifier along with a receive system implementing a VGA with a blanking signal.

In some embodiments, crossed diodes circuits which reject voltages beyond a certain threshold value, as depicted in FIG. 49 can be used to limit the direct feedthrough signal. In some embodiments, the feedthrough signal can be briefly shunted away from the signal path through the use of digitally-controlled switches such as IGBTs, MOSFETs, or other voltage-controlled switches. In some embodiments, electronic delays may be used to enhance temporal decoupling of feedthrough and nanoparticle signal. In some embodiments, the pre-amplifiers and gain stages may be briefly turned off to protect them from overvoltage during the feedthrough period and rapidly switched back on to receive and amplify the (delayed) nanoparticle signal. In some embodiments, the input to the pre-amplifiers may be specifically blanked only during the feedthrough period. One or more of these strategies may be employed simultaneously in a total receiver system design for a pulsed MPI system as depicted in FIG. 49.

In many pulsed MPI encoding strategies, especially those that leverage rapidly transitioning rising and/or falling edges, a significant part of the tracer signal may be contained in a short period of time following the rising and/or falling edge. It is important that the receiver system is configured with a bandwidth capable of fully capturing this signal in a Nyquist-limit sense. Sampling rates in the range of 1 MHz may suffice, but sampling rates up to 10 MHz or more may be required.

In some embodiments, detection of the raw received signal across a wide bandwidth is desired. In such embodiments, a receive bandwidth ranging from DC up to 10 MHz or more may be desired. In other embodiments, a reduced signal bandwidth may be desirable to modulate SNR and/or spatial resolution in image reconstruction. In some embodiments, a large signal bandwidth up to 10 MHz or more will be sampled by the data acquisition system and subsequent digital signal processing will reduce the bandwidth as desired during reconstruction. In other embodiments, the receiver systems may be configured with bandwidth-limiting filters for noise suppression. For example, a small bandwidth may be kept around the fundamental harmonic (this bandwidth determined by system parameters such as shift field slew rates and a fundamental frequency referring to the periodic excitation waveform), or a bandwidth around some small number N of harmonics of the fundamental periodic excitation waveform may be desired. FIG. 32 shows experimental data reconstructing 1D pulsed MPI images using 1 to 15 such harmonic bands. In some embodiments the bandwidth may be less than 1 kHz, less than 500 Hz, or less than 250 Hz. In some embodiments such narrowband sampling will be used in optimizing noise matching between receiver coils and detector electronics. In some embodiments, parallel hardware such as filter banks will enable narrowband detection at more than one center frequency (e.g., excitation harmonic). In some embodiments, techniques such as lock-in amplification methods may be employed when narrowband detection is desired. In some embodiments, one or more of the MPI excitation waveform fundamental frequency, length of substantially constant periods in the excitation waveform, slew rates of slow shifting waveform components, and receive bandwidth will be optimized to achieve and/or tradeoff resolution, SNR, and SNR-efficiency metrics as desired.

Modularity of Pulsed Hardware Components

Figure 51:
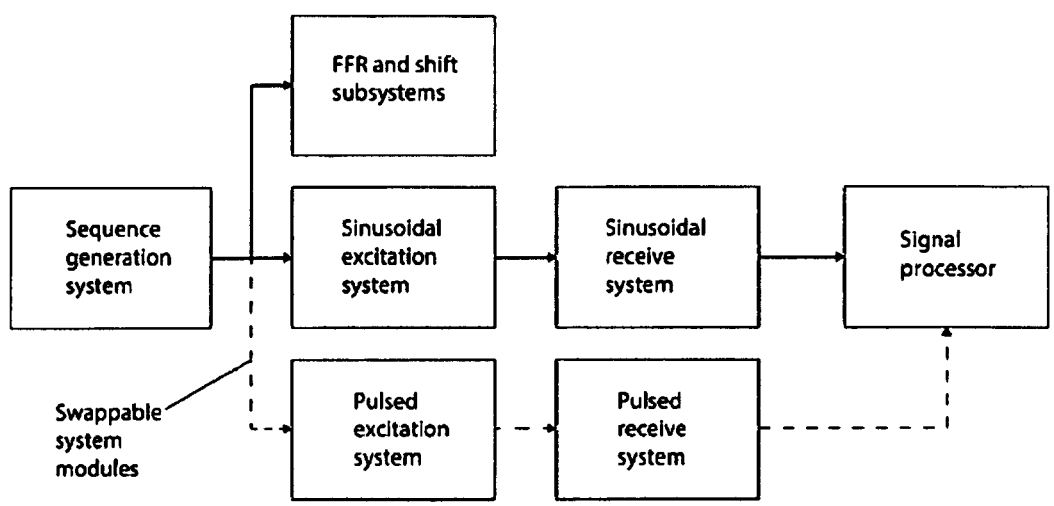
FIG. 51 is a schematic illustration of modular/swappable pulsed MPI hardware according to an embodiment of the current invention.
Figure 52:
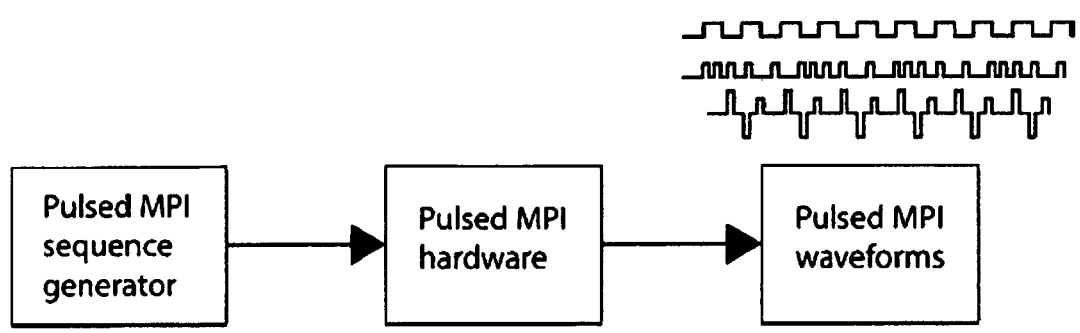
FIG. 52 is a schematic illustration of a model of sequence generator and enabling hardware for pulsed MPI waveforms according to an embodiment of the current invention.
Figure 53:
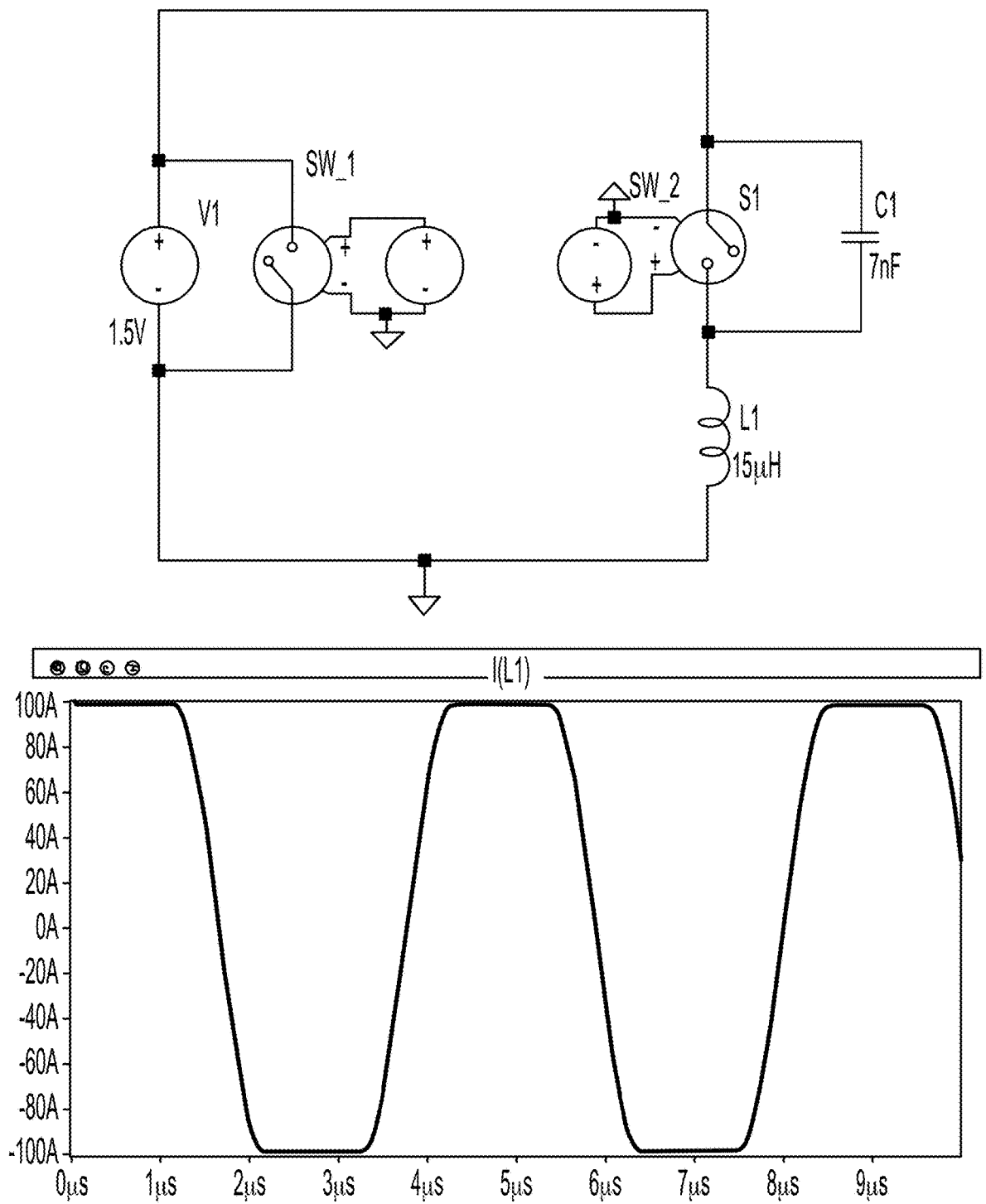
FIG. 53 shows an example of a transmit switcher circuit according to an embodiment of the current invention.

Pulsed MPI requires major deviations from traditional MPI methods in the excitation and receive chains. Other aspects of the hardware may be maintained. For example, the magnetic field source components that generate the FFR and slowly (relative to the excitation periods) shift the FFR to cover a large imaging FOV may be constructed and used in the same or a similar manner as used in a sinusoidal MPI system. It may be desirable to design an MPI scanning system in which modular pulsed MPI excitation and receive systems are swappable or switchable with modular sinusoidal excitation and receive systems, as illustrated in FIG. 51. Such a design would also facilitate modular swapping or switching of pulsed MPI excitation/receive systems with different characteristics. This could be desirable if such systems traded off fundamental parameters such as system response time and imaging SNR. Because a key design relationship is between system response times and tracer magnetic relaxation times, certain pulsed MPI excitation/ receive systems may be optimally matched to specific tracers or specific applications of tracers.

Pulsed MPI Signal and Imaging Equations in 1D

Here we provide a basic derivation of one dimensional pulsed MPI methods using ideal square wave excitation. This analysis is for a small number of idealized pulsed MPI methods, is intended to further illustrate some of the basic concepts, and is in no way limiting.

Steady-State Square Wave Imaging

The steady-state magnetization of a distribution of superparamagnetic magnetic particles in a field of view is described as:

$$M_{SS}(t,x) = m\rho(x)\mathcal{L}(kH(t,x))$$

where m is the magnetic moment of a single particle, rho is the particle density, L is the Langevin function, k is a tracer-specific term, and H is the applied field.

The 1D square wave excitation contribution to the location of the MPI FFR can then be expressed as:

$$x_s(t) = \sum_{n=0}^{k}(-1)^n \Delta x \, rect\left(\frac{t - n\Delta t}{\Delta t}\right)$$

where Delta x is the x-space displacement of the FFR and is equal to the square wave excitation amplitude in Tesla multiplied by the linear gradient strength of the MPI device in Tesla per meter. The voltage on a receiver coil, by inductive physics is:

$$V(t) = B_1 \frac{d}{dt}\int_u M(t,u)du$$

Considering the response at each n-th step excitation, we can derive a signal equation:

$$s_n(t) = V(t)\Big|_{t_n}^{t_{n+1}}$$

$$= B_1 \frac{d}{dt}\int_u M_{ss}(t,u) \overset{t}{*} h_m(t, u - u_n)du \Big|_{t_n}^{t_{n+1}}$$

$$= B_1 \int_u \Delta M_n(u) h_m(t - t_n, u - u_n) du \Big|_{t_n}^{t_{n+1}}$$

where Delta $M_n$(x) is the difference between the steady-state magnetization states before and after the n-th square wave step excitation, $h_m$(t, x) is the magnetic particle relaxation impulse response that is a function of position because of the strong field-dependence of tracer relaxation and the presence of strong gradient fields in MPI. This signal equation expresses that, in the ideal square wave case, the received voltage signal is a scaled form of the tracer relaxation impulse response integrated over space. This explicitly shows how tracer impulse responses, as well as steady-state information (via Delta $M_n$) are directly encoded in the raw time domain data.

We can further establish an indexed signal equation by integrating the signal under each half-period as previously described:

$$s(n) = \int_{t_n}^{t_{n+1}} s_n(t) dt$$

-continued $$= B_1 \int_{t_n}^{t_{n+1}} \left(\int_u \Delta M_n(u) h_m(t-t_n, u-u_n)du\right)dt$$

$$= B_1 \int_u \Delta M_n(u)\left(\int_{t_n}^{t_{n+1}} h_m(t-t_n, u-u_n)dt\right)du$$

$$= B_1 \int_u \Delta M_n(u) du$$

$$= B_1 \int_u (m\rho(u)\mathcal{L}(kG(u-u_n)) - m\rho(u)\mathcal{L}(kG(u-u_{n-1})))du$$

$$= B_1 m\rho(x) \overset{x}{*}\left(\dot{\mathcal{L}}(kGx)\overset{x}{*} rect\left(\frac{x}{2\Delta x}\right)\right)\Big|_{x=x_n - \Delta x}$$

where we assume the half-period of the square wave excitation is long enough to fully establish steady-state conditions everywhere by the end of the half-period. In this case, the impulse response components integrate to unity and we are left with a finite difference between steady-state magnetization states before and after the step. We can express this result as a convolution relation as shown in the final step. $2\Delta x = 2 \, AG^{-1}$ is the FFR excursion distance in a square wave step excitation where A is the square wave amplitude and G is the MPI gradient strength.

Finally we can establish an imaging equation by dividing out the known scalar quantities:

$$\hat{\rho}(x) = \frac{s(n)}{B_1 m}\Big|_{x=x_n - \Delta x}$$

$$= \rho(x) \overset{x}{*} \dot{\mathcal{L}}(kGx) \overset{x}{*} rect\left(\frac{x}{2\Delta x}\right)\Big|_{x=x_n - \Delta x}$$

$$= \rho(x) \overset{x}{*} h(x) = \rho(x) \overset{x}{*} h_{\dot{L}} \overset{x}{*} h_r(x)\Big|_{x=x_n - \Delta x}$$

where our imaging PSF h(x) itself can be decomposed into a steady-state Langevin component, with no relaxation effects, and a rectangular blur which is controllable through our choice of excitation amplitude.

Relaxation Imaging

It is possible to directly quantify the magnetic relaxation process that evolves over each square wave half-period and construct relaxation images with this information. In one such embodiment, we can approximate our received signal for each half-period as a weighted exponential:

$$s_n(t) \approx B_1 \Delta M_n A_n \exp(-t/\tau_n)\Big|_{t_n}^{t_{n+1}}$$

We can then fit the time constant $\tau_n$ and the amplitude $A_n$ for each half-period and grid to the mean location of the FFR for the half-period. We may also enforce specific a priori knowledge or expectation, such as $A_n = \tau_n^{-1}$, if we believe a Debye exponential model adequately describes the relaxation process. This provides an image of relaxation dynamics over space rather than tracer mass/concentration.

Time Domain Relaxation Weighted Imaging

We can understand the effect of relaxation weighting to improve spatial resolution by exploiting the secondary spatial encoding of relaxation dynamics as follows. Unlike our steady-state square wave analysis, we do not integrate the entire signal associated with a square wave half-period, but only some latter part specified by a windowing threshold.

$$s_{rw}(n) = \int_{t_n + t_w}^{t_{n+1}} s_n(t)$$

-continued $$= B_1 \int_u \Delta M_n(u) \left( \int_{t_n+t_w}^{t_{n+1}} h_m(t-t_n, u-u_n) dt \right) du$$

$$= B_1 \int_u \Delta M_n(u) \cdot w_n(u) du$$

where $s_{rw}(n)$ is our indexed signal equation for relaxation weighted reconstruction. Delayed windowing in this manner leads to the presence of a spatial weighting function $w_n(x)$. Following similar analysis as in the fully integrated case, we arrive at a modified imaging equation for relaxation weighted reconstruction:

$$\hat{\rho}_{rw}(x) = \frac{s_{rw}}{B_1 m} \bigg|_{x=x_n-\Delta x}$$

$$= \rho(x) \overset{x}{*} (h(x) \cdot w(x)) \big|_{x=x_n-\Delta x}$$

$$= \rho(x) \overset{x}{*} h_{rw} \big|_{x=x_n-\Delta x}$$

where our relaxation weighted PSF, $h_w$, is the fully integrated, steady-state square wave PSF (h(x)) point-wise multiplied by our weighting function w(x). In the case of an exponential relaxation dynamics, the relaxation function may be approximated as follows $$w(x) = \int_{t_w}^{\infty} h_m(t,x) dt$$

$$\approx \int_{t_w}^{\infty} \tau^{-1}(x) \exp(-t/\tau(x)) dt$$

$$= \exp(-t_w/\tau(x))$$

Our relaxation weighted PSF can be understood as the relaxation-free steady-state square wave PSF point-wise multiplied by another narrow function, allowing us to improve resolution, potentially beyond the Langevin limit.

More complicated pulsed MPI excitation trajectories can be mathematically described in a similar manner. Arbitrary pulsed waveforms may most naturally be expressed as recurrence relations, for example. These few 1D mathematical descriptions of specific square wave approaches are intended for further illustration of these simple examples only and are in no way limiting.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A pulsed magnetic particle imaging system, comprising:
a magnetic field generating system comprising at least one magnet, said magnetic field generating system providing a spatially structured magnetic field within an observation region of said magnetic particle imaging system such that said spatially structured magnetic field will have a field-free region (FFR) for an object under observation having a magnetic nanoparticle tracer distribution therein;
a pulsed excitation system arranged proximate said observation region, said pulsed excitation system comprising an electromagnet and a pulse sequence generator electrically connected to said electromagnet to provide an excitation waveform to said electromagnet, wherein said electromagnet when provided with said excitation waveform generates an excitation magnetic field within said observation region to induce an excitation signal therefrom by at least one of shifting a location or condition of said FFR;
a detection system arranged proximate said observation region, said detection system being configured to detect said excitation signal to provide a detection signal; and
a signal processing and image rendering system configured to be in communication with said detection system to receive said detection signal therefrom,
wherein said excitation waveform comprises a magnetization preparation portion and a readout portion, said magnetization preparation portion comprising a transient portion, and said readout portion comprising a constant portion,
wherein said signal processing and image rendering system is configured to process said detection signal and render an image to represent magnetic relaxation dynamics of said magnetic nanoparticle tracer at corresponding image locations.

2. The pulsed magnetic particle imaging system of claim 1, wherein said substantially constant portion of said excitation waveform is at least 500 nanoseconds and less than 500 milliseconds.

3. The pulsed magnetic particle imaging system of claim 1, wherein said substantially constant portion of said excitation waveform is constant to within about 10% of a target amplitude of said excitation waveform.

4. The pulsed magnetic particle imaging system of claim 1, wherein said transient portion of said excitation waveform has a duration of at least 100 nanoseconds and less than 100 microseconds.

5. The pulsed magnetic particle imaging system of claim 1, wherein said magnetization preparation portion dynamically configures a state of tracer magnetization that is in a vicinity of said FFR based on magnetic relaxation properties of the tracer prior to said readout portion.

6. The pulsed magnetic particle imaging system of claim 1, wherein said readout portion is greater than a relaxation time for said magnetic nanoparticle tracer in said FFR.

7. The pulsed magnetic particle imaging system of claim 1, wherein said readout portion is long enough to establish a steady-state magnetization in said magnetic nanoparticle tracer in said FFR.

8. The pulsed magnetic particle imaging system of claim 1, wherein said readout portion is shorter than a relaxation time for said magnetic nanoparticle tracer in said FFR.

9. The pulsed magnetic particle imaging system of claim 1, further comprising a signal processor configured to communicate with said detection system to receive detection signals therefrom,
wherein said signal processor is further configured to generate an imaging signal for rendering an image corresponding to regions of said object under observation traversed by said FFR.

10. The pulsed magnetic particle imaging system of claim 1, further comprising a signal processing and image rendering system configured to be in communication with said detection system to receive said detection signal,
wherein said signal processing and image rendering system is configured to process said detection signal and render an image corresponding to portions of said object under observation containing said magnetic nanoparticle tracer and that was addressed by said FFR.

11. The pulsed magnetic particle imaging system of claim 10, wherein said signal processing and image rendering system is configured to process said detection signal and render said image to represent at least one of density, mass, concentration or a derivative thereof of said tracer at corresponding image locations.

12. The pulsed magnetic particle imaging system of claim 10, wherein said signal processing and image rendering system is configured to process said detection signal and render said image to represent a local measure of magnetic relaxation dynamics of said tracer at corresponding image locations.

13. A method of imaging an object using a magnetic nanoparticle tracer; comprising:
providing said object with said magnetic nanoparticle tracer;
applying a spatially structured magnetic field that has a field-free region (FFR) such that said FFR intercepts said object at a region of said object containing at least a portion of said magnetic nanoparticle tracer;
exciting a portion of said magnetic nanoparticle tracer by using an excitation waveform to change at least one of a property of said FFR and a position of said FFR;
detecting changes in magnetization of said magnetic nanoparticle tracer resulting from said exciting while said property of said FFR and said position of said FFR are substantially constant to obtain a detection signal;
repeating said exciting and detecting for a plurality of different locations of said FFR within said object to obtain a plurality of detection signals; and
processing said plurality of detections signals to render an image to represent magnetic relaxation dynamics of said magnetic nanoparticle tracer within the region of said object,
wherein said excitation waveform comprises a magnetization preparation portion and a readout portion, said magnetization preparation portion comprising a transient portion, and said readout portion comprising a constant portion.

14. The method of imaging an object according to claim 13, wherein said property of said FFR and said position of said FFR are substantially constant for at least 500 nanoseconds and less than 500 milliseconds during said detecting.

15. The method of imaging an object according to claim 13, wherein said property of said FFR and said position of said FFR are substantially constant to within about 10% of an amount of change of said FFR and said position of said FFR during said exiting.

16. The method of imaging an object according to claim 13, wherein said changing said property of said FFR or said position of said FFR has a duration of at least 100 nanoseconds and less than 10 microseconds.

17. The method of imaging an object according to claim 13, wherein said processing said plurality of detections signals to render said image of said region of said object renders at least one of a magnetic particle density image, or a magnetic relaxation dynamic parameter image.

18. A device for use with or as a part of a pulsed magnetic particle imaging system, comprising:
a pulsed excitation system arranged proximate a sample observation region, said pulsed excitation system comprising an electromagnet and a pulse sequence generator electrically connected to said electromagnet to provide an excitation waveform to said electromagnet, wherein said electromagnet provides a magnetic field within said sample observation region to generate an excitation signal from a sample when held by said sample holder in said sample observation region;
a detection system arranged proximate said sample observation region, said detection system being configured to detect said excitation signal from said sample to provide a detection signal; and
a signal processor configured to be in communication with said detection system to receive and process said detection signal, and render an image to represent magnetic relaxation dynamics of said magnetic nanoparticle tracer in said sample observation region;
wherein said excitation waveform comprises a magnetization preparation portion and a readout portion, said magnetization preparation portion comprising a transient portion, and said readout portion comprising a constant portion.

19. The device according to claim 18, wherein said pulsed excitation system and said detection system are part of a modular structure adapted to convert a non-pulsed MPI system into a pulsed MPI system.

20. The device according to claim 18, wherein said signal processor is further configured to process said detection signal to determine a magnetization relaxation time for magnetic particles within said sample.

* * * * *